US012053296B2

(12) United States Patent
Abreu

(10) Patent No.: US 12,053,296 B2
(45) Date of Patent: Aug. 6, 2024

(54) DEVICE CONFIGURED TO BE SUPPORTED ON A HUMAN BODY, TO MEASURE A BIOLOGICAL PARAMETER OF THE HUMAN BODY, AND TO CONTROL A CHARACTERISTIC OF THE HUMAN BODY

(71) Applicant: Brain Tunnelgenix Technologies Corp., Aventura, FL (US)

(72) Inventor: Marcio Marc Abreu, Bridgeport, CT (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 214 days.

(21) Appl. No.: 15/096,189

(22) Filed: Apr. 11, 2016

(65) Prior Publication Data

US 2016/0296168 A1    Oct. 13, 2016

Related U.S. Application Data

(60) Provisional application No. 62/145,337, filed on Apr. 9, 2015.

(51) Int. Cl.
*A61F 7/00* (2006.01)
*A61B 5/00* (2006.01)
(Continued)

(52) U.S. Cl.
CPC .............. *A61B 5/4836* (2013.01); *A61B 5/01* (2013.01); *A61B 5/6803* (2013.01); *A61F 7/007* (2013.01); *A61F 7/02* (2013.01); *A61F 2007/0002* (2013.01); *A61F 2007/0003* (2013.01); *A61F 2007/0004* (2013.01); *A61F 2007/0006* (2013.01); *A61F 2007/0007* (2013.01); *A61F 2007/0008* (2013.01);
(Continued)

(58) Field of Classification Search
CPC ...... A61F 7/00; A61F 7/08; A61F 7/12; A61F 2007/0002; A61F 2007/0007; A61F 2007/0011; A61F 2007/0003; A61F 2007/0004; A61F 2007/0005; A61F 2007/003; A61M 16/0402; A61M 16/04; A61M 16/1075; A61M 16/0633; A61M 16/06; A61M 16/0683; A41D 13/11; A41D 20/005; A61B 5/6803; A61B 5/01; G02C 11/00; G02C 11/10
See application file for complete search history.

(56) References Cited

U.S. PATENT DOCUMENTS 3,209,755 A   10/1965   McCarthy et al.
5,193,534 A   3/1993    Peppler
(Continued)

OTHER PUBLICATIONS

International Preliminary Report on Patentability mailed on Oct. 19, 2017, in corresponding PCT Application No. PCT/US16/26989, 7 pp.
(Continued)

*Primary Examiner* — Joanne M Rodden
*Assistant Examiner* — Yasamin Ekrami
(74) *Attorney, Agent, or Firm* — Studebaker & Brackett PC

(57) ABSTRACT

The described apparatuses, devices, and mechanisms are configured to measure the temperature of one or more Abreu brain thermal tunnel (ABTT) terminuses. In addition, some embodiments are configured to provide treatment for the diagnosed conditions and diseases.

20 Claims, 50 Drawing Sheets

(51) Int. Cl.
*A61B 5/01* (2006.01)
*A61F 7/02* (2006.01)
*A61F 7/12* (2006.01)

(52) U.S. Cl.
CPC ............... *A61F 2007/0009* (2013.01); *A61F 2007/0011* (2013.01); *A61F 2007/0071* (2013.01); *A61F 2007/0075* (2013.01); *A61F 2007/0078* (2013.01); *A61F 2007/0093* (2013.01); *A61F 2007/0094* (2013.01); *A61F 2007/0096* (2013.01); *A61F 2007/0228* (2013.01); *A61F 7/12* (2013.01)

(56) References Cited

U.S. PATENT DOCUMENTS

| | | | | |
|---|---|---|---|---|
| 6,517,510 | B1* | 2/2003 | Stewart | A61F 7/02 604/113 |
| 6,896,367 | B1* | 5/2005 | Sohn | G02C 1/02 351/110 |
| 2002/0120317 | A1* | 8/2002 | Fletcher | A61F 7/10 607/109 |
| 2003/0055473 | A1* | 3/2003 | Ramsden | A61F 7/10 607/109 |
| 2005/0149153 | A1* | 7/2005 | Nakase | A61F 7/02 607/108 |
| 2007/0112401 | A1* | 5/2007 | Balachandran | A61F 7/02 607/104 |
| 2008/0151179 | A1 | 6/2008 | Howell et al. | |
| 2009/0105605 | A1* | 4/2009 | Abreu | A61B 5/0008 600/549 |
| 2010/0113894 | A1 | 5/2010 | Padiy | |
| 2010/0204765 | A1* | 8/2010 | Hall | A61M 1/166 604/27 |
| 2010/0292765 | A1* | 11/2010 | Etwil | A61F 7/123 607/105 |
| 2011/0172750 | A1* | 7/2011 | Cassidy | A61F 7/007 607/108 |
| 2012/0316459 | A1 | 12/2012 | Abreu | |
| 2013/0000642 | A1* | 1/2013 | Fearnot | A61M 16/0493 128/204.15 |
| 2013/0184554 | A1* | 7/2013 | Elsheikh | A61B 3/16 600/398 |
| 2014/0160424 | A1 | 6/2014 | Benko et al. | |
| 2014/0194961 | A1* | 7/2014 | Evans, Jr. | A61F 7/106 607/112 |
| 2014/0200475 | A1* | 7/2014 | Rubin | A61M 16/06 600/532 |
| 2014/0313309 | A1* | 10/2014 | Matsuo | A61B 5/01 348/78 |
| 2014/0358203 | A1* | 12/2014 | Li | A61F 7/00 607/108 |
| 2015/0068525 | A1* | 3/2015 | Belson | A61M 16/026 128/204.15 |
| 2015/0073516 | A1* | 3/2015 | Acharya | A61F 7/08 607/114 |
| 2015/0128945 | A1* | 5/2015 | Nickol | A61M 16/0622 128/204.15 |
| 2015/0238349 | A1* | 8/2015 | Giuliani | A61F 7/00 602/2 |
| 2016/0022478 | A1* | 1/2016 | Schaefer | A61F 7/007 607/104 |
| 2016/0345652 | A1* | 12/2016 | Harty | A61B 5/01 |

OTHER PUBLICATIONS

Notification of Transmittal of the International Search Report and the Written Opinion of the International Searching Authority; PCT/US2016/026989 issued on Jul. 6, 2016.
International Search Report issued Jul. 6, 2016 in corresponding PCT Application No. PCT/US2016/026989, 3pp.
Written Opinion issued Jul. 6, 2016 in corresponding PCT Application No. PCT/US2016/026989, 5pp.
David G. Silverman, M.D., Wide Potential for Non-invasive Brain Temperature Monitoring System, ASA Monitor, Jan. 2018, pp. 18-19, vol. 82, American Society of Anesthesiologists.

* cited by examiner

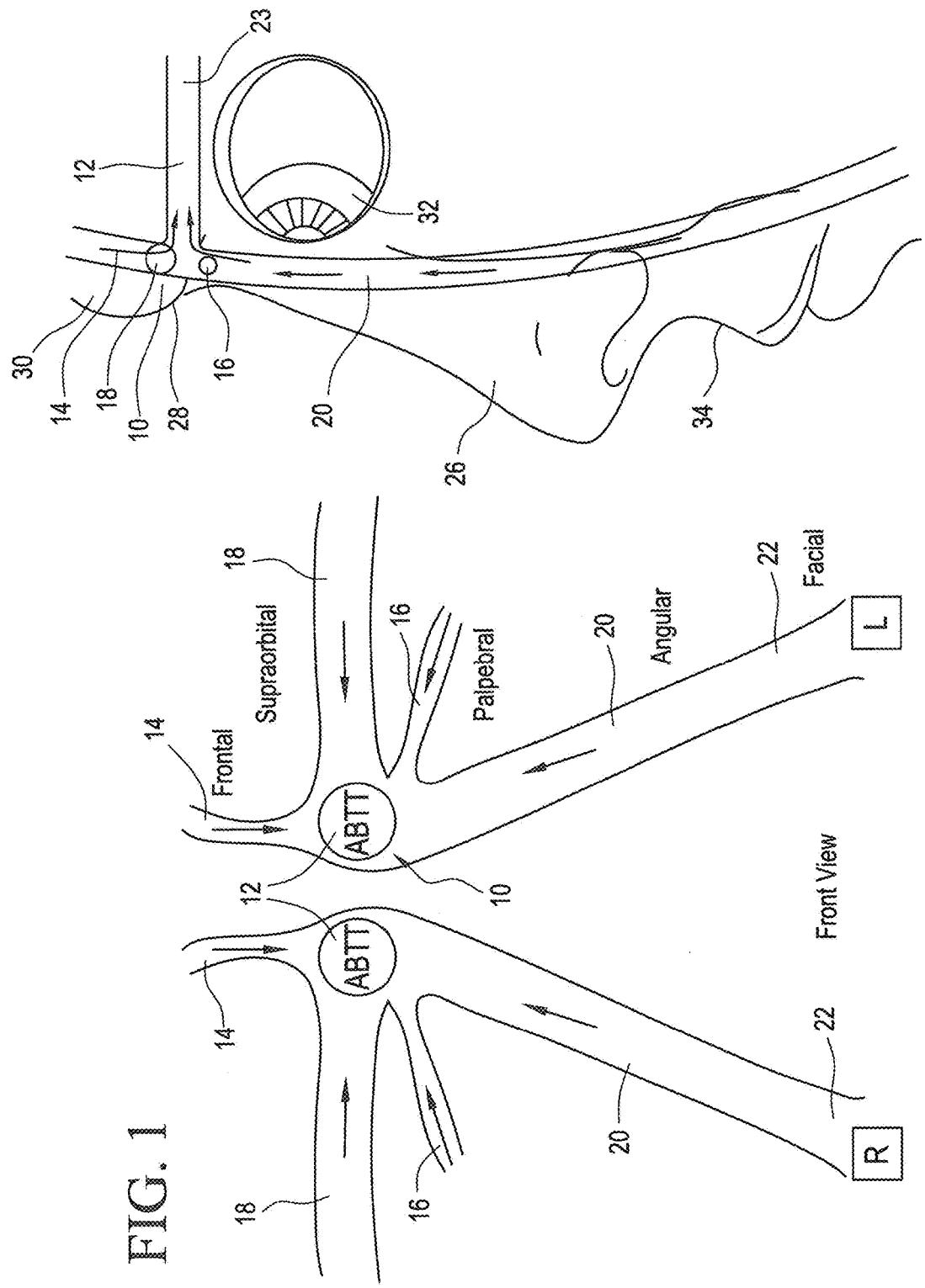

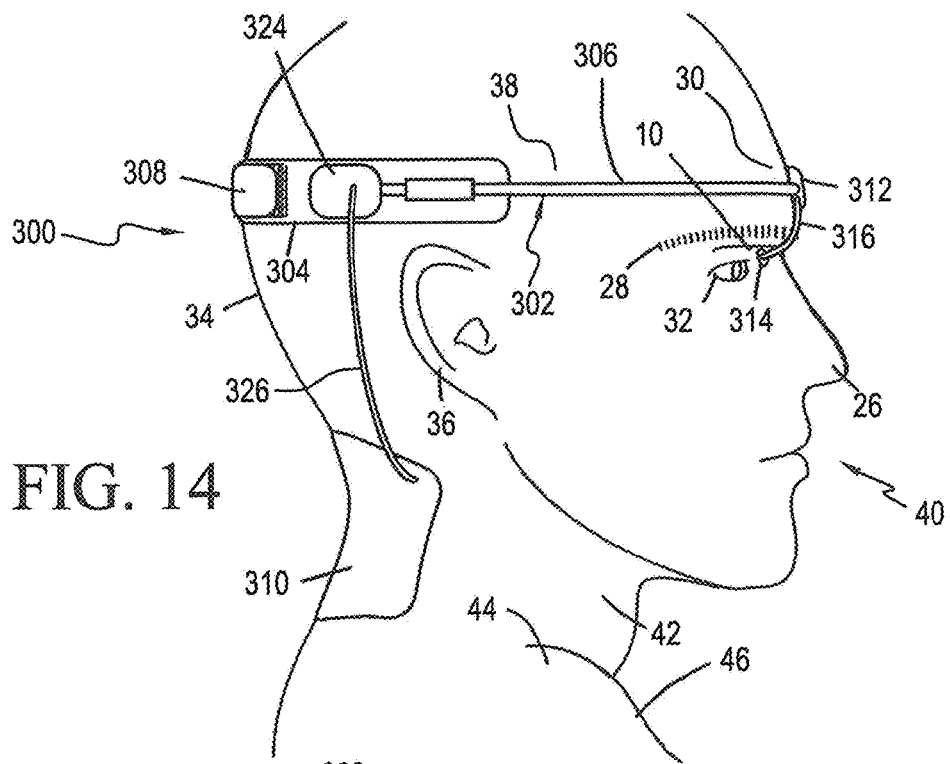
FIG. 14
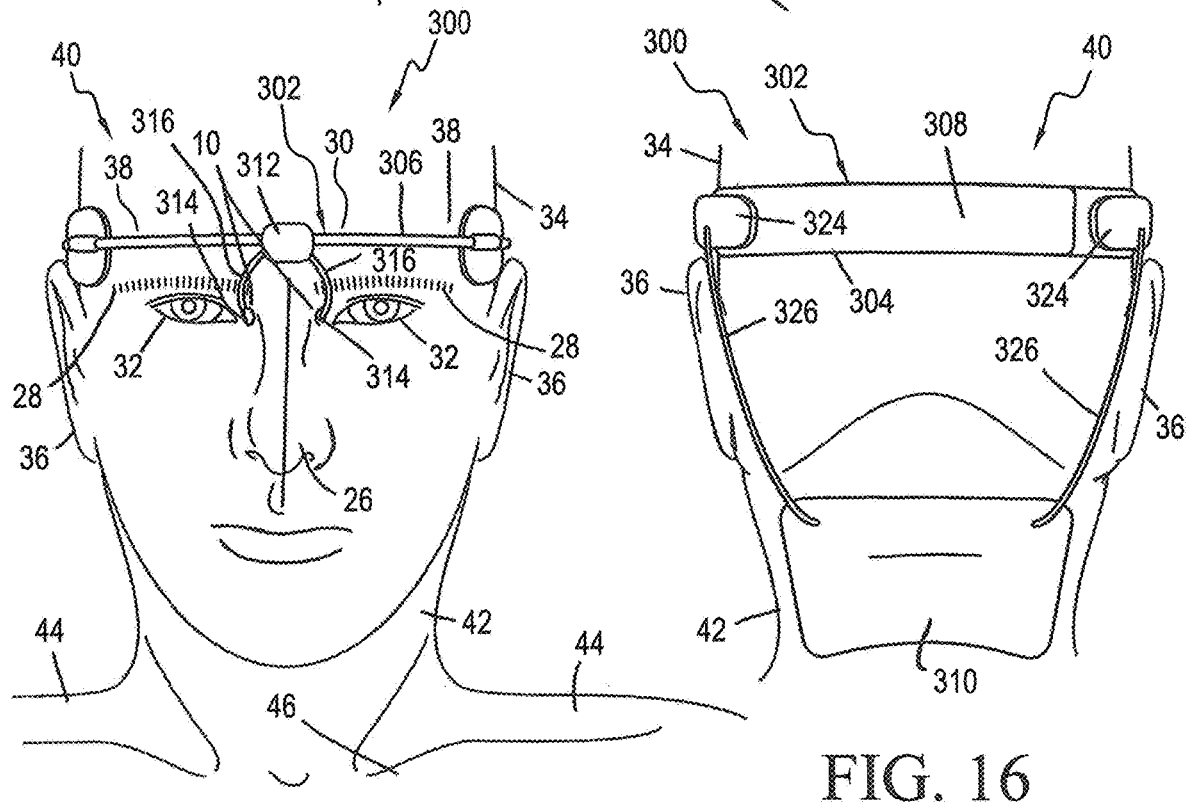
FIG. 15
FIG. 16

FIG. 23
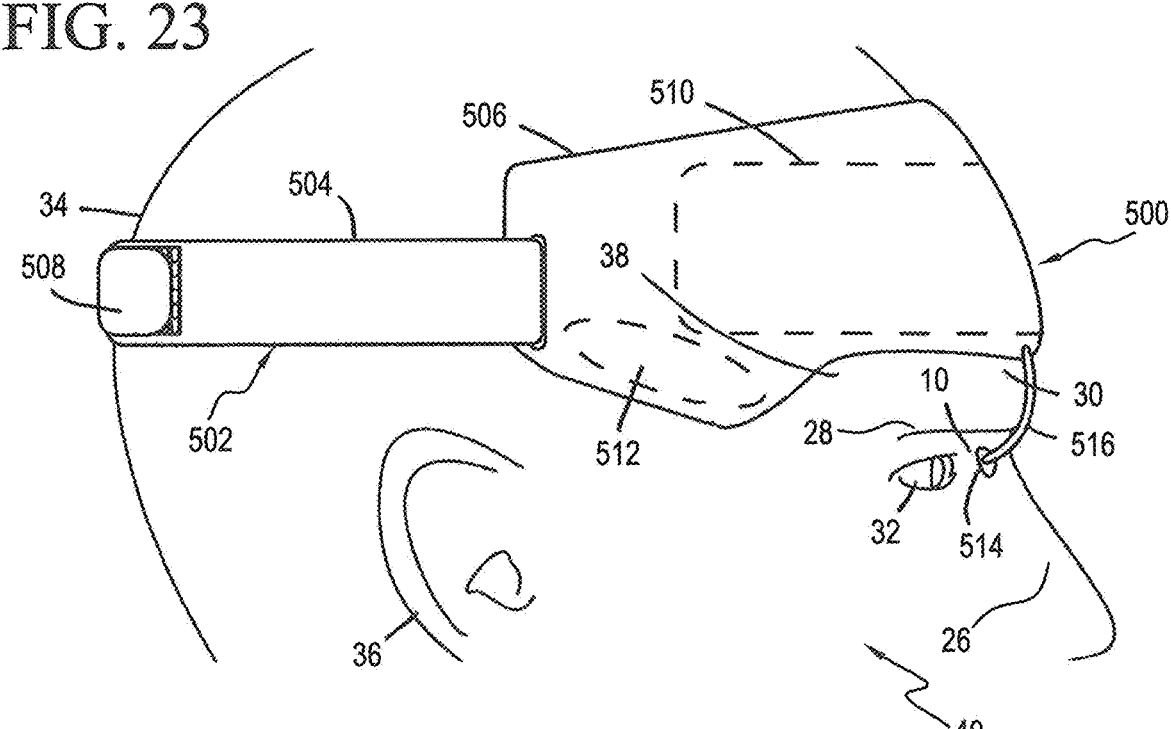
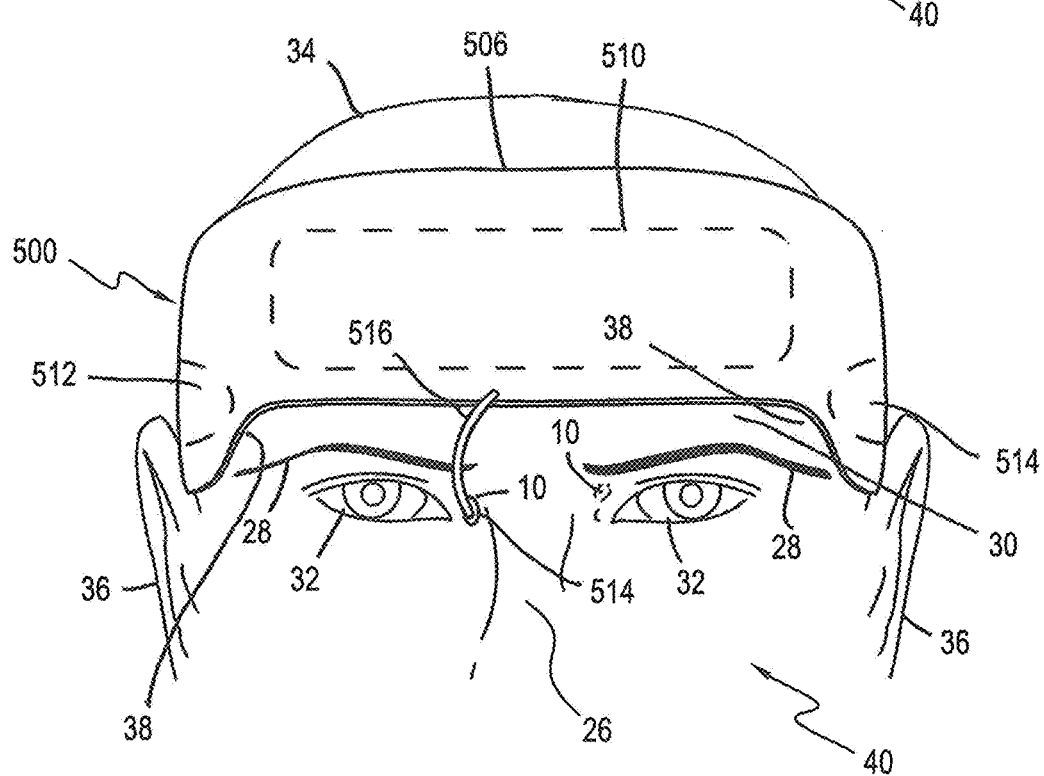
FIG. 24

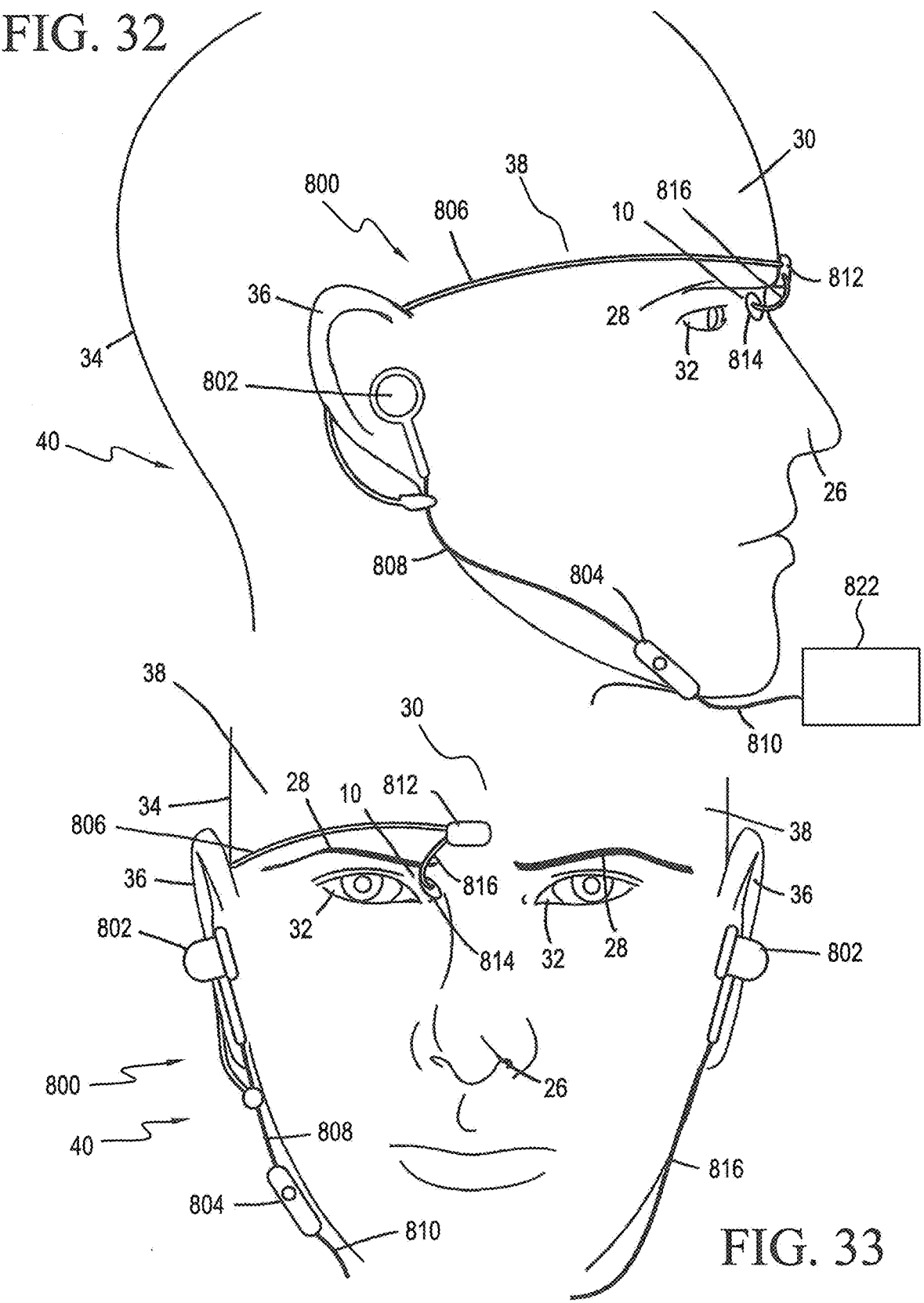

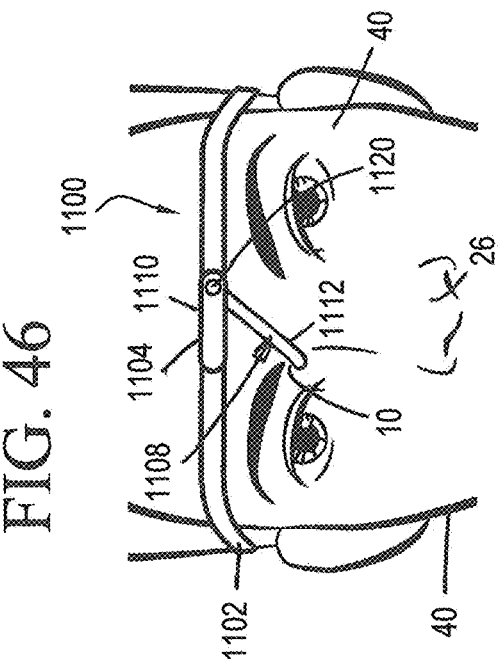
FIG. 43
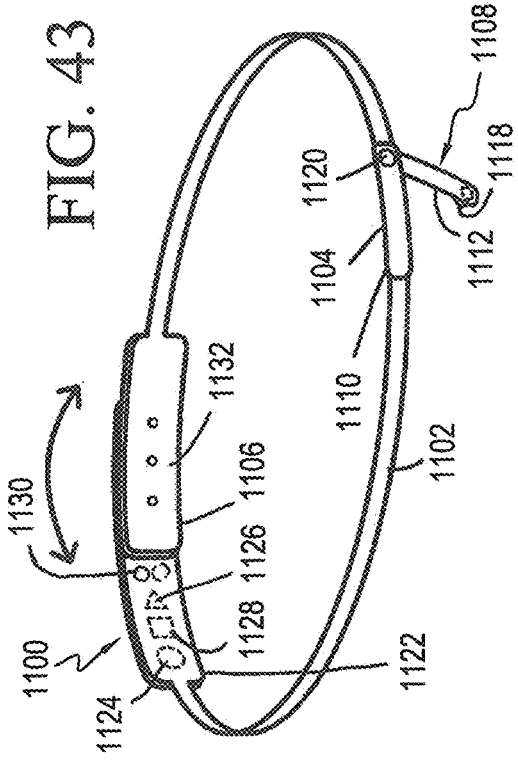
FIG. 44
FIG. 45
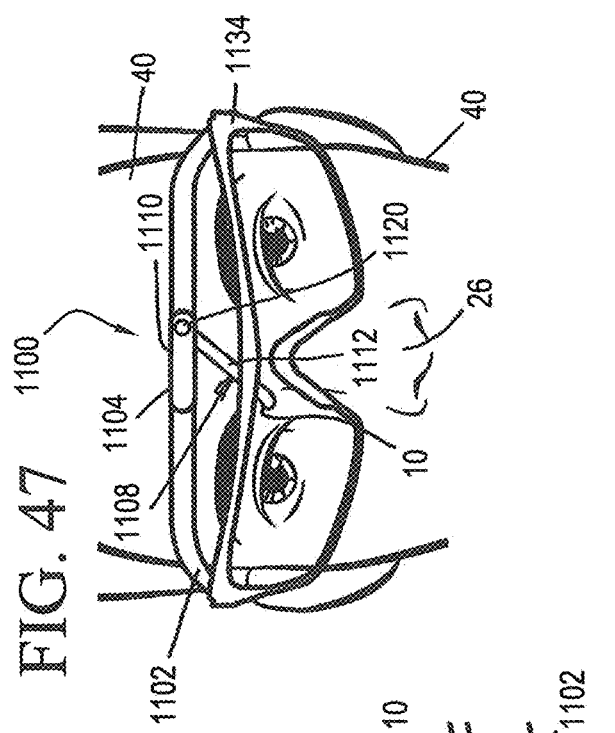
FIG. 46
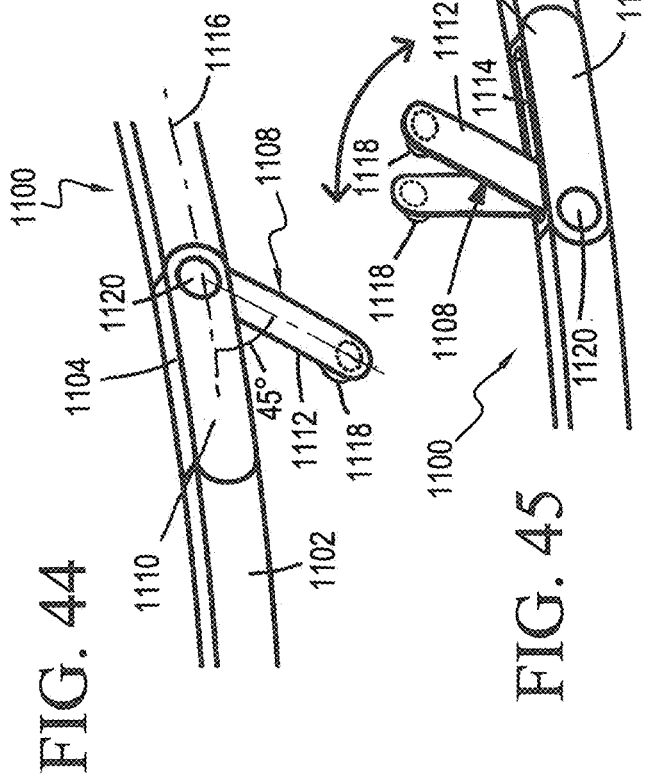
FIG. 47

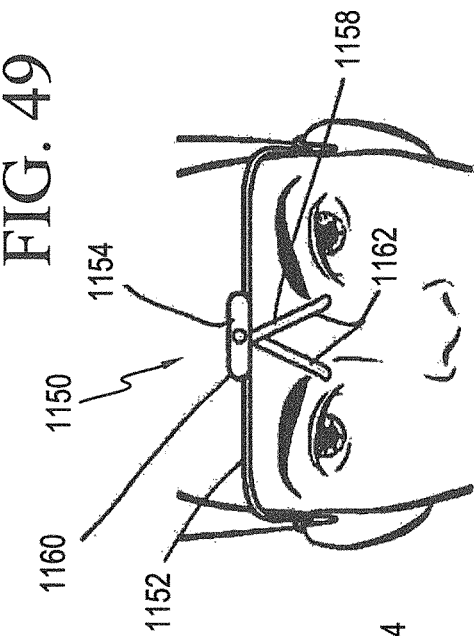
FIG. 49
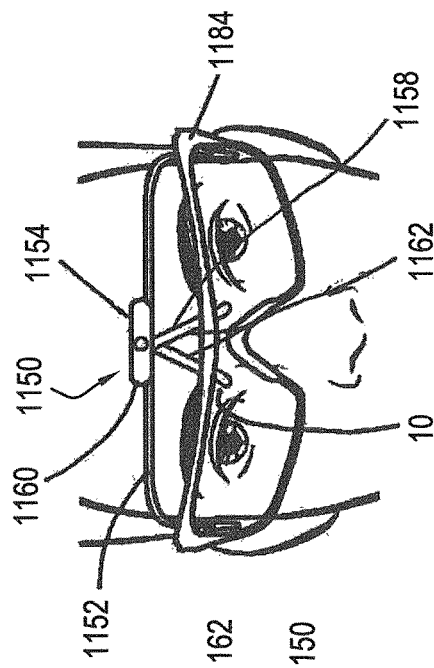
FIG. 51
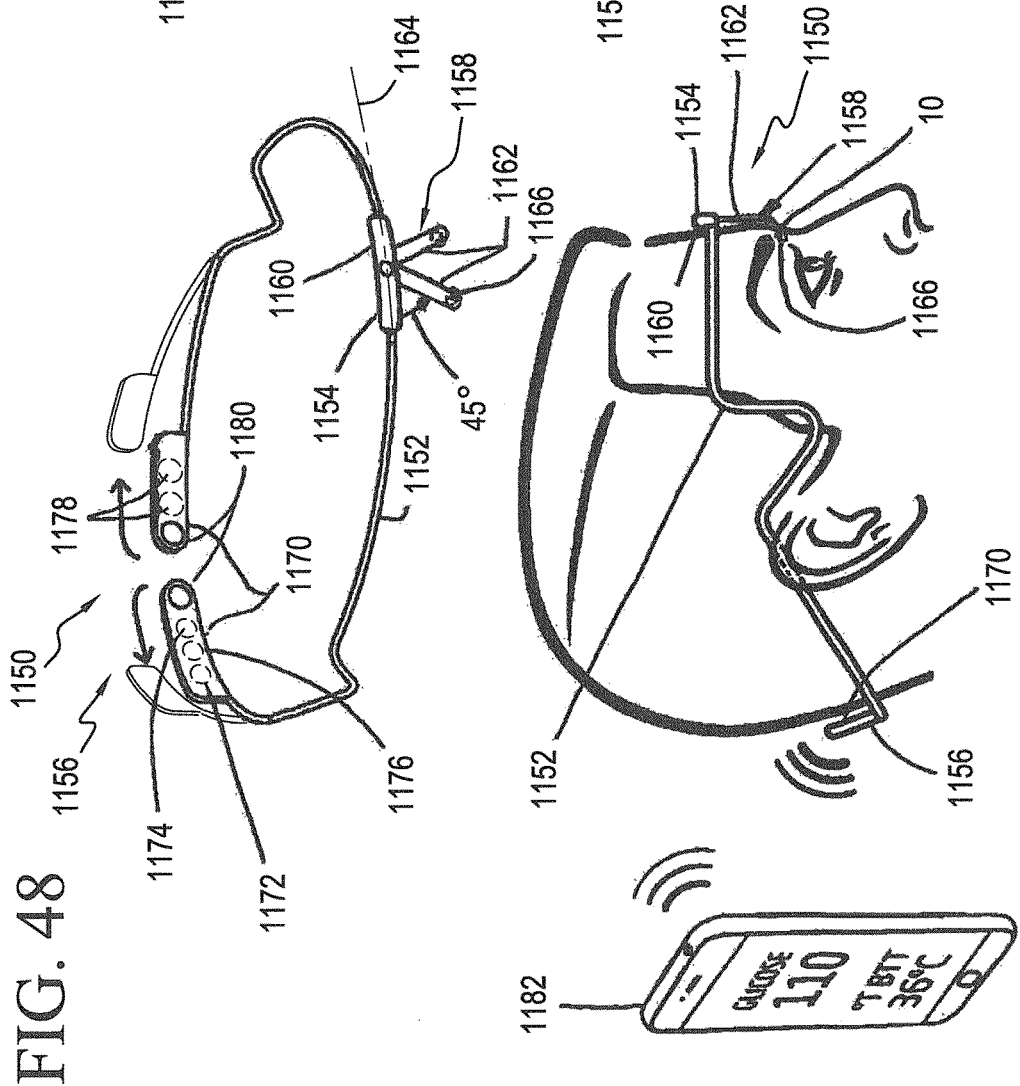
FIG. 48
FIG. 50

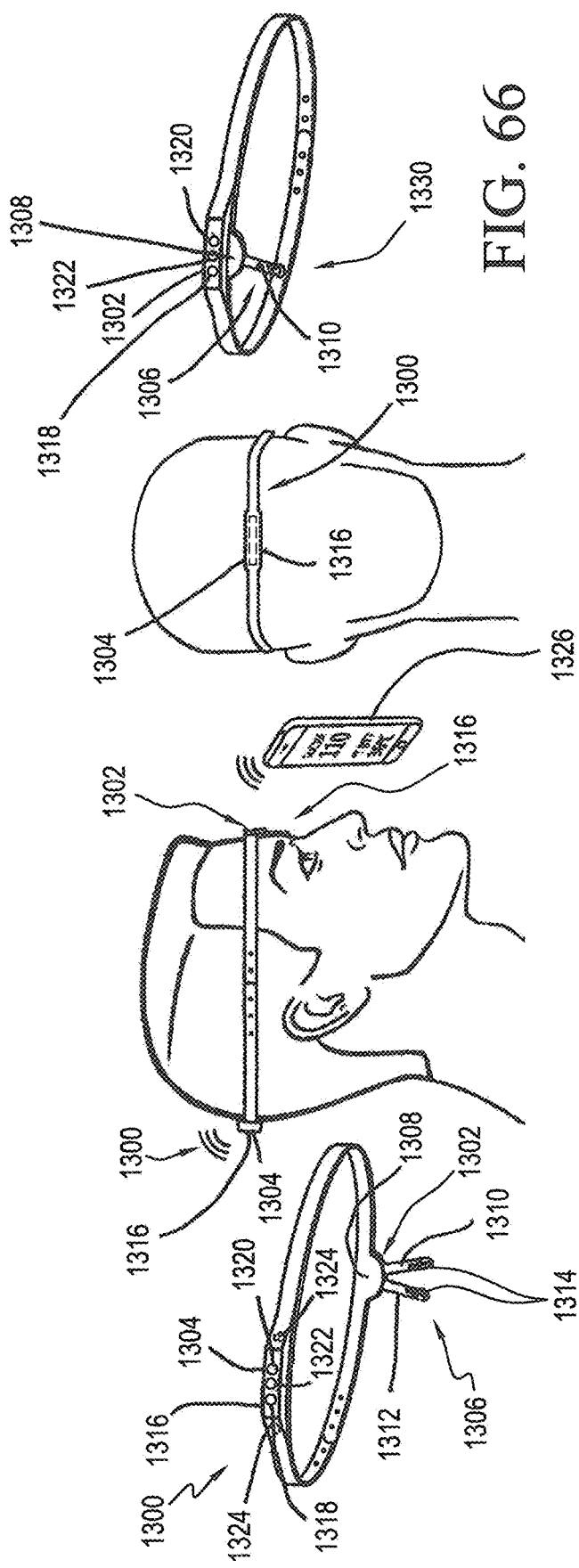

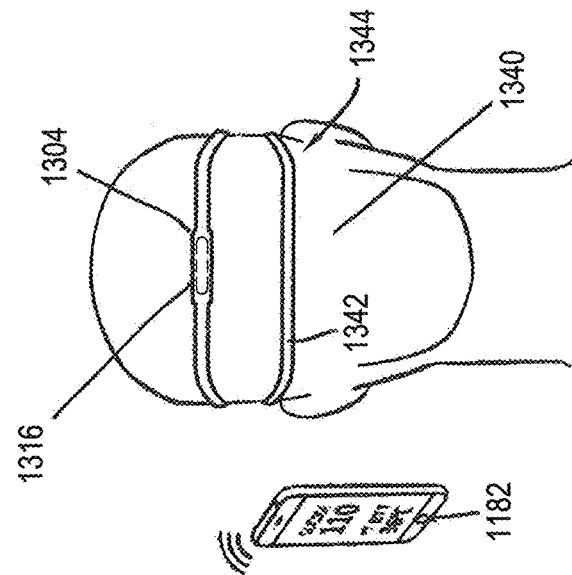
FIG. 69
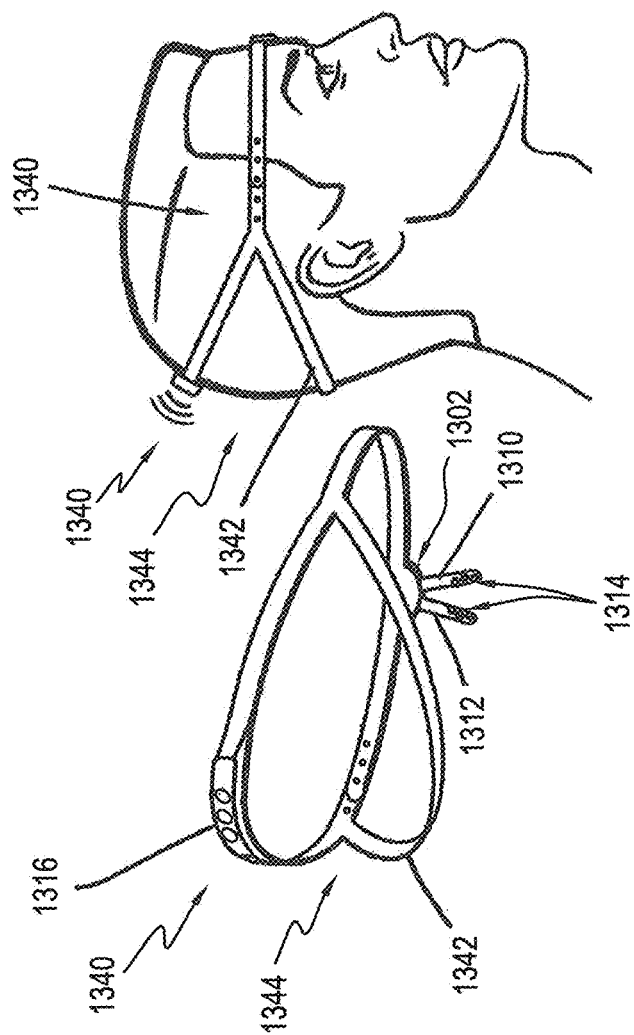
FIG. 68
FIG. 67

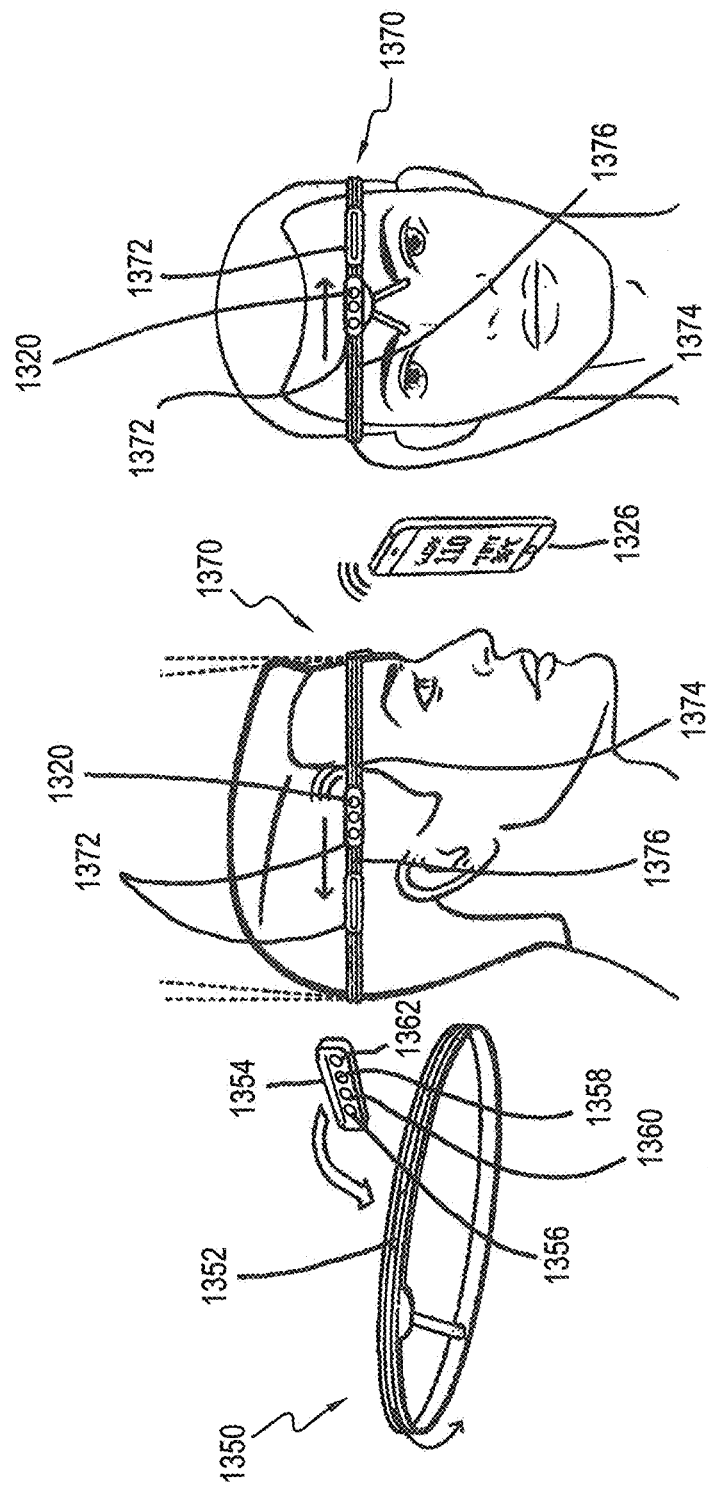

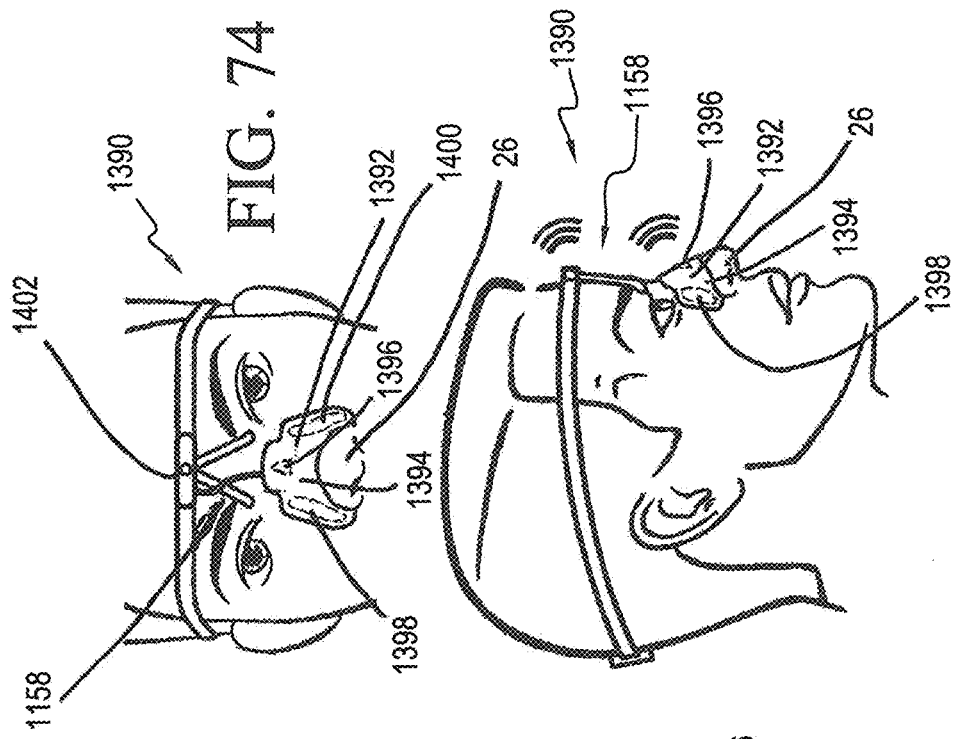
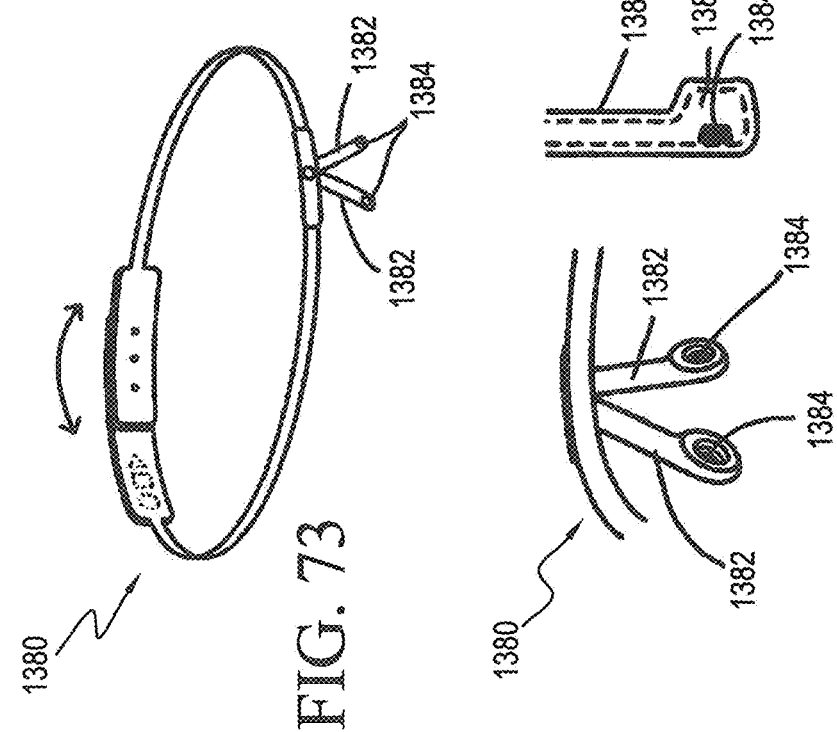

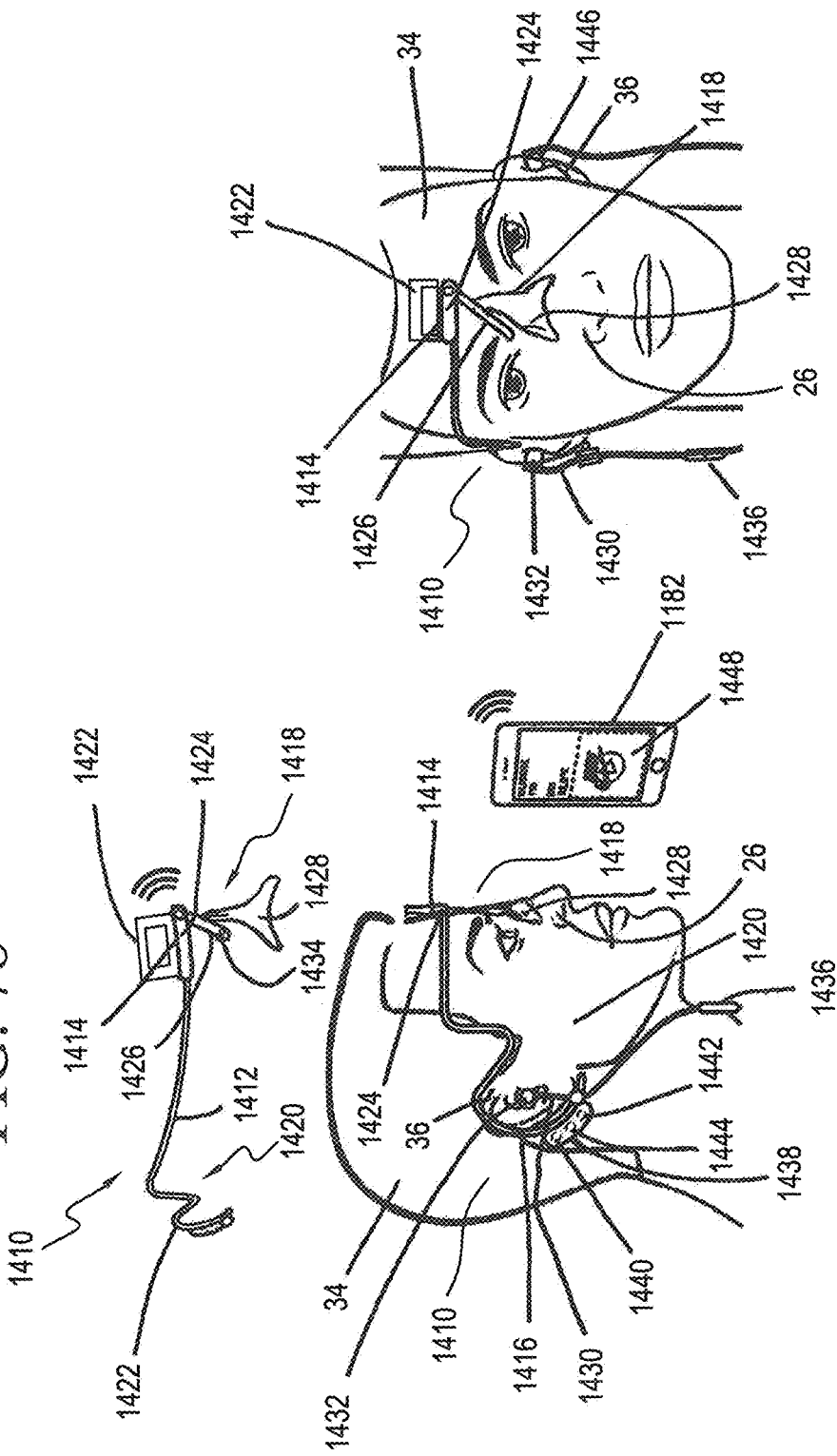

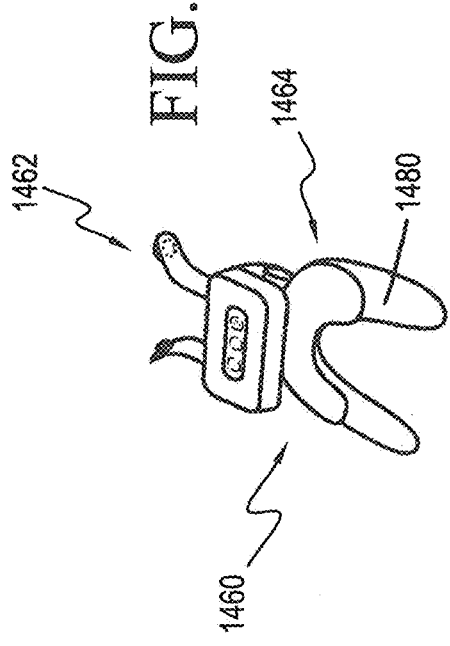
FIG. 81
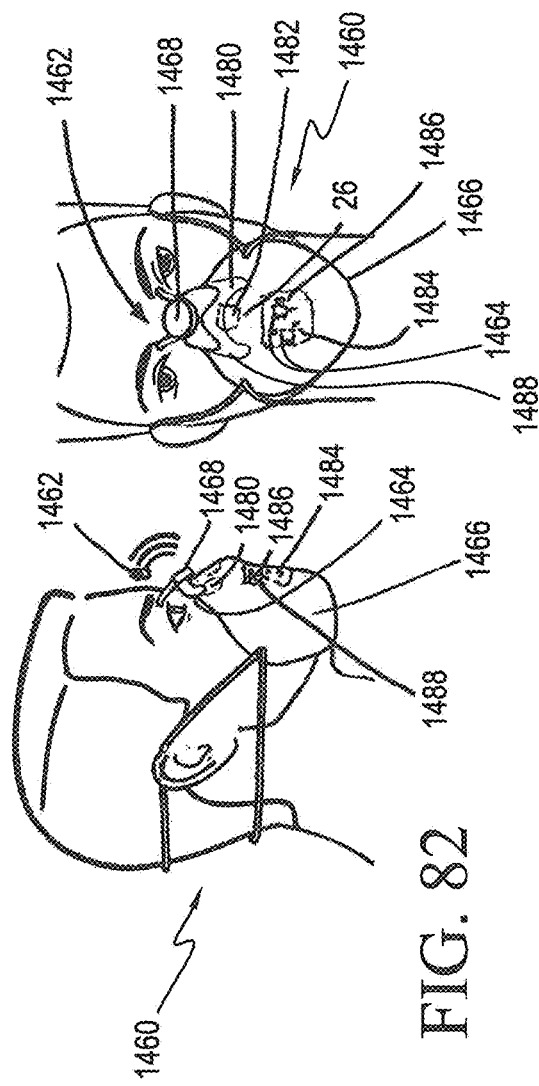
FIG. 82
FIG. 83

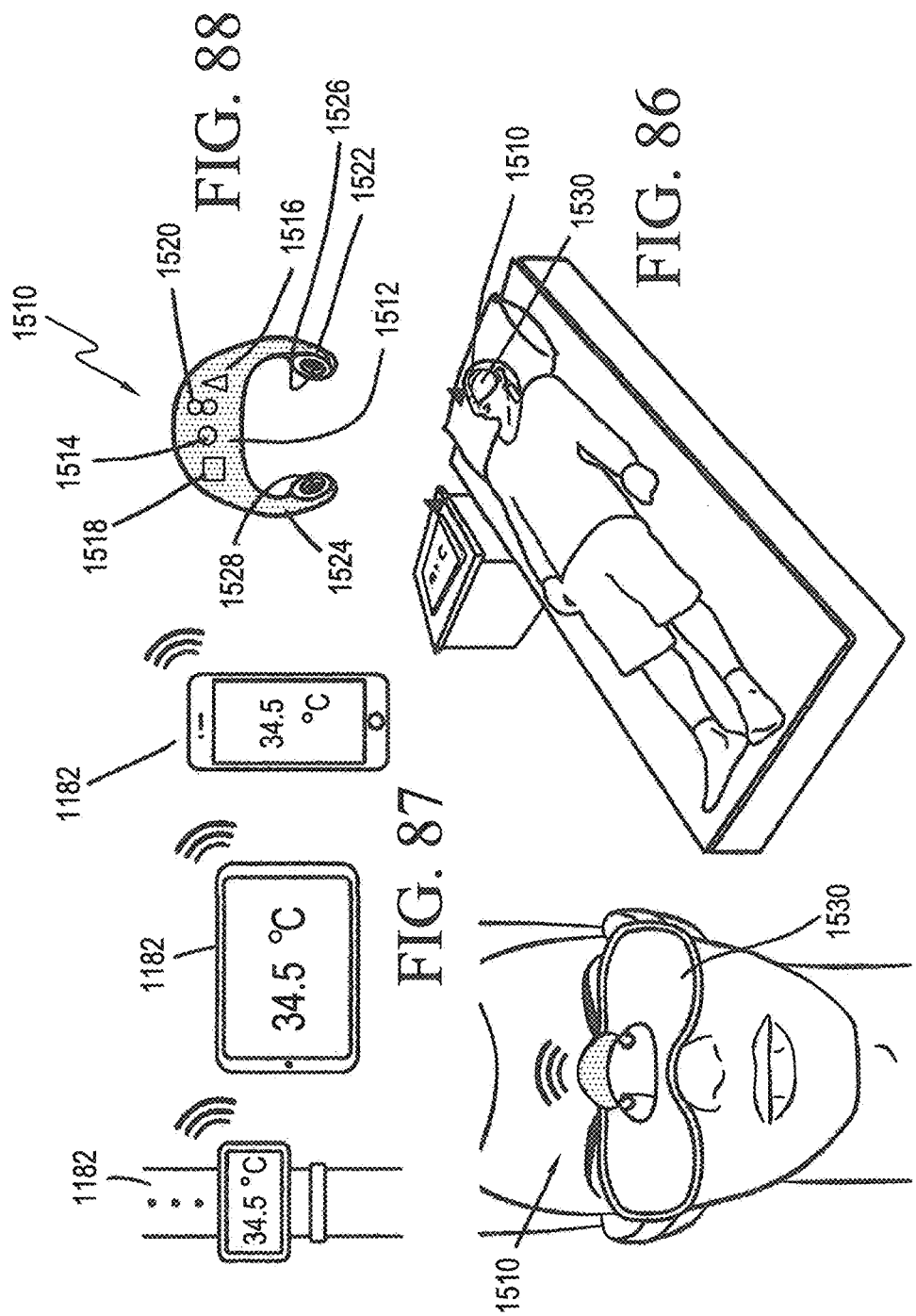

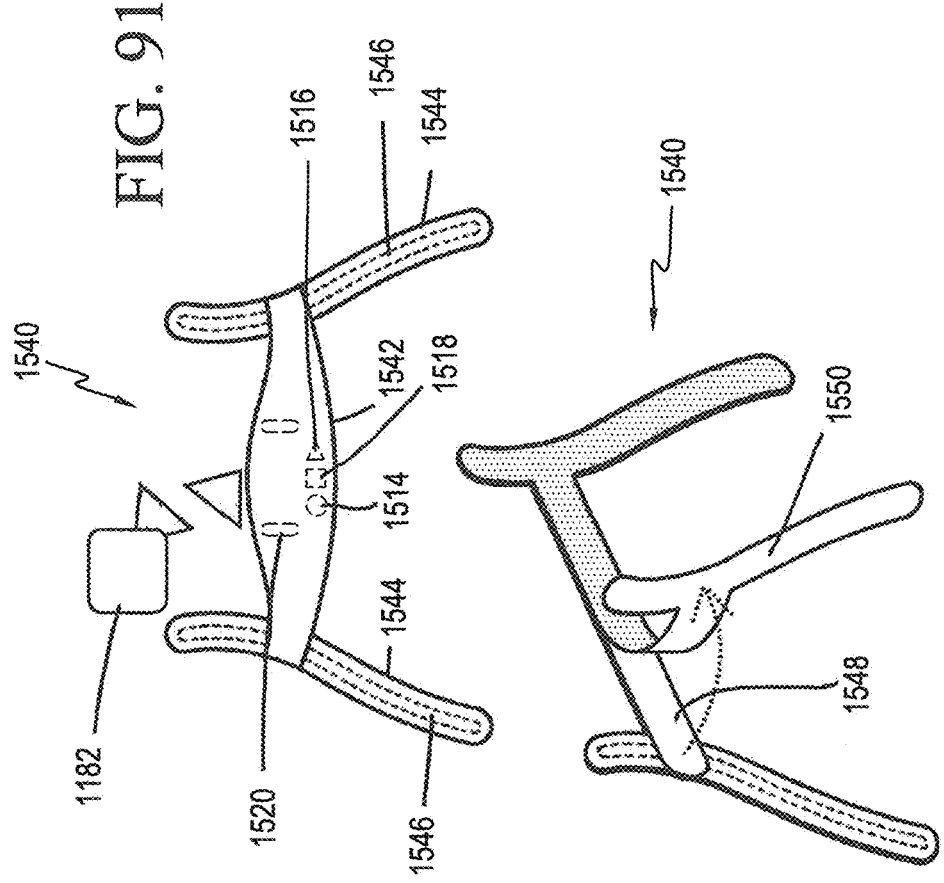

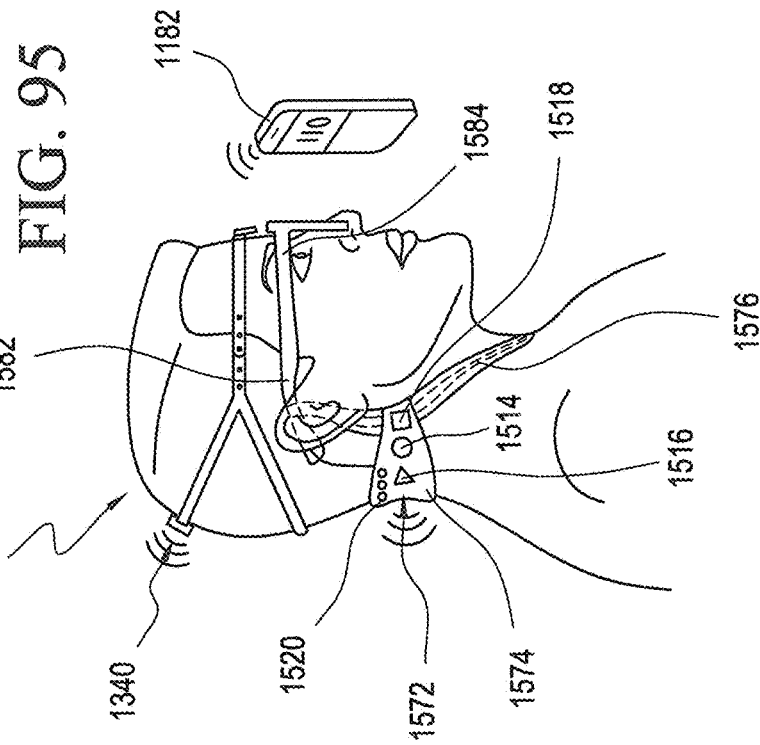
FIG. 95
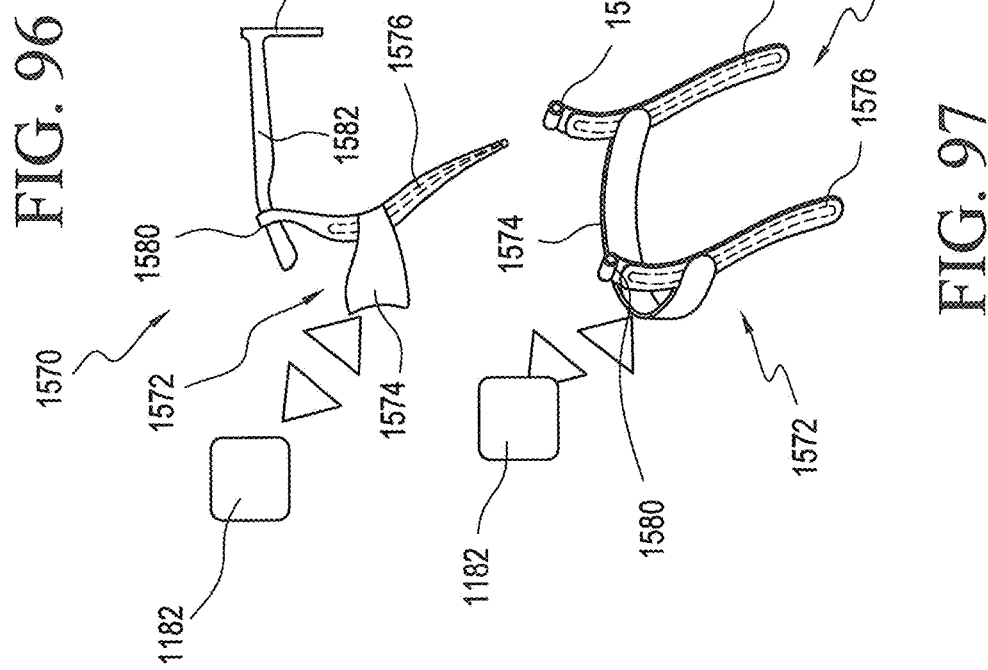
FIG. 96
FIG. 97

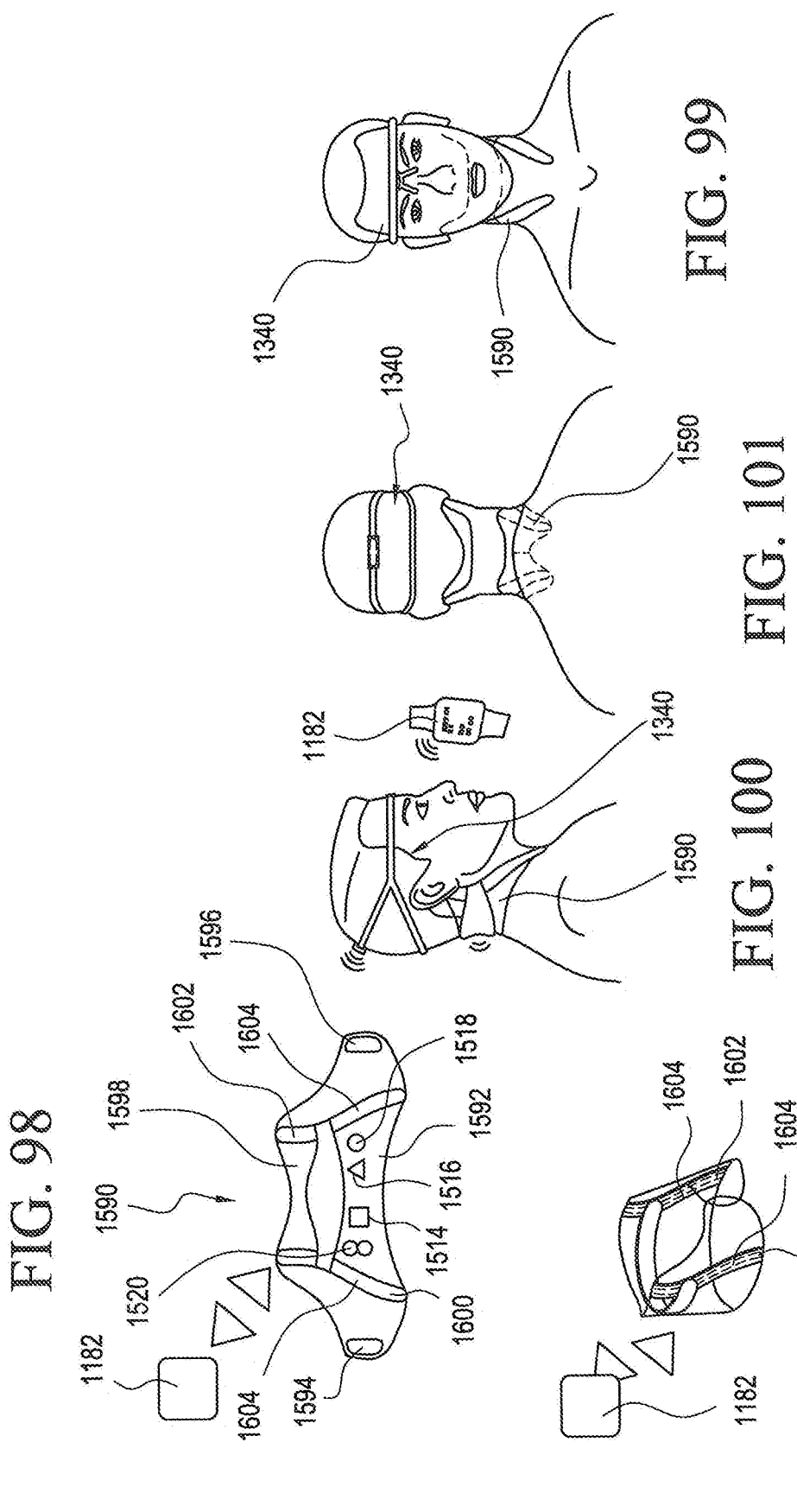

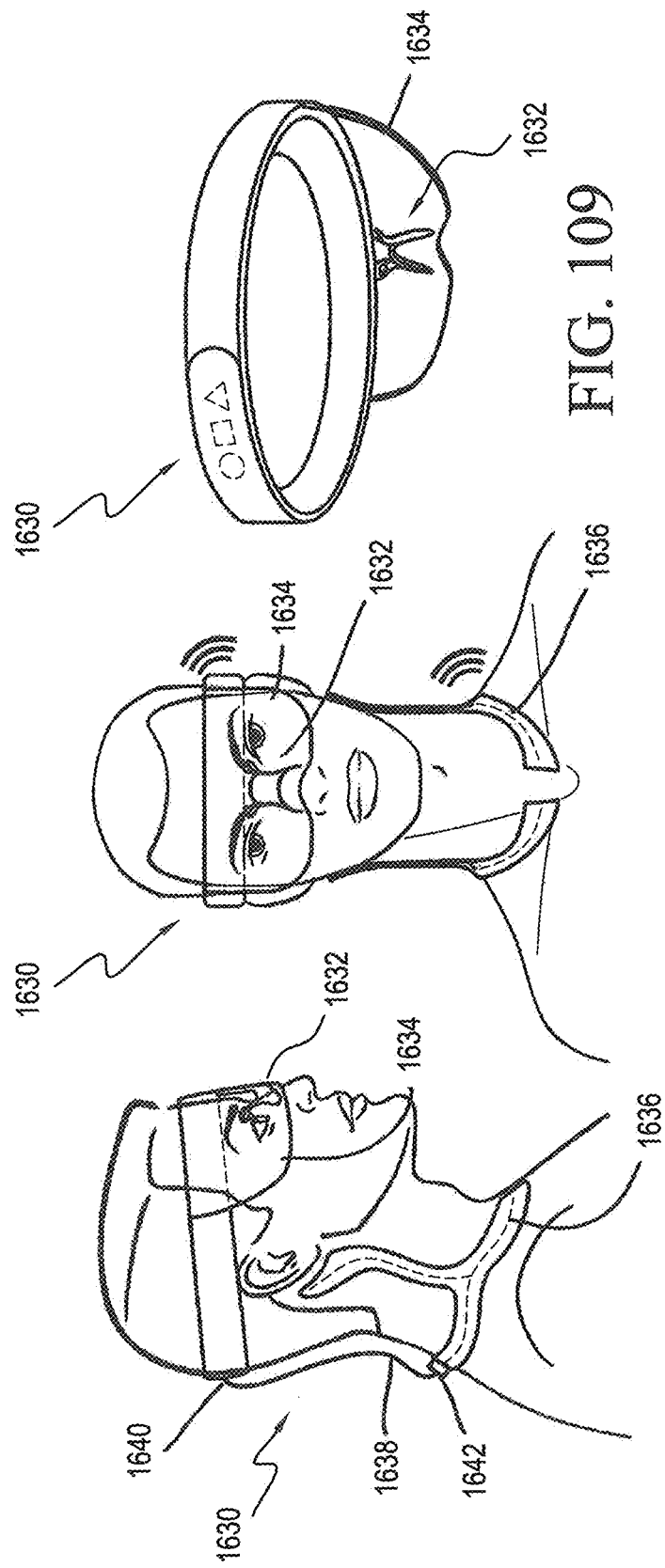

DEVICE CONFIGURED TO BE SUPPORTED ON A HUMAN BODY, TO MEASURE A BIOLOGICAL PARAMETER OF THE HUMAN BODY, AND TO CONTROL A CHARACTERISTIC OF THE HUMAN BODY

CROSS-REFERENCE TO RELATED APPLICATIONS

This application claims the benefit of priority to U.S. Provisional Patent Application No. 62/145,337, filed on Apr. 9, 2015, which is hereby incorporated by reference in its entirety.

TECHNICAL FIELD

This disclosure relates to devices configured to be supported on a human body, to measure a biological parameter of the human body, and to control a characteristic of the human body interactively.

BACKGROUND

Many devices are configured to be supported on a human body, including prescription eyeglasses, sunglasses, headphones, earbuds, clothing, headgear, backpacks, belts, etc. These devices include a conventional supporting mechanism that interfaces with one or more portions of a human head, such as a nose and an ear.

Further, devices exist to measure biological parameters of the human body, such as EEG machines, EKG machines, blood pressure cuffs, thermometers, etc.

Further yet, devices, chemicals, and methods that control a characteristic of the human body are known, such as drugs, heating pads, cooling pads, heart pacemakers, etc.

SUMMARY

This disclosure provides a device for locating an Abreu brain thermal tunnel (ABTT) and measuring thermal data from the ABTT. The device comprises a sensor or detector, a processor, and a display. The sensor is configured to acquire a thermal data of ABTT and to transmit the thermal data. The processor is configured to receive the transmitted thermal data, to analyze the thermal data to determine a location of an ABTT terminus, to then acquire thermal data from the ABTT terminus, to analyze the acquired thermal data, and to transmit the results of the analysis. The display is configured to receive the results of the analysis and to display the results of the analysis.

This disclosure also provides a device for measuring a temperature of two Abreu brain thermal tunnels (ABTT's) including a headband having two separate sensors, one right sensor and one left sensor positioned on or adjacent to the ABTT. The device comprises a rotatable member a first thermal sensor and a second thermal sensor. The first thermal sensor is positioned on the device and sized and dimensioned to measure a thermal output of a first ABTT terminus on the right side. The first thermal sensor is oriented in a first direction. The second thermal sensor is supported by the device and sized and dimensioned to measure a thermal output of a second ABTT terminus on the left side. The second thermal sensor is oriented in a second direction. The rotatable member is configured to be movable to vary the distance between the first thermal sensor and the second thermal sensor in order to align the right thermal sensor and left thermal sensor with ABTT. Processor is adapted to analyze data from the right thermal sensor and left thermal sensor and determine the highest temperature, and to display the highest temperature or alternatively to transmit the highest temperature value to a remote device This disclosure also provides a system for measuring the emission of at least one Abreu brain thermal tunnel terminus, the system comprising a sensor, a display, and a processor. The sensor is configured to receive the emissions and to transmit signals representative of the emissions during an interval of time. The processor is configured to receive the signal, to analyze the signal, and to provide an output representative of at least one of the signal and the analysis of the signal to the display. The processor is further configured to provide an output that includes an advertisement during the interval of time and during a time to receive the signal and to analyze the signal.

This disclosure also provides a method of acquiring, analyzing, and displaying data acquired from at least one Abreu brain thermal tunnel terminus. The method comprises receiving emissions from the at least one Abreu brain thermal tunnel terminus during an interval of time; transmitting signals representative of the emissions to a processor; analyzing the transmitted signals and presenting the results on a display; and displaying an advertisement during the interval of time.

This disclosure also provides a system for measuring the emission of at least one Abreu brain thermal tunnel terminus, the system comprising a sensor, a display, and a processor. The sensor is configured to receive the emissions and to transmit signals representative of the emissions during an interval of time. The processor is configured to receive the signal, to analyze the signal, and to provide an output representative of at least one of the signal and the analysis of the signal to the display. The processor is further configured to provide an output that includes an advertisement during the interval of time and during a time to receive the signal and to analyze the signal.

This disclosure also provides a system for measuring the emission of at least one Abreu brain thermal tunnel terminus, the system comprising a sensor, a display, and a processor. The sensor is configured to receive the emissions and to transmit signals representative of the emissions to a temperature modification device, the temperature modification device preferably being aligned with the carotid arteries and the vertebral arteries in the neck. The processor is configured to receive the signal, to analyze the signal, and to provide an output representative of at least one of the signal and the analysis of the signal to the temperature modification device, the temperature modification device modifying its temperature (increasing or decreasing, for heating or cooling the area covered by the temperature modification device) based on the signal received from processor. The temperature modification device is configured to provide a signal to processor of sensor device, the processor transmitting a signal to the temperature modification device creating a closed loop system, in which the temperature of the ABTT adjusts the temperature of the temperature modification device, and the processor continues to transmit a command to the temperature modification device to change its temperature (heating or cooling) until a target temperature of the ABTT is reached. The processor is further configured to provide an output that includes an advertisement during the interval of time and during a time to transmit a signal to the temperature modification device.

This disclosure also provides a system for measuring the emission of at least one Abreu brain thermal tunnel terminus connected by wired means to a temperature modification device.

This disclosure also provides a system for measuring the emission of at least one Abreu brain thermal tunnel terminus connected by wireless means to an external temperature modification device.

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 1 shows a simplified view of the ABTT and facial veins associated with the ABTT.

FIG. 2 shows a simplified partial cross-sectional view through a human skull in a vertical direction, showing the Abreu brain thermal tunnel and certain other facial features.

FIG. 14 shows a side view of a fifth apparatus in accordance with an exemplary embodiment of the present disclosure.

FIG. 15 shows a front view of the fifth apparatus of FIG. 14.

FIG. 16 shows a back view of the fifth apparatus of FIG. 14.

FIG. 23 shows a side view of a ninth apparatus in accordance with an exemplary embodiment of the present disclosure.

FIG. 24 shows a front view of the ninth apparatus of FIG. 23.

FIG. 32 shows a side view of an eleventh apparatus in accordance with an exemplary embodiment of the present disclosure.

FIG. 33 shows a front view of the eleventh apparatus of FIG. 32.

FIG. 43 shows a view of a sixteenth apparatus in accordance with an exemplary embodiment of the present disclosure.

FIG. 44 shows a view of a portion of the apparatus of FIG. 44.

FIG. 45 shows another view of a portion of the apparatus of FIG. 44.

FIG. 46 shows yet another view of the apparatus of FIG. 44 positioned on the head of the user.

FIG. 47 shows a view similar to FIG. 46 with the user also wearing an eyewear frame.

FIG. 48 shows a view of a seventeenth apparatus in accordance with an exemplary embodiment of the present disclosure.

FIG. 49 shows a view of the seventeenth apparatus of FIG. 48 positioned on the head of the user.

FIG. 50 shows yet another view of the seventeenth apparatus of FIG. 48 positioned on the head of the user.

FIG. 51 shows a further view of the seventeenth apparatus of FIG. 48 positioned on the head of the user, with the user also wearing an eyewear frame.

FIG. 63 shows a view of a twentieth apparatus in accordance with an exemplary embodiment of the present disclosure.

FIG. 64 shows another view of the twentieth apparatus of FIG. 63.

FIG. 65 shows yet another view of the twentieth apparatus of FIG. 63.

FIG. 66 shows a view of a twenty-first apparatus in accordance with an exemplary embodiment of the present disclosure.

FIG. 67 shows a view of a twenty-second apparatus in accordance with an exemplary embodiment of the present disclosure.

FIG. 68 shows another view of the twenty-second apparatus of FIG. 67.

FIG. 69 shows yet another view of the twenty-second apparatus of FIG. 67.

FIG. 70 shows a view of a twenty-third apparatus in accordance with an exemplary embodiment of the present disclosure.

FIG. 71 shows a view of a twenty-fourth apparatus in accordance with an exemplary embodiment of the present disclosure.

FIG. 72 shows another view of the twenty-fourth apparatus of FIG. 71.

FIG. 73 shows a view of a twenty-fifth apparatus in accordance with an exemplary embodiment of the present disclosure.

FIG. 74 shows a view of a twenty-sixth apparatus in accordance with an exemplary embodiment of the present disclosure.

FIG. 75 shows a view of a portion of the twenty-fifth apparatus of FIG. 73.

FIG. 76 shows another view of a portion of the twenty-fifth apparatus of FIG. 73.

FIG. 77 shows another view of the twenty-sixth apparatus of FIG. 74.

FIG. 78 shows a view of a twenty-seventh apparatus in accordance with an exemplary embodiment of the present disclosure.

FIG. 79 shows another view of the twenty-seventh apparatus of FIG. 78.

FIG. 80 shows yet another view of the twenty-seventh apparatus of FIG. 78.

FIG. 81 shows a view of a twenty-eighth apparatus in accordance with an exemplary embodiment of the present disclosure.

FIG. 82 shows another view of the twenty-eighth apparatus of FIG. 81 in addition to a temperature modification device.

FIG. 83 shows yet another view of the twenty eighth apparatus of FIG. 81 and the temperature modification device of FIG. 81.

FIG. 86 shows a view of a thirtieth apparatus in accordance with an exemplary embodiment of the present disclosure.

FIG. 87 shows another view of the thirtieth apparatus of FIG. 86 being worn with a goggle or mask.

FIG. 88 shows an enlarge view of the thirtieth apparatus of FIG. 86.

FIG. 90 shows a view of a temperature modification device in accordance with an exemplary embodiment of the present disclosure.

FIG. 91 shows another view of the temperature modification device of FIG. 90.

FIG. 95 shows a view of a thirty-second apparatus in accordance with an exemplary embodiment of the present disclosure.

FIG. 96 shows another view of the thirty-second apparatus of FIG. 95.

FIG. 97 shows a further view of the thirty-second apparatus of FIG. 95.

FIG. 98 shows a view of a temperature modification device in accordance with an exemplary embodiment of the present disclosure.

FIG. 98A shows a view of the temperature modification device in accordance with FIG. 98.

FIG. 99 shows a view of the user wearing the temperature modification device of FIG. 98 with the twenty-second apparatus of FIG. 67.

FIG. 100 shows another view of the temperature modification device of FIG. 98 and the twenty-second apparatus of FIG. 67.

FIG. 101 shows a further view of the temperature modification device of FIG. 98 and the twenty-second apparatus of FIG. 67.

FIG. 109 shows a further apparatus in accordance with an exemplary embodiment of the present disclosure.

FIG. 110 is another view of the apparatus of FIG. 109.

FIG. 111 is a further view of the apparatus of FIG. 109.

DETAILED DESCRIPTION

The Abreu brain thermal tunnel (ABTT) provides a unique opportunity to diagnose an array of conditions and diseases that were previously difficult or even possible to diagnose, and to treat those diseases and conditions, as disclosed by Applicant in U.S. patent application Ser. No. 14/512,421, filed on Oct. 11, 2014, Ser. No. 14/512,427, filed on Oct. 11, 2014, Ser. No. 14/593,848, filed on Jan. 9, 2015, Ser. No. 14/594,122, filed on Jan. 10, 2015, and Ser. No. 14/603,353, filed on Jan. 22, 2015, incorporated herein by reference in their entirety. The present disclosure provides further apparatuses, devices, and mechanisms for the diagnosis of conditions and diseases via a terminus of the ABTT, and treatment of those conditions and diseases.

Diagnosis and treatment of human conditions, such as heatstroke, hypothermia, cancer, heart attack, seizures, stroke, and the like, are conventionally conducted using a plurality of tests and treatments that are often time consuming and expensive. Sometimes the diagnosis of a condition is based on observation, such as a heatstroke, where observation of a heatstroke is the only indication that a heatstroke is taking place. Similarly, treatment can be time consuming and often fails to focus on the root cause of a condition. Even worse, treatment is often the cause of additional problems due to the invasive nature of some treatments or the side effects of some treatments.

Figure 3:
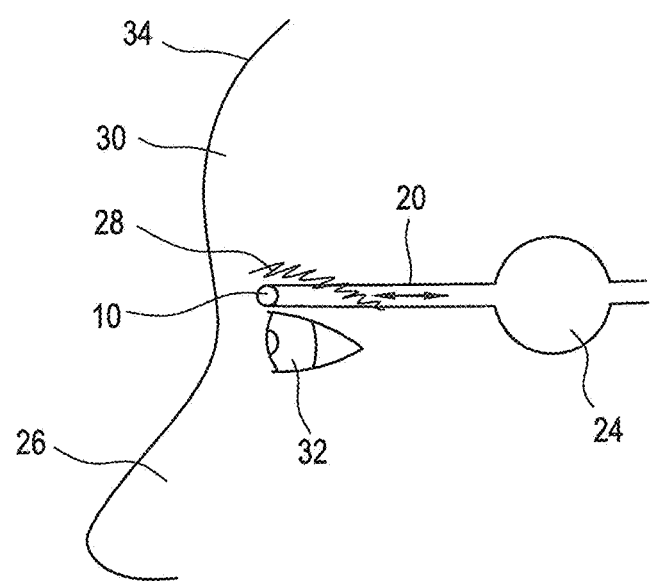
FIG. 3 shows a stylized representation of the flow of blood into a brain core.
Figure 4:
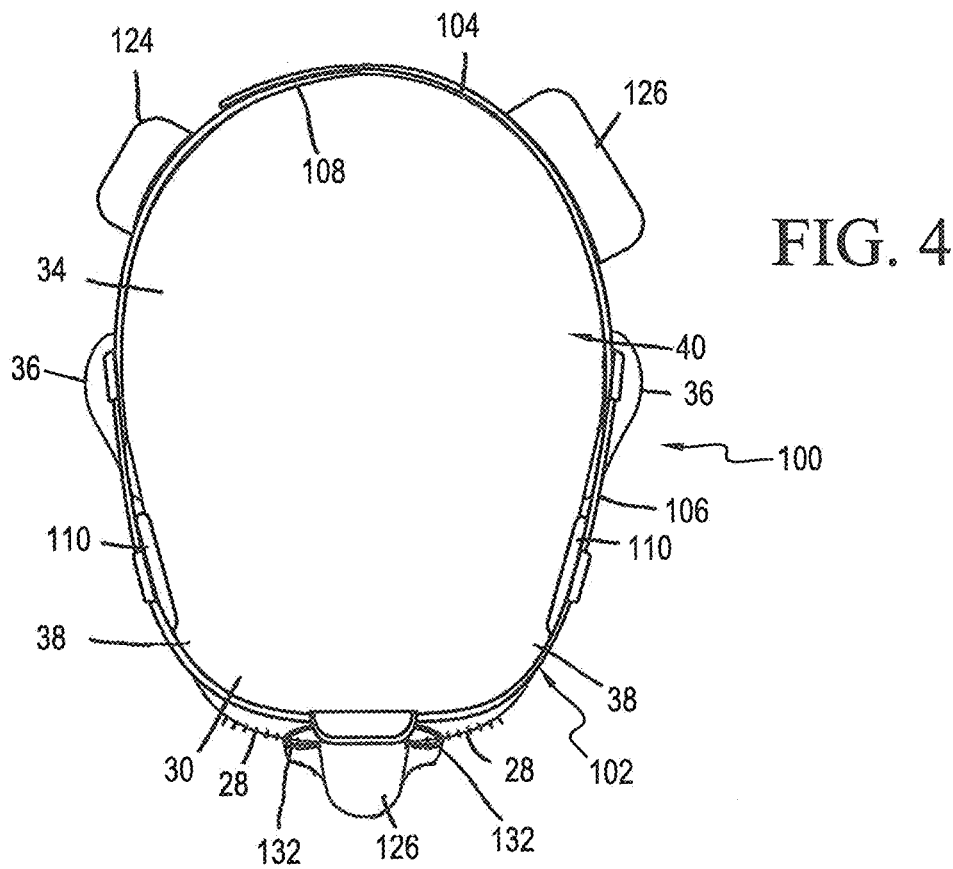
FIG. 4 shows a top view of a first apparatus in accordance with an exemplary embodiment of the present disclosure.
Figure 5:
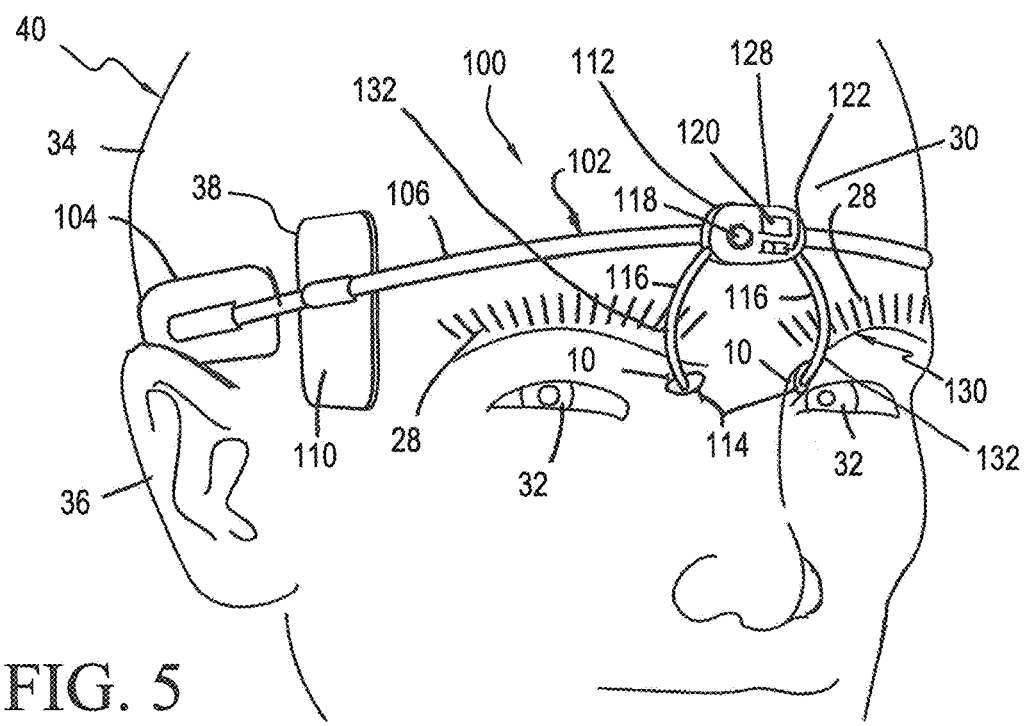
FIG. 5 shows a perspective view of the first apparatus of FIG. 4.
Figure 6:
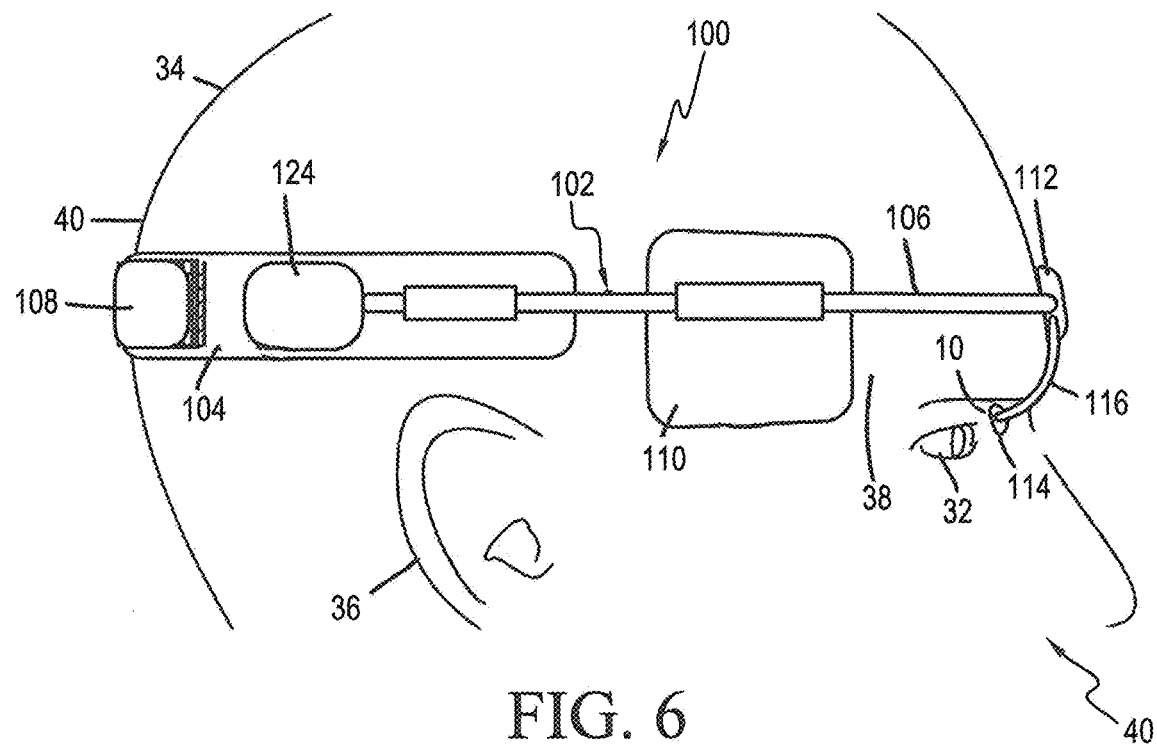
FIG. 6 shows a side view of the first apparatus of FIG. 4.
Figure 7:
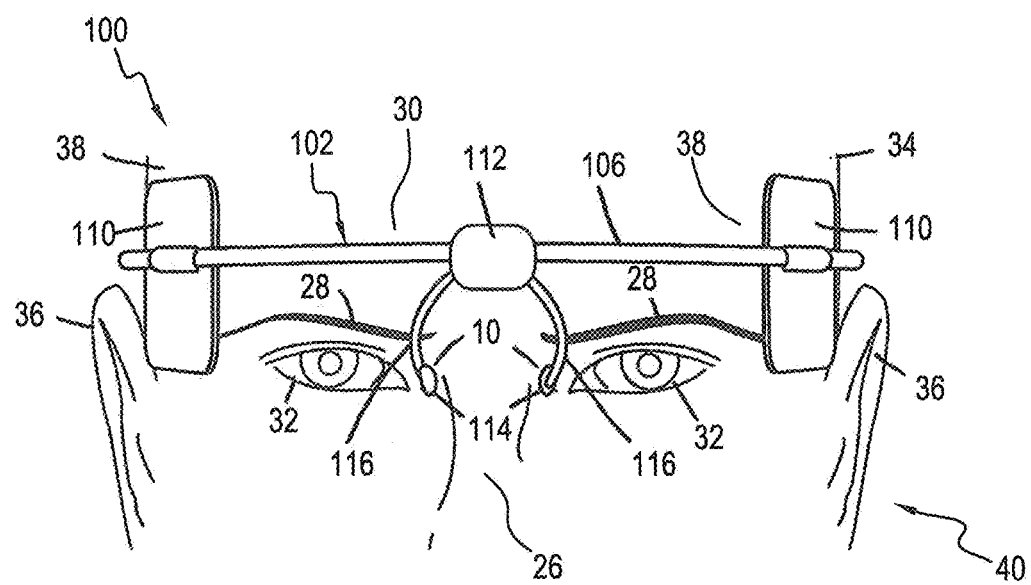
FIG. 7 shows a front view of the first apparatus of FIG. 4.

The present disclosure arises from the discovery that the Abreu brain thermal tunnel, or ABTT, provides the first known structure for brain-surface thermodynamic communication and thermal connection directly with the center of the brain. Anatomically and physiologically speaking, and as shown in FIGS. 1-3, ABTT 12 includes a continuous, direct, and undisturbed connection between a brain core 24 at the control center of the brain and the skin of ABTT terminus 10. The skin of ABTT terminus 10 is unique in that it is the thinnest skin with the fewest layers, it is absent a fat layer, and it has the high thermal conductivity of any skin on the human body.

The physical and physiological events at one end of the tunnel are reproduced at the opposite end. Thus, ABTT 12 enables the direct transfer of temperature signals from brain core 24 to ABTT terminus 10 without significant barriers, as described in co-pending U.S. patent application Ser. No. 14/512,421. Furthermore, modification of temperature at ABTT terminus 10, including application of heat and removal of heat, directly affects brain core 24, and ultimately, the entire body of the patient or subject. Accordingly, the present disclosure includes descriptions of apparatuses for acquiring temperature signals from ABTT terminus 10, analyzing those signals, and determining a human condition from those signals. In addition, apparatuses for the treatment of human conditions can be combined with temperature acquisition apparatuses, as disclosed herein.

Anatomy shows the convergence of four veins at ABTT target area 10: frontal 14, superior palpebral 16, supraorbital 18, and angular 20. As angular vein 20 extends further from ABTT 12, it transitions into facial vein 22. Having converged, there is a direct, valve-free connection from ABTT target area 10 between an eye 32 and an eyebrow 28 into the center of the brain, which is the temperature center present in the hypothalamus or thermal storage area of the body present in the cavernous sinus.

FIGS. 1 and 2 show the approximate location of these veins in relation to other facial features. Angular/facial vein 20/22 runs up alongside nose 26, superior palpebral vein 16 runs along eyebrow 28, and frontal vein 14 and supraorbital vein 18 run through forehead 30, all positioned on a head 34. For the purposes of disclosure, terminology referring to relevant facial areas or veins herein will be described as one or more of the above-referenced veins and ABTT target area 10.

As described herein, veins 14, 16, 18, 20, and 22 converge in the superomedial orbit in the region of the upper eyelid and adjacent to the bridge of the nose, and flow directly, without inhibition, to the center of the brain. The skin in this area, as shown in pending application by Applicant, is the thinnest skin in the body and free of fat, providing an unexpectedly rapid communication of temperature from the brain core to the skin of ABTT terminus 10. These vessels lack valves, which are typically an important barrier to blood flow and the direct and rapid transmission of temperature signals. Without valves, these blood vessels truly provide a direct, uninhibited passage for transporting temperature signals directly to and from the hypothalamic region of the brain. Moreover, ABTT 12 includes a superior ophthalmic vein (SOV) 23, which connects the skin surface to the brain and corresponds to the central portion of the tunnel (ABTT 12), is valveless, and has bidirectional blood flow. The SOV lies directly underneath the skin of the superomedial orbit, between eye 32 and eyebrow 28, and is a direct conduit from the surface of the skin at the facial end of ABTT 12 to the brain, and then to the hypothalamus. The hypothalamic region of the brain is the link between the central nervous system and the endocrine system and, as such, acts as the center of control for many basic bodily functions such as, for example, hunger, thirst, body temperature, fatigue, blood pressure, immune responses, circadian cycles, hormone production and secretion, and many others.

The facial end of ABTT 12, herein referred to as a target area, or terminus 10 on the skin on, over, or adjacent to ABTT 12, measures about 11 mm in diameter measured from the medial corner of eye 32 at the medial canthal tendon and extends superiorly for about an additional 6 or 7 mm in the form of an ABTT superior projection, and then extends into an upper eyelid in a horn-like projection for another 22 mm. Fat is absent in ABTT terminus 10 and in ABTT horn-like projections near to ABTT terminus 10, with a fat layer present in areas a spaced distance away from ABTT terminus 10.

Many aspects of the disclosure are described in terms of sequences of actions to be performed by elements of a computer system or other hardware capable of executing programmed instructions, for example, a general-purpose computer, special purpose computer, workstation, or other programmable data process apparatus. It will be recognized that in each of the embodiments, the various actions could be performed by specialized circuits (e.g., discrete logic gates interconnected to perform a specialized function), by program instructions (software), such as program modules, being executed by one or more processors (e.g., one or more microprocessors, a central processing unit (CPU), and/or application specific integrated circuit), or by a combination of both. For example, embodiments can be implemented in hardware, software, firmware, microcode, or any combination thereof. The instructions can be program code or code segments that perform necessary tasks and can be stored in a non-transitory machine-readable medium such as a storage medium or other storage(s). A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents.

The non-transitory machine-readable medium can additionally be considered to be embodied within any tangible form of computer readable carrier, such as solid-state memory, magnetic disk, and optical disk containing an appropriate set of computer instructions, such as program modules, and data structures that would cause a processor to carry out the techniques described herein. A computer-readable medium may include the following: an electrical connection having one or more wires, magnetic disk storage, magnetic cassettes, magnetic tape or other magnetic storage devices, a portable computer diskette, a random access memory (RAM), a read-only memory (ROM), an erasable programmable read-only memory (e.g., EPROM, EEPROM, or Flash memory), or any other tangible medium capable of storing information. It should be noted that the system of the present disclosure is illustrated and discussed herein as having various modules and units that perform particular functions.

It should be understood that these modules and units are merely described based on their function for clarity purposes, and do not necessarily represent specific hardware or software. In this regard, these modules, units and other components may be hardware and/or software implemented to substantially perform their particular functions explained herein. The various functions of the different components can be combined or segregated as hardware and/or software modules in any manner, and can be useful separately or in combination. Input/output or I/O devices or user interfaces including, but not limited to, keyboards, displays, pointing devices, and the like can be coupled to the system either directly or through intervening I/O controllers. Thus, the various aspects of the disclosure may be embodied in many different forms, and all such forms are contemplated to be within the scope of the disclosure.

FIGS. 4-7 show a first apparatus in accordance with an exemplary embodiment of the present disclosure, indicated generally at 100. Apparatus 100 is configured to be positioned and at least partially supported on forehead 30 of head 34 in a location that is above eyebrows 28 and ears 36. Apparatus 100 is configured to include a support apparatus 102, which is configured to include a securing strap 104 and a support strap 106. Securing strap 104 is further configured with a device or mechanism to secure apparatus 100 to head 34. For example, securing strap 104 can be configured as an elastic strap that stretches to permit apparatus 100 to be positioned on and secured to head 34. In another embodiment, securing strap 104 can be configured to include a fastening apparatus 108, such as a buckle arrangement, or a hook and loop fastening apparatus.

Support apparatus 102 is configured to locate and position a plurality of elements, such as one or more temperature modification devices 110, which can be, for example, heating pads, thermoelectric devices, resistive devices, etc., configured and positioned to contact an associated temple 38 of head 34 to provide heating and/or cooling of head 34, a control device 112, a power supply 124 configured to provide power to the electrically operated elements of apparatus 100, and a monitoring device 126, which can include a display, audible output, or the like, to provide information to a person other than subject or patient 40, who can also be a user. Control device 112, which is positioned at a center 128 is configured to support one or more temperature sensors 114, configured to be positioned on ABTT terminus 10 and which can be connected to control device 112 by flexible, movable, or positionable supports 116. Control device 112 can be configured to include one or more control features, such as a power/control switch 118, a display 120, and one or more input or adjustment controls 122. Specialized sensors 114 supported by center 128 of support apparatus 102, which can be described as a headband, are part of a sensor assembly 130. Sensor assembly 130 includes one or more arms 132. Each sensor 114 is disposed along a corresponding arm 132 or at a distal end of corresponding arm 132. When receiving signals from ABTT terminus 10, sensor 114 is positioned between one eye 32 and a corresponding eyebrow 28. Although two sensors 114 are shown, it should be understood that only one sensor 114 can be used, and it is within the scope of the invention.

In operation, apparatus 100 reads the temperature of ABTT terminus 10 by way of sensors 114. Control device 112 determines whether a condition exists that requires temperature modification of a subject or patient 40. If such treatment is required, as determined either by control device 112 or a separate electronic device (not shown) that communicates with control device 112, one or more temperature modification devices 110 are actuated to provide heating and/or cooling, preferably of right temple 38 and left temple 38, with continuous and simultaneous monitoring of the temperature of ABTT terminus 10. The temperature modification continues until the temperature at ABTT terminus 10 reaches a desired value, or until a predetermined time interval passes.

Figure 8:
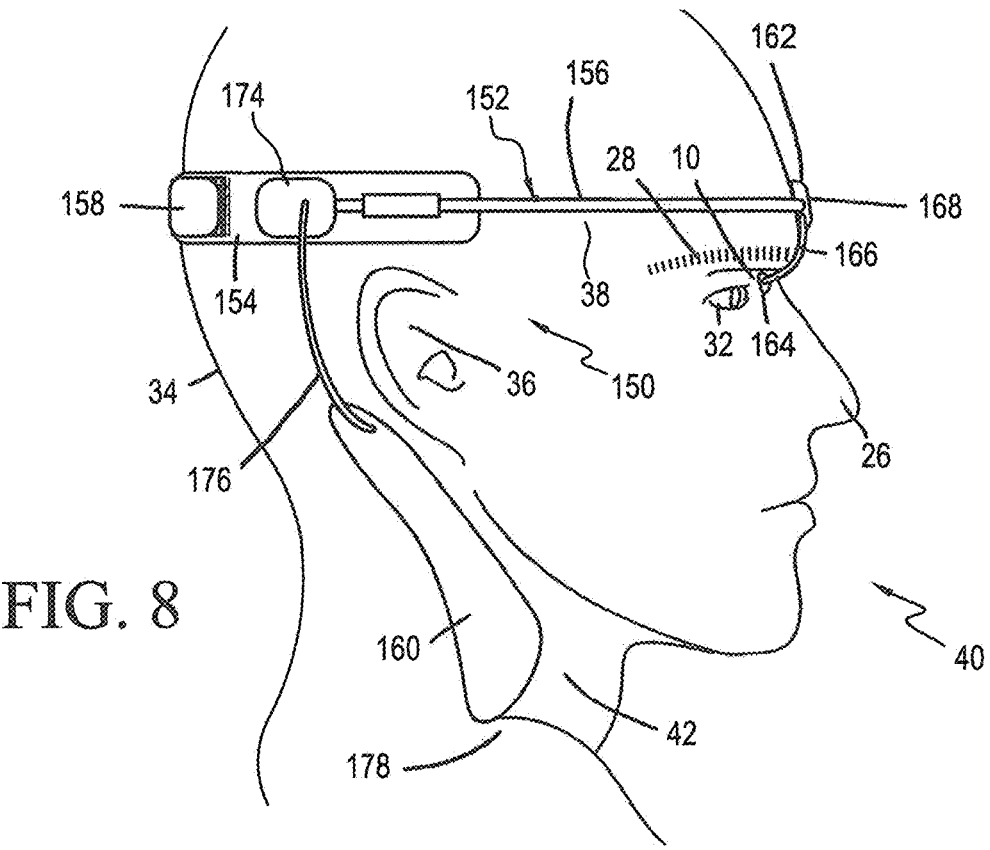
FIG. 8 shows a side view of a second apparatus in accordance with an exemplary embodiment of the present disclosure.
Figure 9:
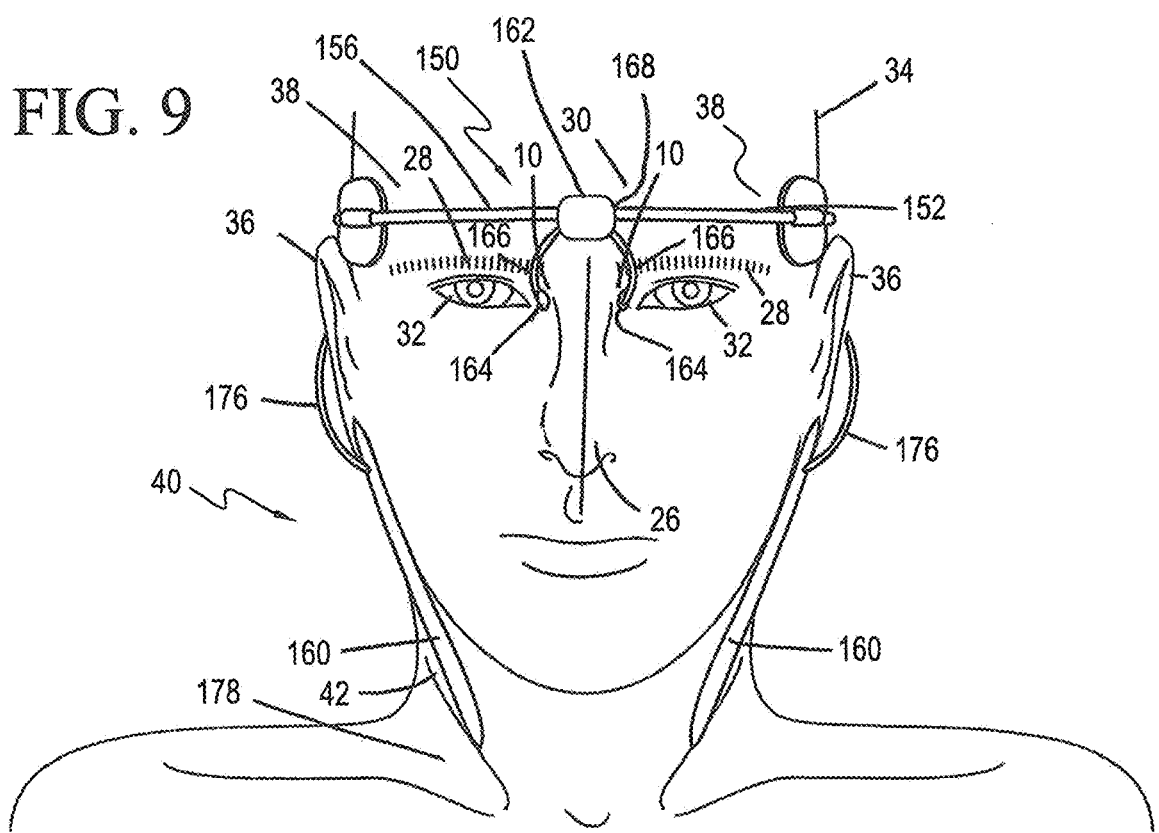
FIG. 9 shows a front view of the second apparatus of FIG. 8.

FIGS. 8 and 9 show a second apparatus in accordance with an exemplary embodiment of the present disclosure, indicated generally at 150. Apparatus 150 is configured to be positioned on forehead 30 of head 34 in a location that is above eyebrows 28 and ears 36. Apparatus 150 is configured to include a support apparatus 152, which is configured to include a securing strap 154 and a support strap 156. Securing strap 154 is further configured with a device or mechanism to secure apparatus 100 to head 34. For example, securing strap 154 can be configured as an elastic strap that stretches to permit apparatus 150 to be positioned on and secured to head 34. In another embodiment, securing strap 154 can be configured to include a fastening apparatus 158, such as a buckle arrangement, or a hook and loop fastening apparatus.

Support apparatus 152, which can be described as a headband, supports and positions a plurality of elements, such as a control device 162, and a power supply/control system 174 that supplies power to the electrically operated elements of apparatus 150 as well as controls elements of apparatus 150, as modified by input to, for example, control device 162. Control device 162 is positioned at a center 168 of apparatus 150. Control device 162 supports one or more specialized temperature sensors 164, which are configured to be positioned on ABTT terminus 10 between eye 32 and a corresponding eyebrow 28. Temperature sensors 164 are connected to control device 162 by flexible, movable, or positionable supports or arms 166. Control device 162 can be configured to include one or more control features, such as those shown in FIG. 5. Although two sensors are shown, it should be understood that only one sensor can be used, and it is within the scope of the invention.

Apparatus 150 also includes one or more temperature modification devices 160, which can be, for example, heating pads, thermoelectric devices, resistive devices, thermally retentive materials, etc. Temperature modification devices 160 include dimensions and a configuration that mate devices 160 with blood vessels running along neck 42, extending from a region behind ear 36 along a neck 42 to provide heating or cooling to blood vessels that are near the surface of these regions. Because the dimensions and configuration position temperature modification devices in a position to maximize heat transfer with blood vessels running through the neck, the dimensions and configuration may be described as specialized dimensions and configuration. Temperature modification devices 160 are connected to power supply/control system 174 by, for example, a cable 176. The location of temperature modification devices 160 is such that cooling and/or warming is provided to the blood flowing through the blood vessels in the areas adjacent to temperature modification devices 160, which provide cooling to head 34 and, ultimately the brain. Temperature modification devices 160 can be adhered to the skin of subject or patient 40 in many ways, including adhesion and an adhesive. It should be understood that temperature modification devices 110 shown in FIGS. 4-7 can be used with apparatus 150.

In operation, apparatus 150 reads the temperature of ABTT terminus 10 by way of sensors 164. Sensors 164 send or transmit signals representative of the temperature of ABTT terminus 10. Control device 162 receives the temperature signals and analyzes the temperature signals. The analysis of the temperature signals by control device 162 determines whether a condition of patient or subject 40 exists that requires treatment of subject or patient 40 by temperature modification. If such treatment is required, as determined either by control device 162 or a separate electronic device (not shown) that communicates with control device 162, one or more temperature modification devices 160 are actuated to provide heating and/or cooling, preferably of the right carotid artery and left carotid artery, with continuous and simultaneous monitoring of the temperature of ABTT terminus 10. The temperature modification continues until the temperature at ABTT terminus 10 reaches a desired value, or until a predetermined time interval passes.

Temperature modification devices 160 have specialized dimension as a result of studies by Applicant that identified body regions that provide thermal signals to the brain, and these areas that provide thermal signals to the brain should be avoided. Those areas are viewed by the brain as thermal receptors for ambient temperature, thereby once excessive heat is detected in these areas the brain will send commands for the body to cool. Thus, if for example, in the prior art, someone who is hot wants to cool, this person applies a cool pad to the forehead, but the brain sees that "cooling" signal as the body is cold, and will retain heat, further worsening body heat. Thus, in certain areas, as recognized by Applicant, although one wants to cool, it should apply a warm pad, as for example the forehead. Another important aspect identified by Applicant is that the areas around blood vessels send signals to the brain, and thus should be avoided. Accordingly, for example, temperature modification devices 160 used to cool or heat the neck, is configured to precisely cover the carotid artery, but to avoid contacting a large area of neck 42 away from the carotid artery. Considering anatomy and physiology, the configuration of temperature modification device 160 comprises an essentially rectangular shape, or oblong shape, or even elliptical shape, which maximizes contact with the carotid artery area, but avoids other areas of neck 42. Considering the anatomy of the carotid artery, the length of the rectangle encompasses a line from the lobe of ear 36 to the superior aspect of a clavicle 178. Considering the anatomy and physiology of the carotid artery and neck thermal receptors, the preferred length of the rectangle is within a range of 205 mm to 125 mm, is more preferably within a range of 200 mm to 130 mm, is even more preferably in a range of 190 mm to 140 mm, and is yet most preferably in a range 185 mm to 145 mm. Considering the anatomy and physiology of the carotid artery and neck thermal receptors, the preferred width of the rectangle is 80 mm, is more preferably 45 mm, is even more preferably 30 mm, and is yet most preferably 15 mm. Considering the anatomy and physiology of the carotid artery and of the vertebral arteries, the preferred width of the rectangle is 95 mm, is more preferably 60 mm, is even more preferably 45 mm, and is yet most preferably 30 mm. In this manner, exposure of temperature modification device 160 is maximized over the main blood vessels, e.g., the carotid artery and the vertebral arteries, while avoiding other areas that contain thermal receptors.

Figure 10:
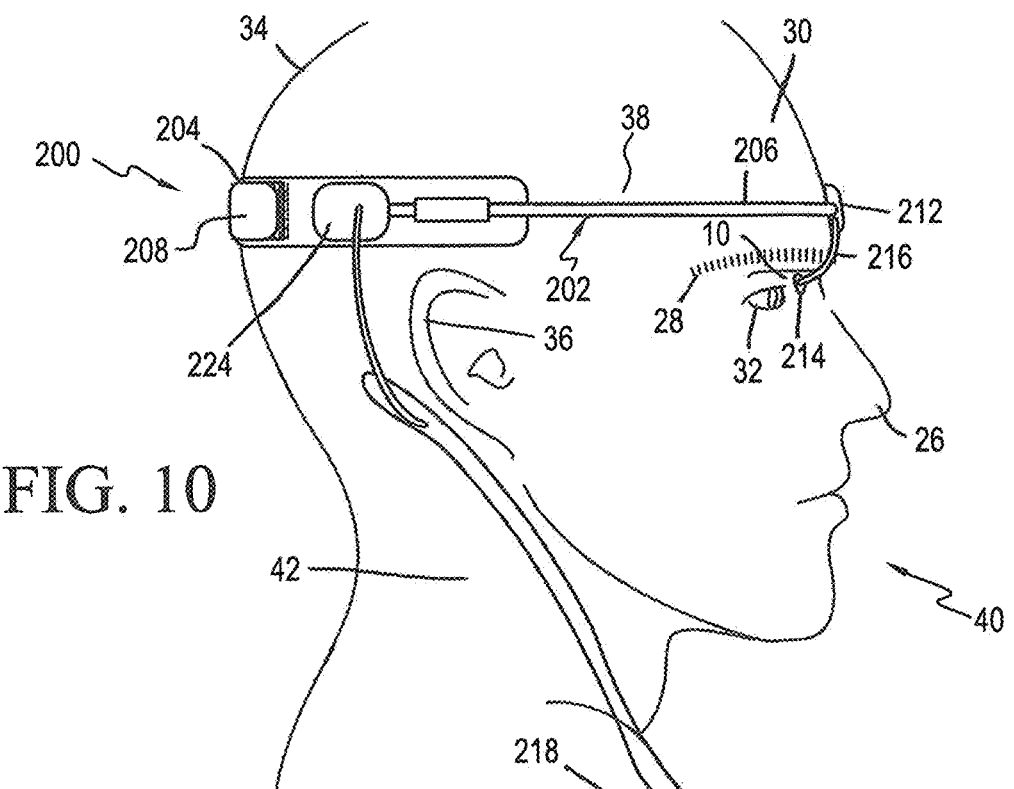
FIG. 10 shows a side view of a third apparatus in accordance with an exemplary embodiment of the present disclosure.
Figure 11:
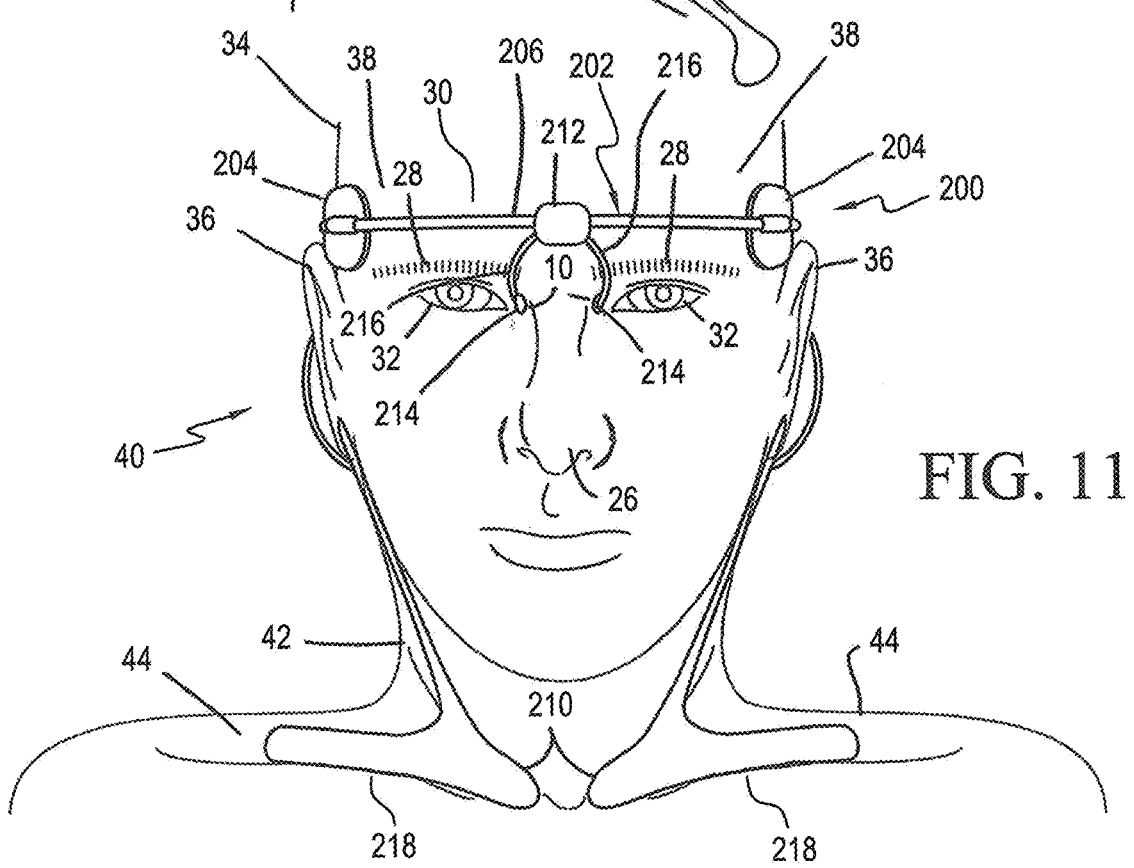
FIG. 11 shows a front view of the third apparatus of FIG. 10.

Temperature levels of temperature modification device 160 for cooling or warming the brain are as follows: a preferred temperature range of temperature modification device 160 is between 0 degrees Celsius and 50 degrees Celsius, is more preferably between 5 degrees Celsius and 45 degrees Celsius, is even more preferably between 10 degrees Celsius and 40 degrees Celsius, and is yet most preferably between 12 degrees Celsius and 38 degrees Celsius. The temperature level of temperature modification device 160 is determined by the target temperature of ABTT 12. It should be understood that the temperature ranges provided for temperature modification device 160 can be used for the other embodiments described herein. FIGS. 10 and 11 show a third apparatus in accordance with an exemplary embodiment of the present disclosure, indicated generally at 200. Apparatus 200 is configured to be positioned and at least partially supported on forehead 30 of head 34 in a location that is above eyebrows 28 and ears 36. Apparatus 200 is configured to include a support apparatus 202, which is configured to include a securing strap 204 and a support strap 206. Securing strap 204 is further configured with a device or mechanism to secure apparatus 200 to head 34. For example, securing strap 204 can be configured as an elastic strap that stretches to permit apparatus 200 to be positioned on and secured to head 34. In another embodiment, securing strap 204 can be configured to include a fastening apparatus 208, such as a buckle arrangement, or a hook and loop fastening apparatus.

Support apparatus 202 is configured to locate and position a plurality of elements, such as a control device 212, and a power supply/control system 224 configured to provide power to the electrically operated elements of apparatus 200 as well as providing control of elements of apparatus 200, as modified by input to, for example, control device 212. Control device 212 is configured to support one or more temperature sensors 214, configured to be positioned on ABTT terminus 10 and which can be connected to control device 212 by flexible, movable, or positionable supports 216. Control device 212 can be configured to include one or more control features, such as those shown in FIG. 5.

One or more temperature modification devices 210, which can be, for example, heating pads, thermoelectric devices, etc., are positioned to extend from a region behind ear 36, along neck 42, and then along shoulders 44 to provide heating or cooling to blood vessels that are near the surface of these regions. Temperature modification devices 210 are connected to power supply/control system 224 by, for example, a cable 226. The location of temperature modification devices 210 is such that cooling and/or warming is provided to the blood flowing through the blood vessels in the areas adjacent to temperature modification devices 210, which provide cooling to head 34 and, ultimately the brain. Temperature modification devices 210 can be adhered to the skin of subject or patient 40 in many ways, including adhesion and an adhesive. It should be understood that temperature modification devices 110 shown in FIGS. 4-7 can be used with apparatus 200.

In operation, apparatus 200 reads the temperature of ABTT terminus 10 by way of sensors 214 which transmits signals representative of ABTT terminus 10. Control device 212 receives the temperature signals and analyzes the temperature signals to determine whether a condition of subject or patient 40 exists that requires temperature modification of subject or patient 40. If such treatment is required, as determined either by control device 212 or a separate electronic device (not shown) that communicates with control device 212, one or more temperature modification devices 210 are actuated to provide heating and/or cooling, preferably of the right carotid artery and left carotid artery and extending into right subclavian region 218 and left subclavian region 218 (adjacent to shoulder 44), with continuous and simultaneous monitoring of the temperature of ABTT terminus 10. The temperature modification continues until the temperature at ABTT terminus 10 reaches a desired value, or until a predetermined time interval passes.

Figure 12:
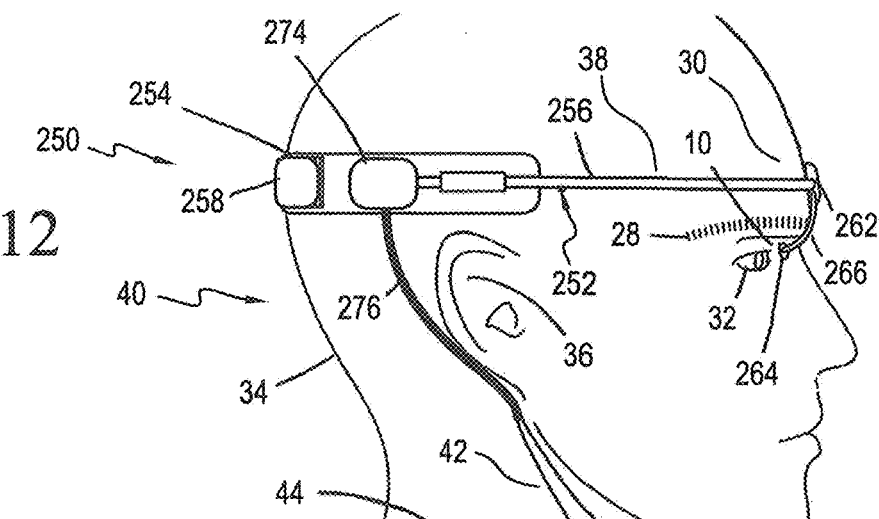
FIG. 12 shows a side view of a fourth apparatus in accordance with an exemplary embodiment of the present disclosure.
Figure 13:
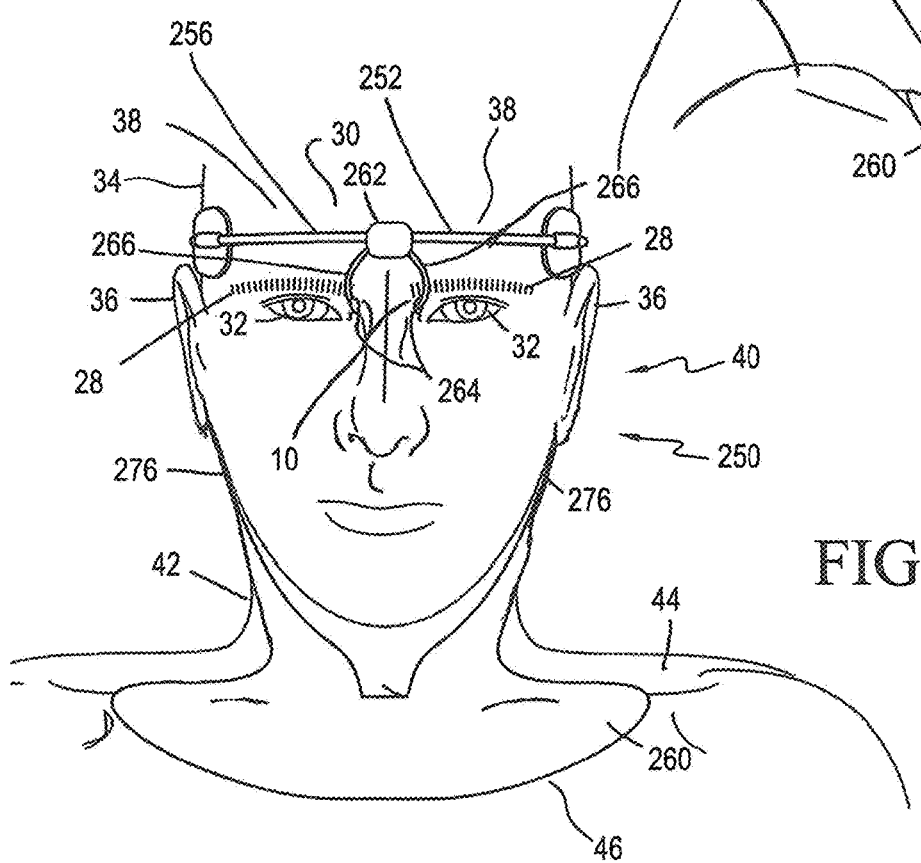
FIG. 13 shows a front view of the fourth apparatus of FIG. 12.

FIGS. 12 and 13 show a fourth apparatus in accordance with an exemplary embodiment of the present disclosure, indicated generally at 250. Apparatus 250 is configured to be positioned and at least partially supported on forehead 30 of head 34 in a location that is above eyebrows 28 and ears 36. Apparatus 250 is configured to include a support apparatus 252, which is configured to include a securing strap 254 and a support strap 256. Securing strap 254 is further configured with a device or mechanism to secure apparatus 250 to head 34. For example, securing strap 254 can be configured as an elastic strap that stretches to permit apparatus 250 to be positioned on and secured to head 34. In another embodiment, securing strap 254 can be configured to include a fastening apparatus 258, such as a buckle arrangement, or a hook and loop fastening apparatus.

Support apparatus 252 is configured to locate and position a plurality of elements, such as a control device 262, and a power supply/control system 274 configured to provide power to the electrically operated elements of apparatus 250 as well as providing control of elements of apparatus 250, as modified by input to, for example, control device 262. Control device 262 is configured to support one or more temperature sensors 264, configured to be positioned on ABTT terminus 10 and which can be connected to control device 262 by flexible, movable, or positionable supports 266. Control device 262 can be configured to include one or more control features, such as those shown in FIG. 5.

One or more temperature modification devices 260, which can be, for example, heating pads, thermoelectric devices, etc., are positioned to extend from a region below ear 36, along neck 42, and then along shoulders 44 and across a central portion of a chest 46 to provide heating or cooling to blood vessels that are near the surface of these regions. Temperature modification device 260 is connected to power supply/control system 274 by, for example, a cable 276. The location of temperature modification device 260 is such that cooling and/or warming is provided to the blood flowing through the blood vessels in the areas adjacent to temperature modification device 260, which provides cooling to head 34 and, ultimately the brain. Temperature modification device 260 can be adhered to the skin of subject or patient 40 in many ways, including adhesion and an adhesive. It should be understood that temperature modification devices 110 shown in FIGS. 4-7 can be used with apparatus 250.

In operation, apparatus 250 reads the temperature of ABTT terminus 10 by way of sensors 264. Control device 262 determines whether a condition exists that requires temperature modification of subject or patient 40. If such treatment is required, as determined either by control device 262 or a separate electronic device (not shown) that communicates with control device 262, one or more temperature modification devices 260 are actuated to provide heating and/or cooling, with continuous and simultaneous monitoring of the temperature of ABTT terminus 10. The temperature modification continues until the temperature at ABTT terminus 10 reaches a desired value, or until a predetermined time interval passes.

FIGS. 14-16 show a fifth apparatus in accordance with an exemplary embodiment of the present disclosure, indicated generally at 300. Apparatus 300 is configured to be positioned and at least partially supported on forehead 30 of head 34 in a location that is above eyebrows 28 and ears 36. Apparatus 300 is configured to include a support apparatus 302, which is configured to include a securing strap 304 and a support strap 306. Securing strap 304 is further configured with a device or mechanism to secure apparatus 300 to head 34. For example, securing strap 304 can be configured as an elastic strap that stretches to permit apparatus 300 to be positioned on and secured to head 34. In another embodiment, securing strap 304 can be configured to include a fastening apparatus 308, such as a buckle arrangement, or a hook and loop fastening apparatus.

Support apparatus 302 is configured to locate and position a plurality of elements, such as a control device 312, and a power supply/control system 324 configured to provide power to the electrically operated elements of apparatus 300 as well as providing control of elements of apparatus 300, as modified by input to, for example, control device 312. Control device 312 is configured to support one or more temperature sensors 314, configured to be positioned on ABTT terminus 10 and which can be connected to control device 312 by flexible, movable, or positionable supports 316. Control device 312 can be configured to include one or more control features, such as those shown in FIG. 5.

One or more temperature modification devices 310, which can be, for example, heating pads, thermoelectric devices, etc., are positioned to extend along a back of neck 42 to provide heating or cooling to blood vessels that are near the surface of that region. Temperature modification device 310 is connected to power supply/control system 324 by, for example, a cable 326. The location of temperature modification device 310 is such that cooling and/or warming is provided to the blood flowing through the blood vessels in the areas adjacent to temperature modification device 310, which provides cooling to head 34 and, ultimately the brain. Temperature modification device 310 can be adhered to the skin of subject or patient 40 in many ways, including adhesion and an adhesive. It should be understood that temperature modification devices 110 shown in FIGS. 4-7 can be used with apparatus 300.

In operation, apparatus 300 reads the temperature of ABTT terminus 10 by way of sensors 314, which transmit a signal representative of the temperature of ABTT terminus 10. Control device 312 receives the temperature signals and from the temperature signals determines whether subject or patient 40 requires temperature modification to treat a condition. If such treatment is required, as determined either by control device 312 or a separate electronic device (not shown) that communicates with control device 312, one or more temperature modification devices 310 are actuated to provide heating and/or cooling, preferably to the back of neck 42 along the vertebral arteries, with continuous and simultaneous monitoring of the temperature of ABTT terminus 10. The temperature modification continues until the temperature at ABTT terminus 10 reaches a desired value, or until a predetermined time interval passes.

Figure 17:
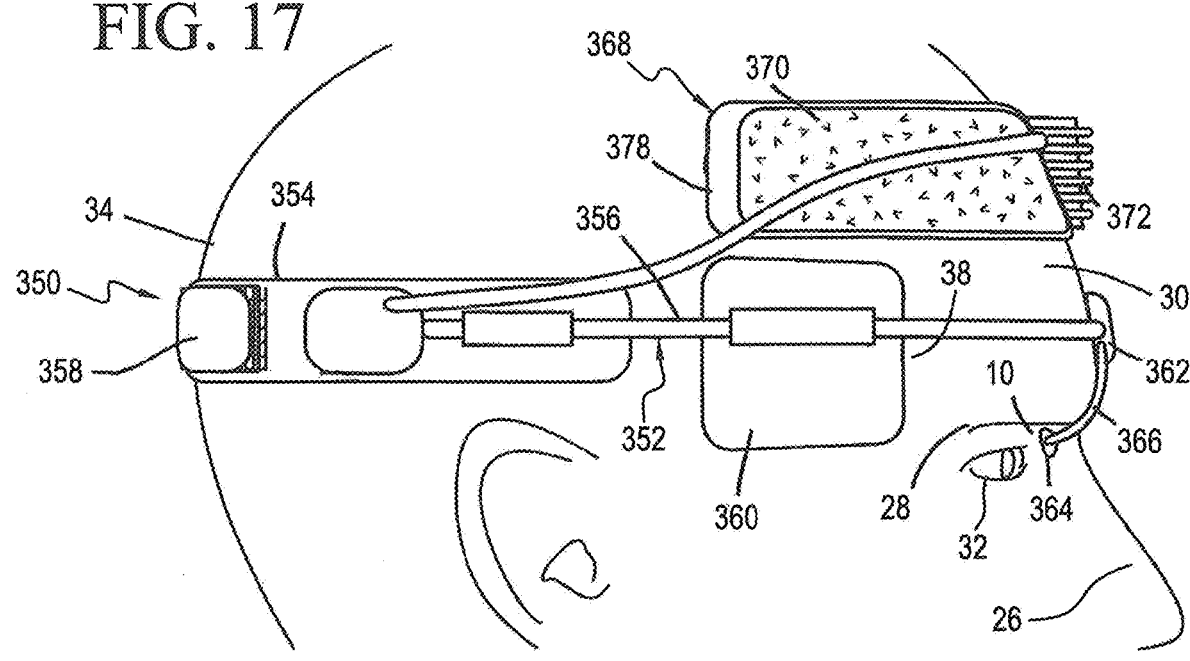
FIG. 17 shows a side view of a sixth apparatus in accordance with an exemplary embodiment of the present disclosure.
Figure 18:
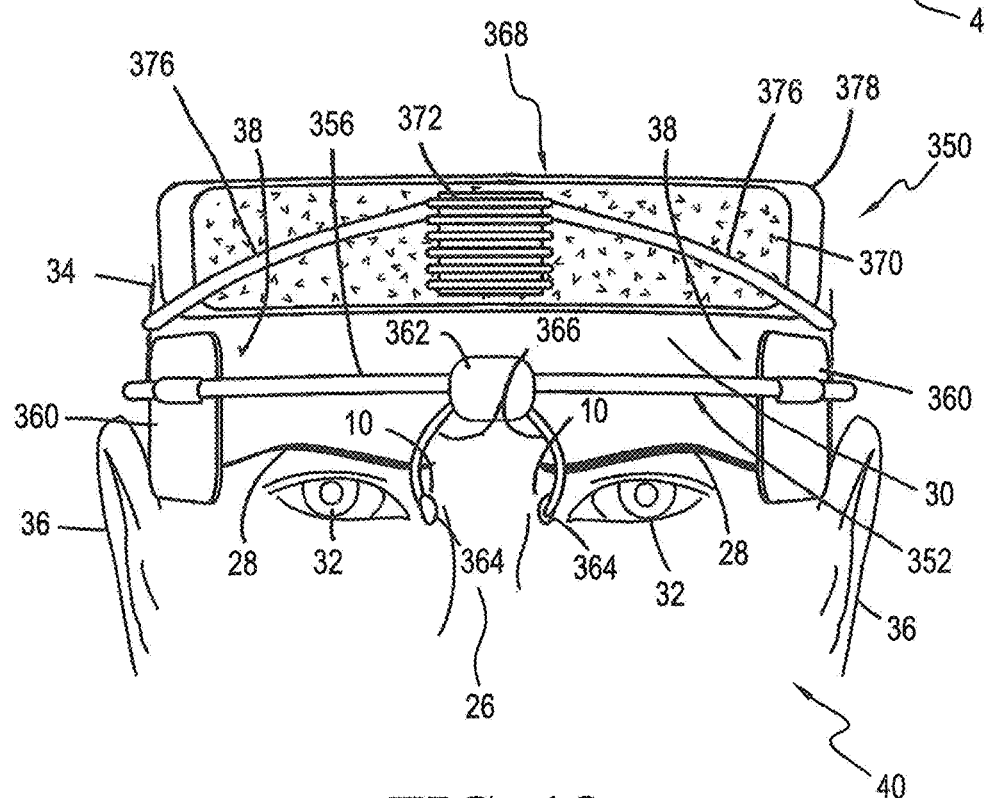
FIG. 18 shows a front view of the sixth apparatus of FIG. 17.

FIGS. 17 and 18 show a sixth apparatus in accordance with an exemplary embodiment of the present disclosure, indicated generally at 350. Apparatus 350 is configured to be positioned and at least partially supported on forehead 30 of head 34 in a location that is above eyebrows 28 and ears 36. Apparatus 350 is configured to include a support apparatus 352, which is configured to include a securing strap 354 and a support strap 356. Securing strap 354 is further configured with a device or mechanism to secure apparatus 350 to head 34. For example, securing strap 354 can be configured as an elastic strap that stretches to permit apparatus 350 to be positioned on and secured to head 34. In another embodiment, securing strap 354 can be configured to include a fastening apparatus 358, such as a buckle arrangement, or a hook and loop fastening apparatus.

Support apparatus 352 is configured to locate and position a plurality of elements, such as one or more temperature modification devices 360, which can be, for example, heating pads, thermoelectric devices, etc., configured and positioned to contact associated temple 38 of head 34 to provide heating and/or cooling of head 34, a control device 362, and a power supply/control system 374 configured to provide power to the electrically operated elements of apparatus 350 as well as providing control of elements of apparatus 350, as modified by input to, for example, control device 362. Control device 362 is configured to support one or more temperature sensors 364, configured to be positioned on ABTT terminus 10 and which can be connected to control device 362 by flexible, movable, or positionable supports 366. Control device 362 can be configured to include one or more control features, such as those shown in FIG. 5.

Another temperature modification device 368, which can be, for example, heating pads, thermoelectric devices, etc., is positioned to extend across forehead 30 to provide heating or cooling to blood vessels that are near the surface of forehead 30. Temperature modification device 368 is connected to power supply/control system 374 by, for example, a cable 376. Temperature modification device 368 can be configured to include a thermally conductive pad 370 to transfer heat to and from, for example, a thermoelectric device 372. Temperature modification device 368 can be configured to include an adhesive or adhesion layer 378 that is configured to attach temperature modification device 368 to forehead 30.

The location of temperature modification device 360 is such that cooling and/or warming is provided to the blood flowing through the blood vessels in the areas adjacent to temperature modification device 360, which provides cooling to head 34 and, ultimately the brain. Temperature modification device 360 can be adhered to the skin of subject or patient 40 in many ways, including adhesion and an adhesive.

In operation, apparatus 350 reads the temperature of ABTT terminus 10 by way of sensors 364. Control device 362 determines whether a condition exists that requires temperature modification of subject or patient 40. If such treatment is required, as determined either by control device 362 or a separate electronic device (not shown) that communicates with control device 362, one or more temperature modification devices 360 are actuated to provide heating and/or cooling, with continuous and simultaneous monitoring of the temperature of ABTT terminus 10. The temperature modification continues until the temperature at ABTT terminus 10 reaches a desired value, or until a predetermined time interval passes.

Figure 19:
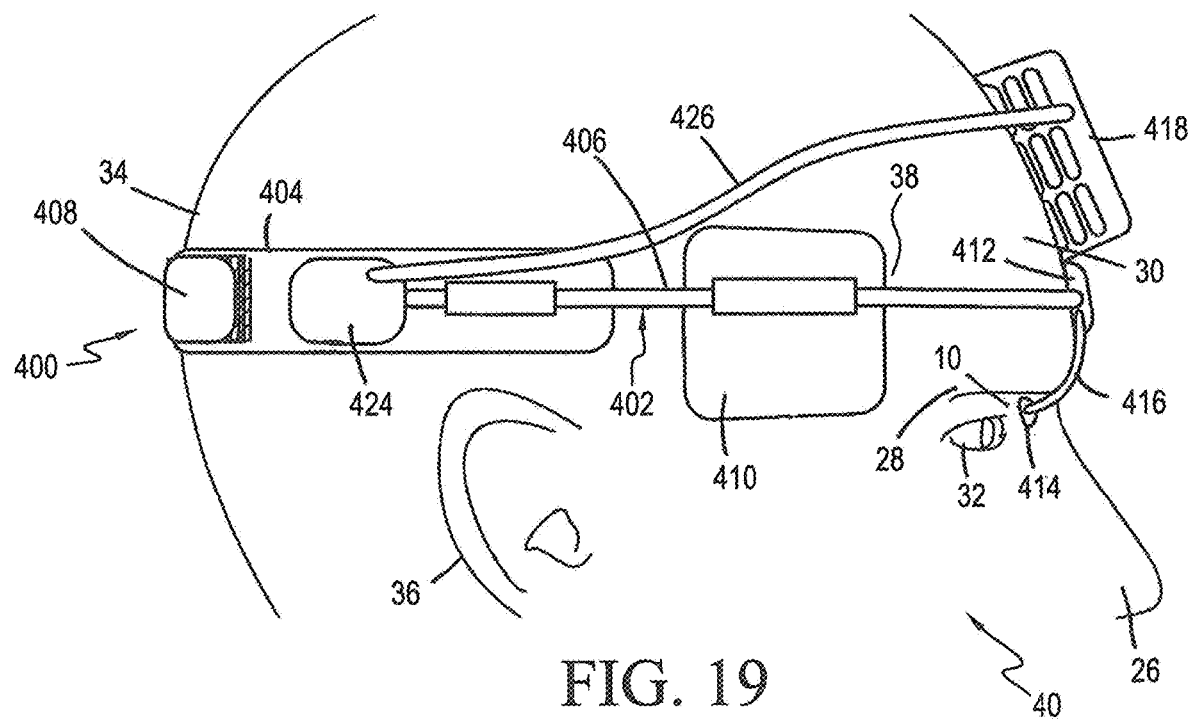
FIG. 19 shows a side view of a seventh apparatus in accordance with an exemplary embodiment of the present disclosure.
Figure 20:
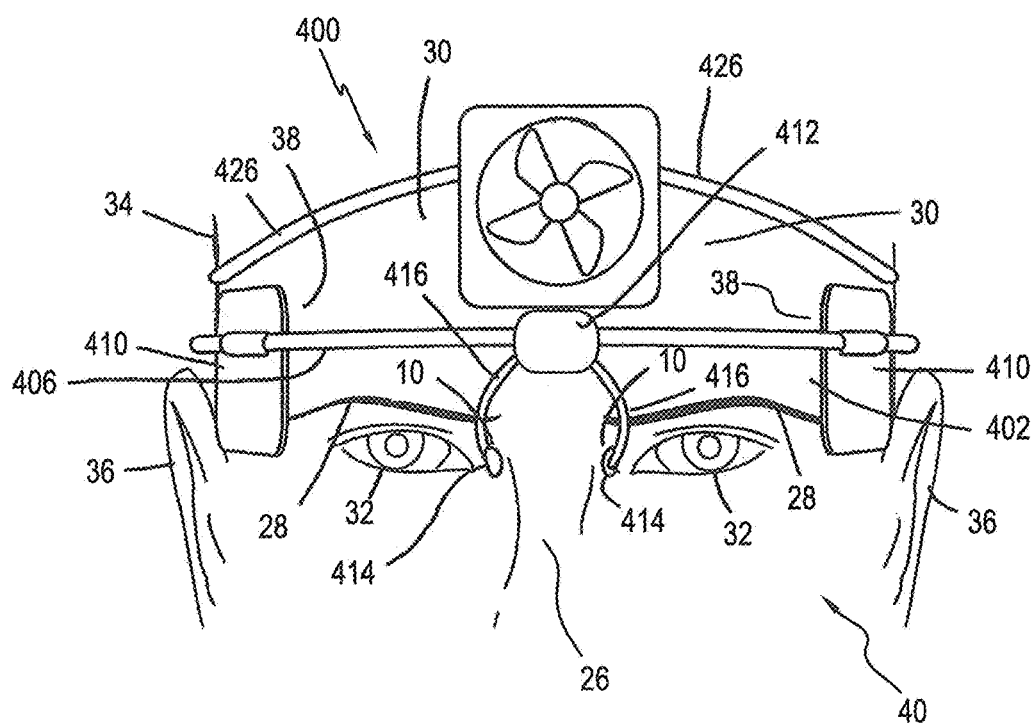
FIG. 20 shows a front view of the seventh apparatus of FIG. 19.

FIGS. 19 and 20 show a seventh apparatus in accordance with an exemplary embodiment of the present disclosure, indicated generally at 400. Apparatus 400 is configured to be positioned and at least partially supported on forehead 30 of head 34 in a location that is above eyebrows 28 and ears 36. Apparatus 400 is configured to include a support apparatus 402, which is configured to include a securing strap 404 and a support strap 406. Securing strap 404 is further configured with a device or mechanism to secure apparatus 400 to head 34. For example, securing strap 404 can be configured as an elastic strap that stretches to permit apparatus 400 to be positioned on and secured to head 34. In another embodiment, securing strap 404 can be configured to include a fastening apparatus 408, such as a buckle arrangement, or a hook and loop fastening apparatus.

Support apparatus 402 is configured to locate and position a plurality of elements, such as one or more temperature modification devices 410, which can be, for example, heating pads, thermoelectric devices, etc., configured and positioned to contact associated temple 38 of head 34 to provide heating and/or cooling of head 34, a control device 412, and a power supply/control system 424 configured to provide power to the electrically operated elements of apparatus 400 as well as providing control of elements of apparatus 400, as modified by input to, for example, control device 412.

Control device 412 is configured to support one or more temperature sensors 414, configured to be positioned on ABTT terminus 10 and which can be connected to control device 412 by flexible, movable, or positionable supports 416. Control device 412 can be configured to include one or more control features, such as those shown in FIG. 5.

Another temperature modification device 418 in the form of a fan is positioned on forehead 30 to provide cooling to blood vessels that are near the surface of forehead 30. Temperature modification device 418 is connected to power supply/control system 424 by, for example, a cable 426.

The location of temperature modification devices 410 and 418 is such that cooling and/or warming is provided to the blood flowing through the blood vessels in the areas adjacent to temperature modification devices 410 and 418, which provides cooling and/or warming to head 34 and, ultimately the brain. Temperature modification device 418 can be adhered to the skin of subject or patient 40 in many ways, including adhesion and an adhesive.

In operation, apparatus 400 reads the temperature of ABTT terminus 10 by way of sensors 414. Control device 412 determines whether a condition exists that requires temperature modification of subject or patient 40. If such treatment is required, as determined either by control device 412 or a separate electronic device (not shown) that communicates with control device 412, one or more temperature modification devices 410 and 418 are actuated to provide heating and/or cooling, with continuous and simultaneous monitoring of the temperature of ABTT terminus 10. The temperature modification continues until the temperature at ABTT terminus 10 reaches a desired value, or until a predetermined time interval passes.

Figure 21:
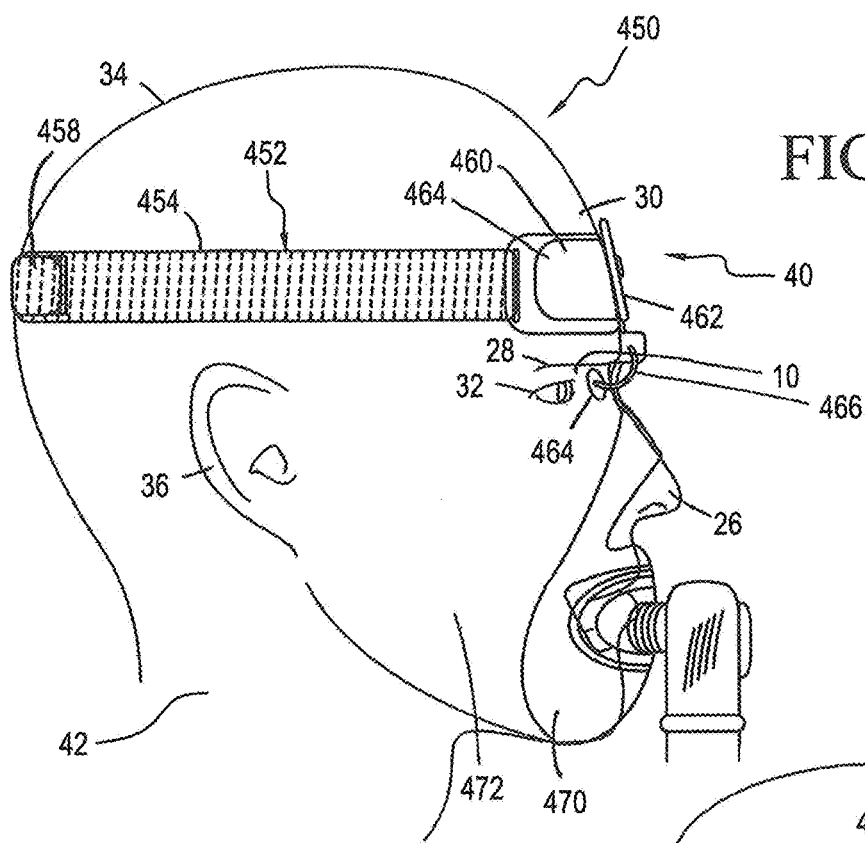
FIG. 21 shows a side view of an eighth apparatus in accordance with an exemplary embodiment of the present disclosure.
Figure 22:
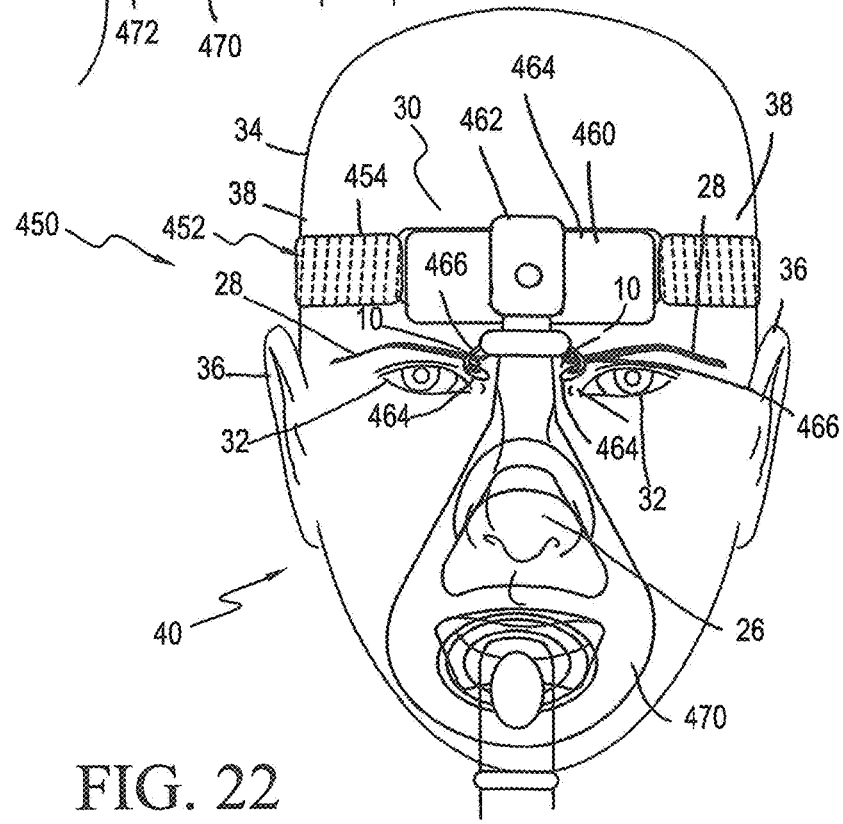
FIG. 22 shows a front view of the eighth apparatus of FIG. 21.

FIGS. 21 and 22 show an eighth apparatus in accordance with an exemplary embodiment of the present disclosure, indicated generally at 450. Apparatus 450 is configured to be positioned and at least partially supported on forehead 30 of head 34 in a location that is above eyebrows 28 and ears 36. Apparatus 450 is configured to include a support apparatus 452, which is configured to include a securing and support strap 454. Securing and support strap 454 is further configured with a device or mechanism to secure apparatus 450 to head 34. For example, securing and support strap 454 can be configured as an elastic strap that stretches to permit apparatus 450 to be positioned on and secured to head 34. In another embodiment, securing and support strap 454 can be configured to include a fastening apparatus 458, such as a buckle arrangement, or a hook and loop fastening apparatus.

Support apparatus 452 is configured to locate and position a plurality of elements, such as one or more temperature modification devices 460, which can be, for example, heating pads, thermoelectric devices, etc., configured and positioned to contact forehead 30 of head 34 to provide heating and/or cooling of head 34, a control device 462, and a power supply/control system 464 configured to be collocated with temperature modification device 460 to provide power to the electrically operated elements of apparatus 450 as well as providing control of elements of apparatus 450, as modified by input to, for example, control device 462. Control device 462 is configured to support one or more temperature sensors 464, configured to be positioned on ABTT terminus 10 and which can be connected to control device 462 by flexible, movable, or positionable supports 466. Control device 462 can be configured to include one or more control features, such as those shown in FIG. 5.

Apparatus 450 is further configured to include a face mask 470 that is configured to include an intubation device 472, which in the configuration of FIGS. 21 and 22 is integral to apparatus 450.

The location of temperature modification device 460 is such that cooling and/or warming is provided to the blood flowing through the blood vessels in the areas adjacent to temperature modification device 460, which provides cooling and/or warming to head 34 and, ultimately the brain.

In operation, apparatus 450 reads the temperature of ABTT terminus 10 by way of sensors 464. Control device 462 determines whether a condition exists that requires temperature modification of subject or patient 40. If such treatment is required, as determined either by control device 462 or a separate electronic device (not shown) that communicates with control device 462, temperature modification device 460 is actuated to provide heating and/or cooling, with continuous and simultaneous monitoring of the temperature of ABTT terminus 10. The temperature modification continues until the temperature at ABTT terminus 10 reaches a desired value, or until a predetermined time interval passes.

FIGS. 23 and 24 show a ninth apparatus in accordance with an exemplary embodiment of the present disclosure, indicated generally at 500. Apparatus 500 is configured to be positioned and at least partially supported on forehead 30 of head 34 in a location that is above eyebrows 28 and ears 36. Apparatus 500 is configured to include a support apparatus 502, which is configured to include a securing and support strap 504. Securing and support strap 504 is further configured with a device or mechanism to secure apparatus 500 to head 34. For example, securing and support strap 504 can be configured as an elastic strap that stretches to permit apparatus 500 to be positioned on and secured to head 34. In another embodiment, securing and support strap 504 can be configured to include a fastening apparatus 508, such as a buckle arrangement, or a hook and loop fastening apparatus.

Support apparatus 502 is configured to locate and position a plurality of elements, such as a temperature modification device 510, which can be, for example, heating pads, thermoelectric devices, etc., configured and positioned to contact forehead 30 of head 34 to provide heating and/or cooling of head 34, a control device 512, and a power supply/control system 524 to provide power to the electrically operated elements of apparatus 500 as well as providing control of elements of apparatus 500, as modified by input to, for example, control device 512. Apparatus 500 can be configured to include a forehead support 506 that is configured to position and locate one or more elements of apparatus 500, such as temperature modification device 510, control device 512, and power supply/control system 524. Forehead support 506 is further configured to support one or more temperature sensors 514, configured to be positioned on ABTT terminus 10 and which can be connected to control device 512 by a flexible, movable, or positionable support 516. Control device 512 can be configured to include one or more control features, such as those shown in FIG. 5.

The location of temperature modification device 510 is such that cooling and/or warming is provided to the blood flowing through the blood vessels in the areas adjacent to temperature modification device 510, which provides cooling and/or warming to head 34 and, ultimately the brain.

In operation, apparatus 500 reads the temperature of ABTT terminus 10 by way of sensors 514. Control device 512 determines whether a condition exists that requires temperature modification of subject or patient 40. If such treatment is required, as determined either by control device 512 or a separate electronic device (not shown) that communicates with control device 512, temperature modification device 510 is actuated to provide heating and/or cooling, with continuous and simultaneous monitoring of the temperature of ABTT terminus 10. The temperature modification continues until the temperature at ABTT terminus 10 reaches a desired value, or until a predetermined time interval passes.

Figure 25:
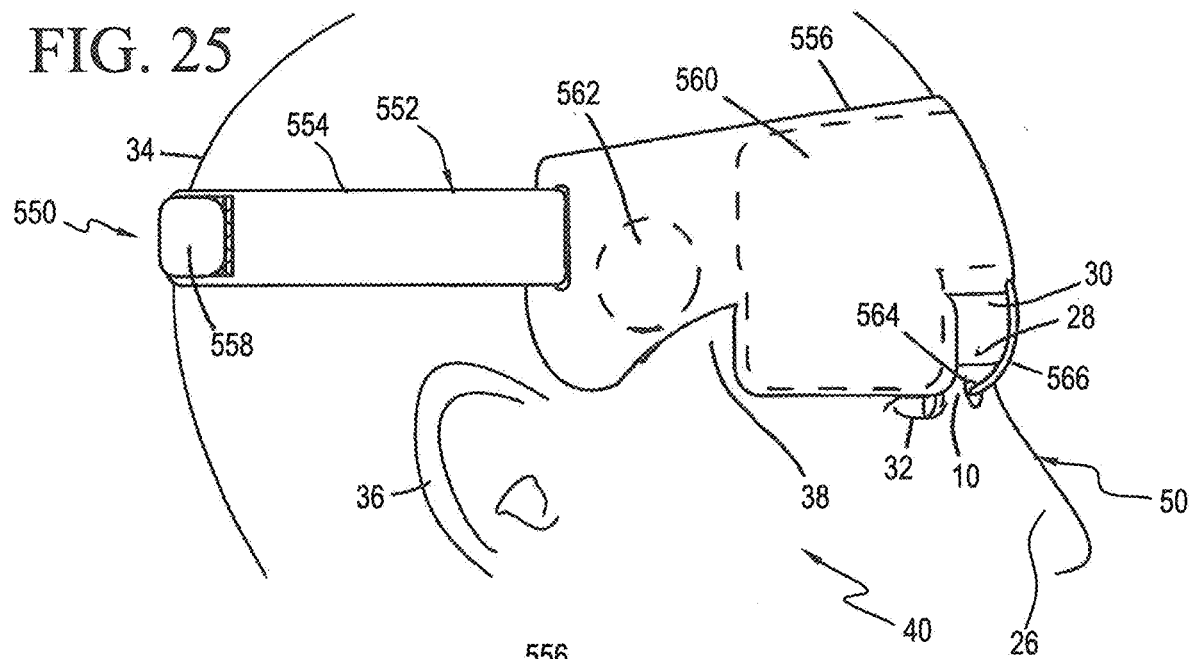
FIG. 25 shows a side view of a tenth apparatus in accordance with an exemplary embodiment of the present disclosure.
Figure 26:
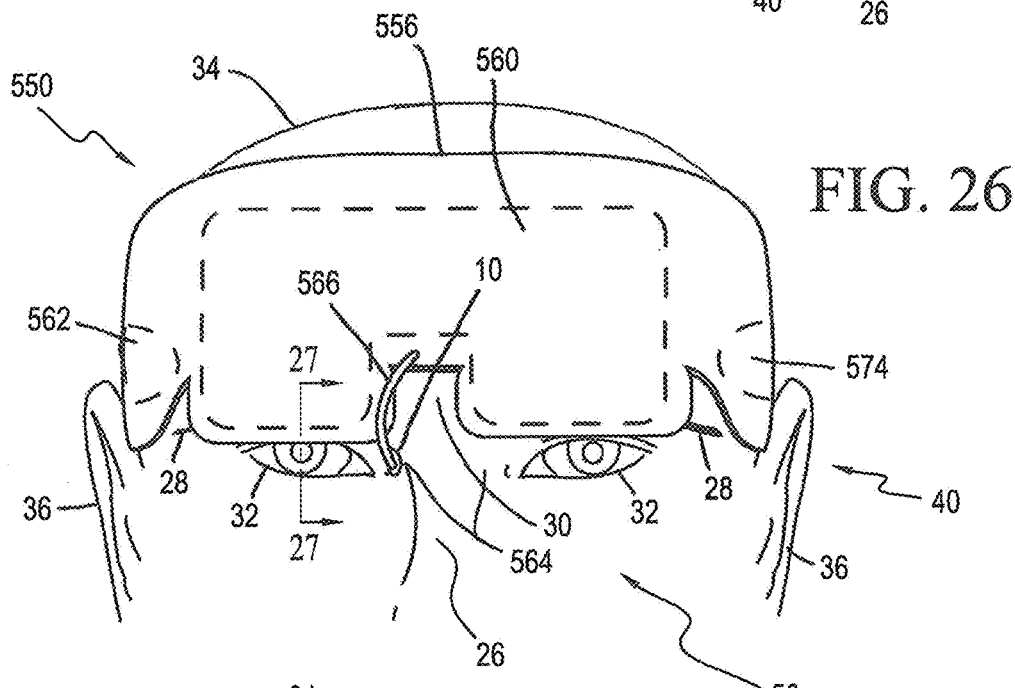
FIG. 26 shows a front view of the tenth apparatus of FIG. 25.
Figure 27:
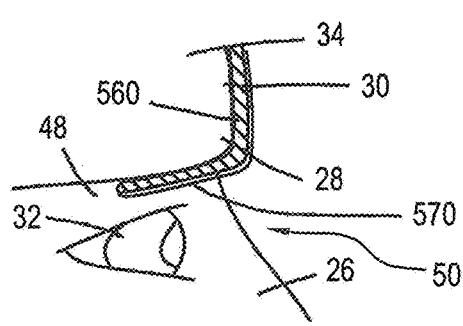
FIG. 27 shows a cross-sectional view of the tenth apparatus of FIG. 26 along the lines 27-27.

FIGS. 25-27 show a tenth apparatus in accordance with an exemplary embodiment of the present disclosure, indicated generally at 550. Apparatus 550 is configured to be positioned and at least partially supported on forehead 30 of head 34 in a location that is above eyebrows 28 and ears 36. Apparatus 550 is configured to include a support apparatus 552, which is configured to include a securing and support strap 554. Securing and support strap 554 is further configured with a device or mechanism to secure apparatus 550 to head 34. For example, securing and support strap 554 can be configured as an elastic strap that stretches to permit apparatus 550 to be positioned on and secured to head 34. In another embodiment, securing and support strap 554 can be configured to include a fastening apparatus 558, such as a buckle arrangement, or a hook and loop fastening apparatus.

Support apparatus 552 is configured to locate and position a plurality of elements, such as a temperature modification device 560, which can be, for example, heating pads, thermoelectric devices, etc., configured and positioned to contact forehead 30 of head 34 to provide heating and/or cooling of head 34, a control device 562, and a power supply/control system 574 to provide power to the electrically operated elements of apparatus 550 as well as providing control of elements of apparatus 550, as modified by input to, for example, control device 562. Apparatus 550 can be configured to include a forehead support 556 that is configured to position and locate one or more elements of apparatus 550, such as temperature modification device 560, control device 562, and power supply/control system 574. Forehead support 556 is further configured to support one or more temperature sensors 564, configured to be positioned on ABTT terminus 10 and which can be connected to control device 562 by a flexible, movable, or positionable support 566. Control device 562 can be configured to include one or more control features, such as those shown in FIG. 5.

The location of temperature modification device 560 is such that cooling and/or warming is provided to the blood flowing through the blood vessels in the areas adjacent to temperature modification device 560, which provides cooling and/or warming to head 34 and, ultimately the brain. Temperature modification device 560 can be configured to include a flap or extension 570 that is configured to contact an area of an ocular cavity 48 that is under or below eyebrow 28. Thus, temperature modification device 560, which is true of the other embodiments of the present disclosure, conforms to the features of head 34, including a facial portion 50 of head 34.

In operation, apparatus 550 reads the temperature of ABTT terminus 10 by way of sensors 564, which transmit signals representative of the temperature of ABTT terminus 10. Control device 562 receives the temperature signals and determines from the temperature signals whether subject or patient 40 requires temperature modification to treat a condition or illness. If such treatment is required, as determined either by control device 562 or a separate electronic device (not shown) that communicates with control device 562, temperature modification device 560 is actuated to provide heating and/or cooling, with continuous and simultaneous monitoring of the temperature of ABTT terminus 10. The temperature modification continues until the temperature at ABTT terminus 10 reaches a desired value, or until a predetermined time interval passes.

Figure 28:
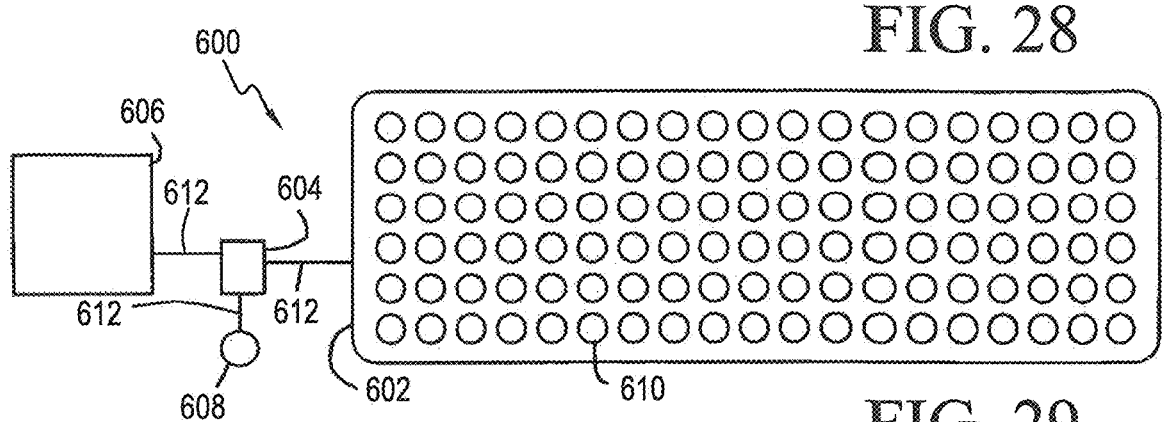
FIG. 28 shows a view of a first temperature modification device in accordance with an exemplary embodiment of the present disclosure.

A temperature modification device in accordance with an exemplary embodiment can take many configurations. A first exemplary temperature modification device embodiment in accordance the present disclosure is shown schematically in FIG. 28 and indicated generally at 600. Temperature modification device 600 is configured to include a support 602, one or more operating controls or switches 604, a power supply and control 606, a temperature sensor 608, which is configured to be positioned on ABTT terminus 10, and a resistive heating element 610. Elements of temperature modification device 600 can be connected to each other by way of a cable 612. Functionally, when a temperature signal from temperature sensor 608 indicates a need to heat ABTT terminus 10, power is provided to one or more resistive heating elements 610 to transfer heat to ABTT terminus 10, until a temperature signal from temperature sensor 608 indicates a predetermined or set temperature is reached, or passing of a predetermined time interval, at which time power will be removed from resistive heating elements 610.

Figure 29:
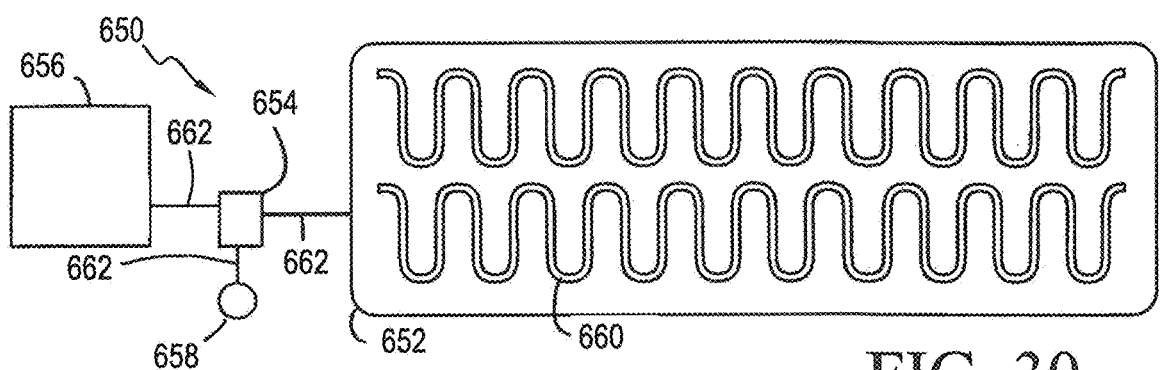
FIG. 29 shows a view of a second temperature modification device in accordance with an exemplary embodiment of the present disclosure.

FIG. 29 shows a view of a second exemplary temperature modification device embodiment in accordance the present disclosure, and indicated generally at 650. Temperature modification device 650 is configured to include a support 652, one or more operating controls or switches 654, a power supply and control 656, a temperature sensor 658, which is configured to be positioned on ABTT terminus 10, and a radiative heating element 660. Elements of temperature modification device 650 can be connected to each other by way of a cable 652. Functionally, when a temperature signal from temperature sensor 658 indicates a need to heat ABTT terminus 10, power is provided to one or more radiative heating elements 660 to transfer heat to ABTT terminus 10, until a temperature signal from temperature sensor 658 indicates a predetermined or set temperature is reached, or passing of a predetermined time interval, at which time power will be removed from resistive heating elements 610.

Figure 30:
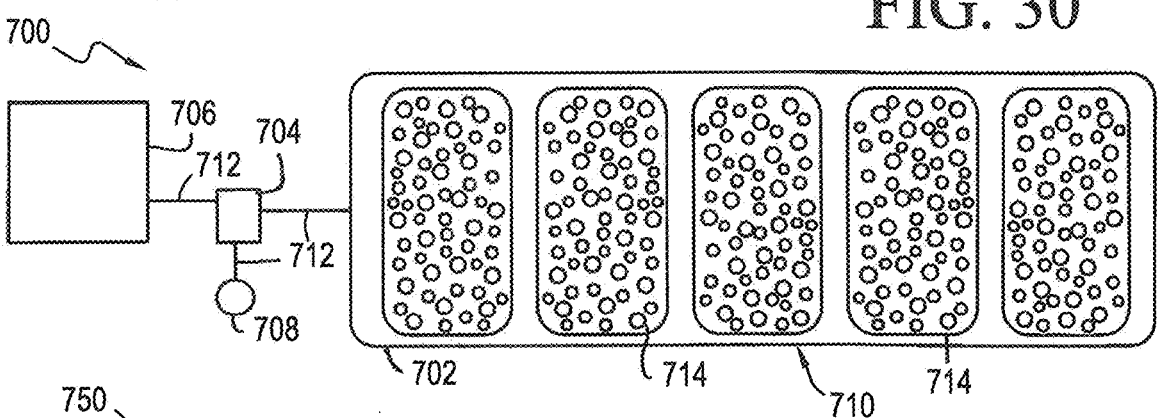
FIG. 30 shows a view of a third temperature modification device in accordance with an exemplary embodiment of the present disclosure.

FIG. 30 shows a view of a third exemplary temperature modification device embodiment in accordance the present disclosure, and indicated generally at 700. Temperature modification device 700 is configured to include a support 702, one or more operating controls or switches 704, a power supply and control 706, a temperature sensor 708, which is configured to be positioned on ABTT terminus 10, and a gel pack assembly 710, which can be configured to include a plurality of individual gel packs 714. Elements of temperature modification device 700 can be connected to each other by way of a cable 712. Functionally, temperature modification device 700 is somewhat difference from some of the embodiments disclosed herein in that gel pack assembly 710 is heated or cooled prior to positioning on subject or patient 40. Thus, gel pack assembly 710 is not controlled by controls and switches 704 and power supply and control 706, which instead provide an indication that a temperature signal from temperature sensor 708 indicates a predetermined or set temperature is reached, or passing of a predetermined time interval, at which time a user or the subject will receive a notification to remove gel pack assembly from subject or patient 40.

Figure 31:
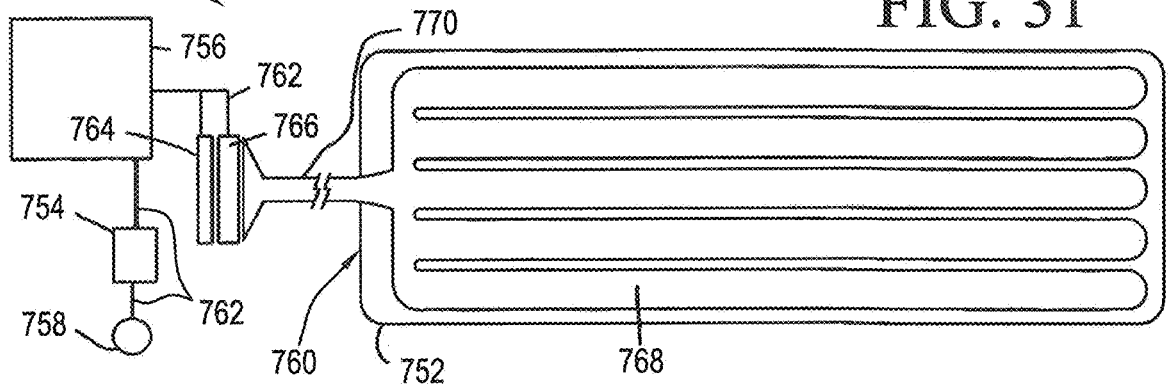
FIG. 31 shows a view of a fourth temperature modification device in accordance with an exemplary embodiment of the present disclosure.

FIG. 31 shows a view of a fourth exemplary temperature modification device embodiment in accordance the present disclosure, and indicated generally at 750. Temperature modification device 750 is configured to include a support 752, one or more operating controls or switches 754, a power supply and control 756, a temperature sensor 758, which is configured to be positioned on ABTT terminus 10, and a thermal transfer assembly 760. Elements of temperature modification device 750 can be connected to each other by way of a cable 762.

Thermal transfer assembly 760 is configured to include a fan 764, a temperature modification element 766, which can be a thermoelectric device, a resistive heater, a pre-warmed or cooled element, etc., one or more flow passages 768, and a connecting passage 770 that extends between flow passages 768 and temperature modification element 766.

Functionally, when a temperature signal from temperature sensor 758 indicates a need to heat ABTT terminus 10, power is provided to temperature modification element 766, which can warm and which can be configured to cool. After a suitable period of warming or cooling, power is provided to fan 764, which starts the flow of warmed or cooled air through connecting passage 770 and into flow passages 786, which are formed in support 752. Such warming or cooling flow continues until a temperature signal from temperature sensor 758 indicates a predetermined or set temperature is reached, or passing of a predetermined time interval, at which time power will be removed from temperature modification element 766 and fan 764.

FIGS. 32 and 33 show an eleventh apparatus in accordance with an exemplary embodiment of the present disclosure, indicated generally at 800. Apparatus 800 is configured to be positioned and at least partially supported on forehead 30 of head 34 in a location that is above eyebrows 28, and partially by at least one ear 36. Apparatus 800 is configured to be connected to a separate electronic device 822, which can be, for example, a cell phone, tablet, laptop, etc. Apparatus 800 is configured to include one or more ear buds 802, a microphone 804, a control device 812, and at least one temperature sensor 814 supported by control device 812. Temperature sensor 814 is configured to be positioned on ABTT terminus 10 and can be connected to control device 812 by a movable, flexible, or positionable support 816. Apparatus 800 further includes a cable 806 that connects control device 812 to an ear bud 802, a cable 808 that connects ear bud 802 to microphone 804, a cable 810 that connects microphone 804 to separate electronic device 822, and a cable 816 that connects another ear bud 802 to separate electronic device 822.

Apparatus 800 is partially supported on head 34 by the contact of ear bud(s) 802 with ear(s) 36, partially supported on head 34 by the routing of cable 806 around and over ear 36, and the contact of control device 812 with forehead 30. Control device 312 can be held in place by an adhesive.

In operation, apparatus 800 reads the temperature of ABTT terminus 10 by way of sensors 814. Control device 812 transmits the temperature information via cables 806, 808, and 810 to separate electronic device 822, which can then analyze and/or report the temperature information, store the information for later use, and/or transmit the temperature information by wire or wirelessly to another device for analysis, storage, and/or reporting. Communication between temperature sensor 814 and any separate electronic device, such as device 822, can also be performed wirelessly.

Figures 34, 35, 36:
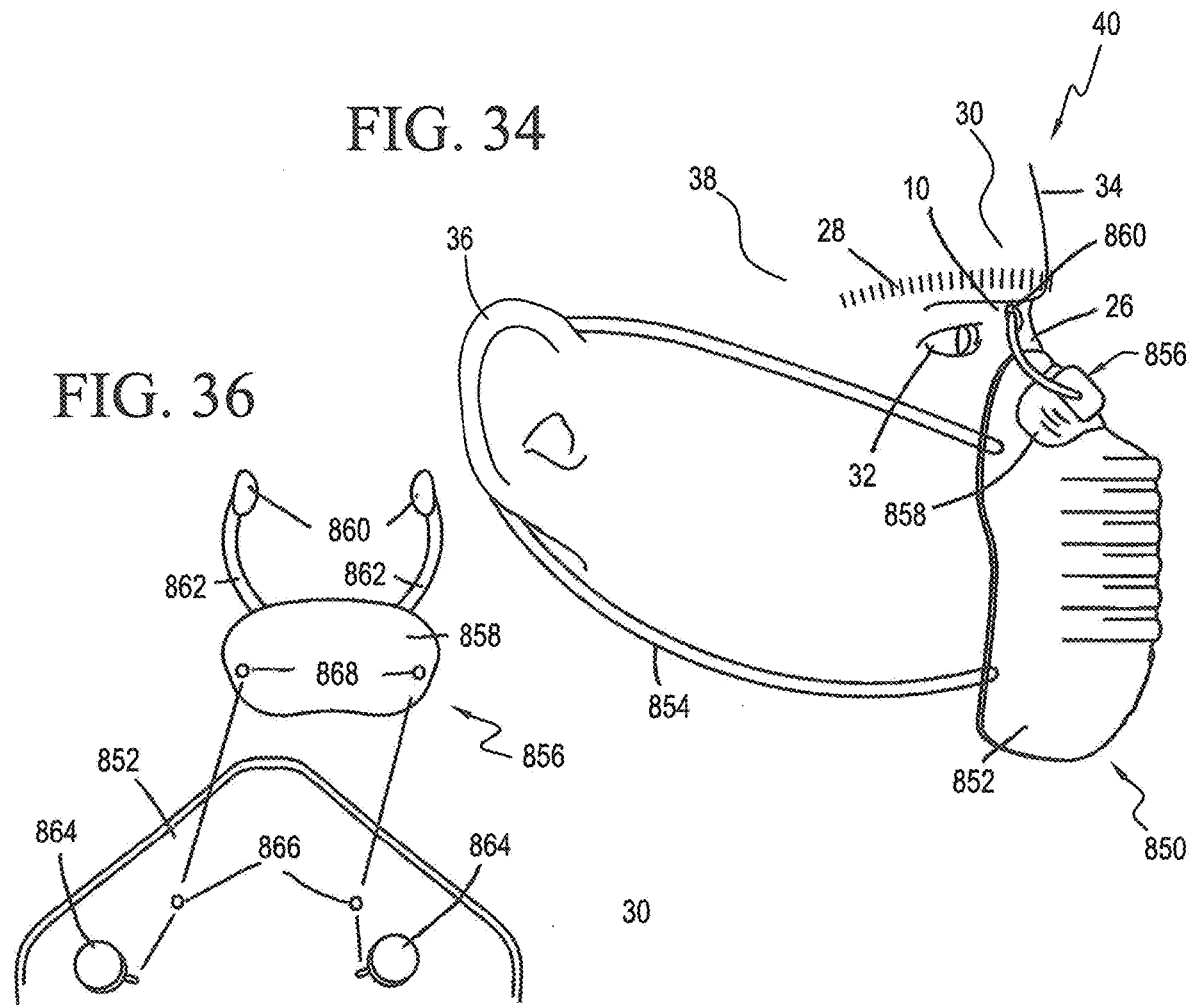
FIG. 34 shows a side view of a twelfth apparatus in accordance with an exemplary embodiment of the present disclosure.
FIG. 35 shows a front view of the twelfth apparatus of FIG. 34.
FIG. 36 shows a view of a portion of the twelfth apparatus of FIGS. 34 and 35.

FIGS. 34-36 show a twelfth apparatus in accordance with an exemplary embodiment of the present disclosure, indicated generally at 850. Apparatus 850 is configured to be positioned on and supported by head 34, and in the exemplary embodiment shown in FIGS. 34 and 35, such support is by way of ears 36. Apparatus 850 is configured to include a mask 852 that includes a carbon dioxide sensor. Mask 852 fully covers nose 26 and a mouth of patient or subject 40, and is supported on ears 36 by stretchable or expandable straps 854.

Mask 854 is configured to support and position a temperature sensor assembly 856, which is configured to be positioned on ABTT terminus 10. Temperature sensor assembly 856 is configured to include a base 858 and one or more temperature sensors 860, which are supported on base 858 by flexible supports 860 that enable repositioning of temperature sensors 860 for mating with ABTT terminus 10.

Temperature sensor assembly 856 can be attached to mask 852 by way of fasteners 864, which are configured to extend through openings 866 formed in mask 852 to connect or attach to a mating feature 868 formed in temperature sensor assembly 856.

In operation, apparatus 850 reads the temperature of ABTT terminus 10 by way of sensors 860. The signals from temperature sensors 860 is transmitted wirelessly or by cable to a separate electronic device, such as separate electronic device 822 shown in FIG. 32, for storage, analysis, display, etc.

Figure 37:
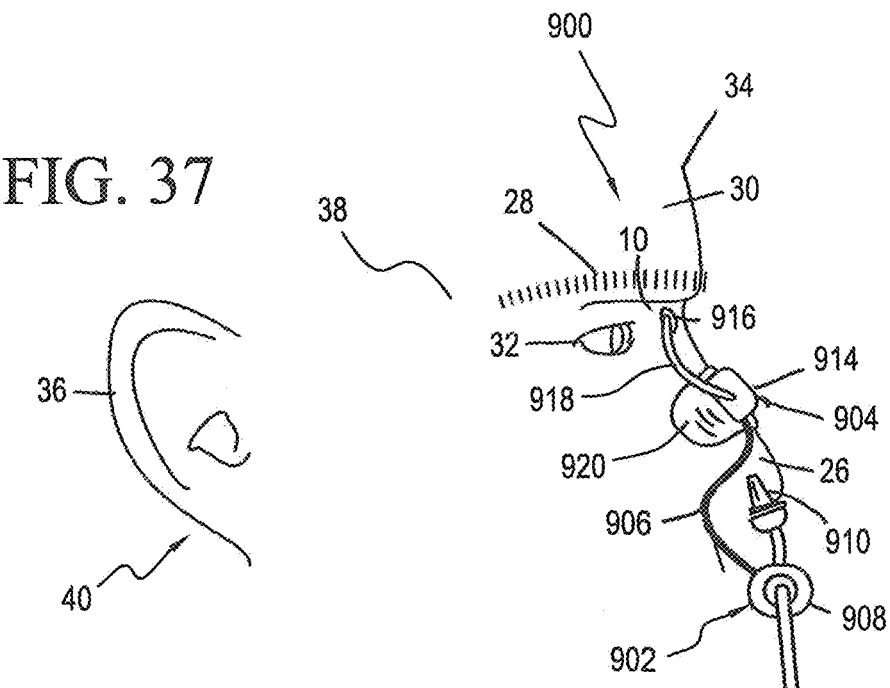
FIG. 37 shows a side view of a thirteenth apparatus in accordance with an exemplary embodiment of the present disclosure.
Figure 38:
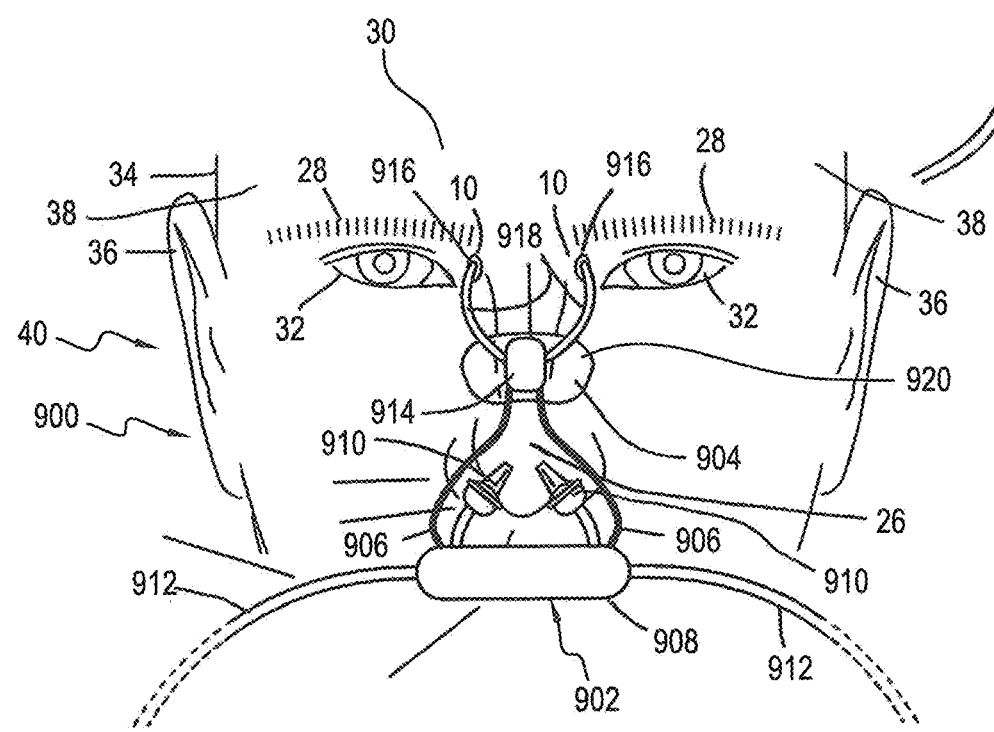
FIG. 38 shows a front view of the thirteenth apparatus of FIG. 37.

FIGS. 37 and 38 show a thirteenth apparatus in accordance with an exemplary embodiment of the present disclosure, indicated generally at 900. Apparatus 900 is configured to be positioned on and supported by nose 26. Apparatus 900 is configured to include an air flow assembly 902 and a temperature sensor assembly 904, which is connected to air flow assembly 902 by way of cables 906.

Air flow assembly 902 includes a manifold 908, and nostril interfaces 910 that are inserted into openings or nostrils of nose 26. Manifold 908 is connected to a remote source of temperature controlled air by way of one or more air flow passages 912, which can be hoses, tubes, lines, etc., configured to carry flowing air from a remote source to manifold 908. The function of air flow assembly can include air to treat apnea, COPD, and other respiratory conditions where assisted breathing is beneficial.

Temperature sensor assembly 904 is configured to include a control device 914, which may include buttons, switches, and other inputs and outputs to control the operation of apparatus 900, at least one temperature sensor 916 configured to be positioned on ABTT terminus 10, which is connected to control device 914 by flexible, movable, or positionable supports 918, and a nose interface 920, which is configured to be attached to nose 26 by adhesion or an adhesive and which is configured to support the elements of temperature sensor assembly 904 on nose 26.

Functionally, temperature sensors transmit signals control device 914. Control device 914 can then transmit temperature signals to a remote electronic device, wirelessly or by a wired connection configured as part of air flow passages 912, or can translate the temperature signals from temperature sensors 916 into a need for cooling or warming. If a need for cooling or warming is determined, signals are transmitted to the remote electronic device, which can be configured as an air flow system, to provide cooled or warmed air via air flow passages 912, which flows into manifold 908, and then into nostril interfaces 910, for delivery to nostrils of nose 26. Thus, cooling of the brain of head 34 can be accomplished by sensing the temperature at ABTT terminus 10 and providing cooling or warming air to the sinus passages of head 34.

Figure 39:
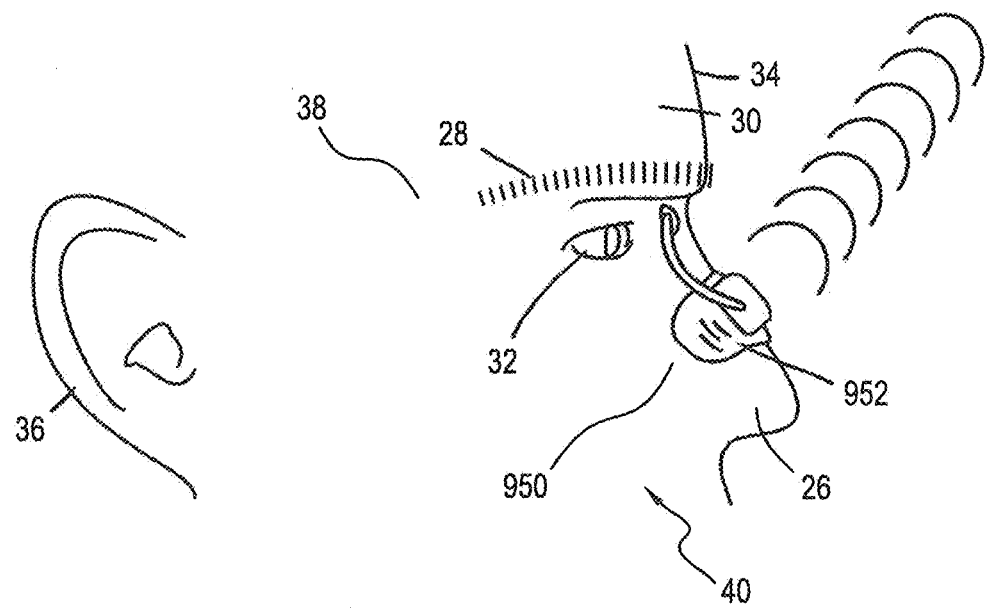
FIG. 39 shows a side view of a fourteenth apparatus in accordance with an exemplary embodiment of the present disclosure.
Figure 40:
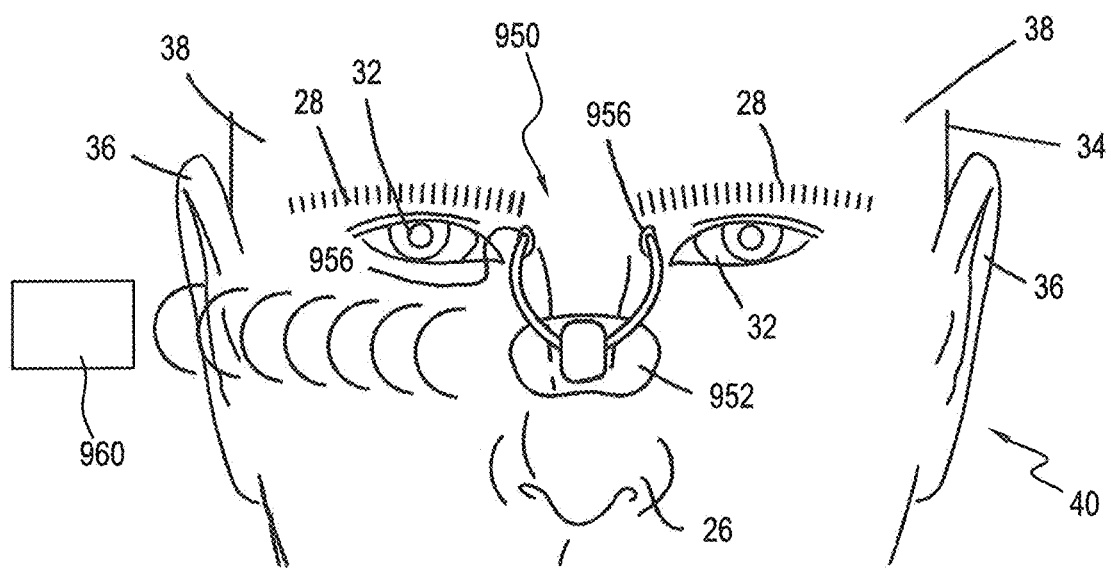
FIG. 40 shows a front view of the fourteenth apparatus of FIG. 39.

FIGS. 39 and 40 show a fourteenth apparatus in accordance with an exemplary embodiment of the present disclosure, indicated generally at 950. Apparatus 950 is configured as a temperature measurement device configured to measure the temperature of one or more ABTT terminuses 10 and to transmit that information to a separate electronic device. Apparatus 950 is configured to include a nose interface 952, which is configured to be positioned on and supported by nose 26, a transmitter assembly 954 positioned on and supported by nose interface 952, and one or more temperature sensors 956 configured to interface with a respective ABTT terminus 10. Temperature sensors 956 are configured to be connected to transmitter assembly 954 by way of flexible, movable, or positionable supports 958, which are configured to provide movement of each temperature sensor 956 to interface with a respective ABTT terminus 10.

When operating, apparatus 950 receives temperature signals from ABTT terminuses 10 by way of temperature sensors 956. Those signals are transmitted from temperature sensors 956 to transmitter assembly 954, which transmits those signals to a separate electronic device 960, which can be, for example, a cell phone, tablet, laptop, watch, medically enabled appliance, and the like, for analysis, storage, notification, etc.

Figure 41:
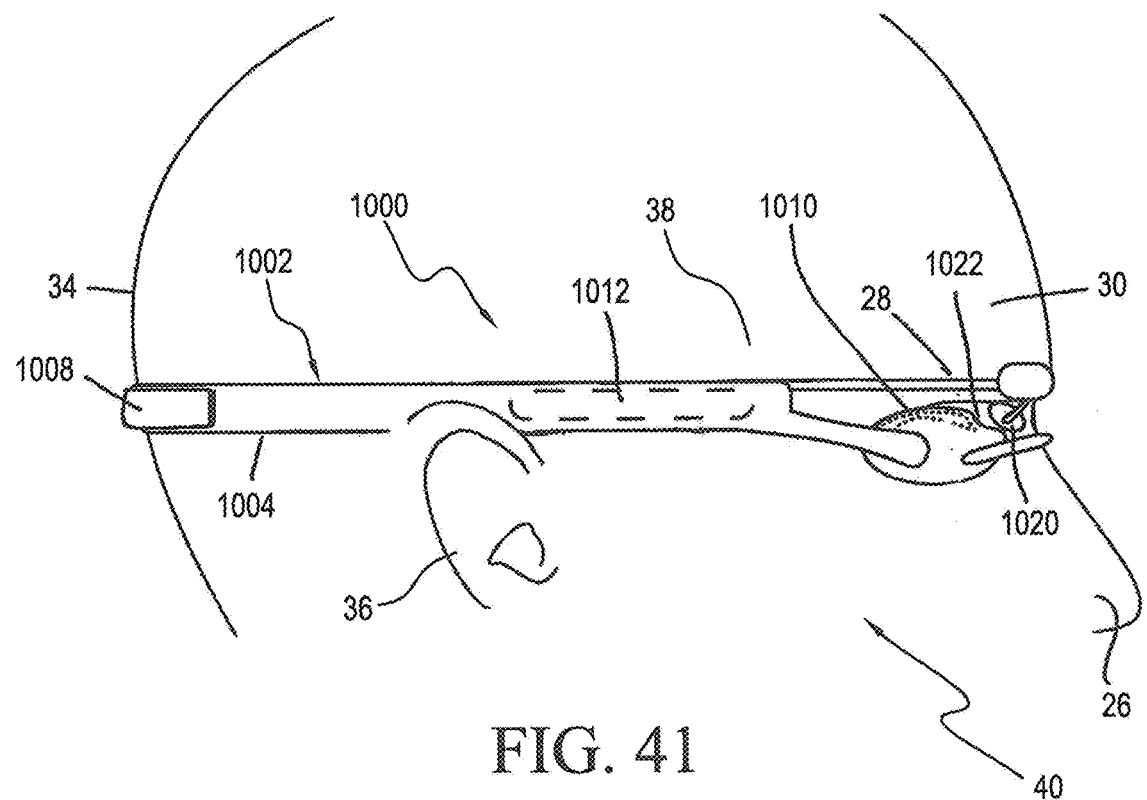
FIG. 41 shows a side view of a fifteenth apparatus in accordance with an exemplary embodiment of the present disclosure.
Figure 42:
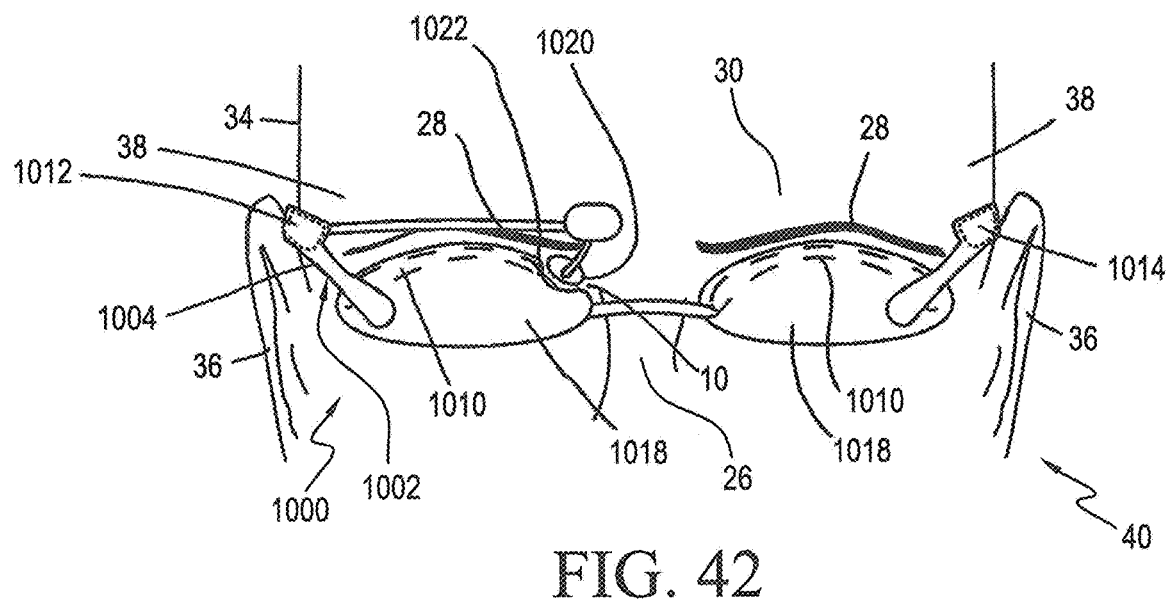
FIG. 42 shows a front view of the fifteenth apparatus of FIG. 41.

FIGS. 41 and 42 show a fifteenth apparatus in accordance with an exemplary embodiment of the present disclosure, indicated generally at 1000. Apparatus 1000 is configured to be positioned and supported on head 34. Such support can include a frictional grip with head 34 by a strap, support by one or more ears 36, and/or support by nose 26. Apparatus 1000 is configured to include a support apparatus 1002, which is configured to include a securing and support strap 1004. Securing and support strap 1004 is further configured with a device or mechanism to secure apparatus 1000 to head 34. For example, securing and support strap 1004 can be configured as an elastic strap that stretches to permit apparatus 1000 to be positioned on and secured to head 34. In another embodiment, securing and support strap 1000 can be configured to include a fastening apparatus 1008, such as a buckle arrangement, or a hook and loop fastening apparatus.

Support apparatus 1002 is configured to locate and position a plurality of elements, such as one or more temperature modification devices 1010, which can be, for example, heating pads, thermoelectric devices, etc., configured and positioned to contact an area of head 34 between eye 32 and eyebrow 28 to provide heating and/or cooling of head 34, a control device 1012, and a power supply/control system 1014 configured to provide power to the electrically operated elements of apparatus 1000 as well as providing control of elements of apparatus 1000, as modified by input to, for example, control device 1012. Control device 1012 can be configured to include one or more control features, such as those shown in FIG. 5. The location of temperature modification device 1010 is such that cooling and/or warming is provided to the blood flowing through the blood vessels in the areas adjacent to temperature modification device 1010, which provides cooling and/or warming to head 34 and, ultimately the brain.

Support apparatus 1002 is configured to support one or more lenses 1018 in a manner of an eyeglasses or sunglasses configuration. Support apparatus is further configured to support one or more temperature sensors 1020, each of which is configured to contact a respective ABTT terminus 10 for receiving temperature signals from ABTT terminus 10. In an exemplary embodiment, each lens 1018 may include a notch, cutout, or recess 1022 to permit temperature sensor 1020 to be located on, over, or adjacent to the skin of ABTT terminus 10. Temperature sensor 1020 can be configured to interface with support apparatus 1002 by way of a support arm 1024 and a flexible, movable, or positionable support 1026, which are configured to allow for adjustment of temperature sensor 1020 for positioning on ABTT terminus 10.

In operation, apparatus 1000 reads the temperature of one or more ABTT terminuses 10 by way of sensor 1020, which transmits signals indicative or representative of the temperature of ABTT terminus 10. Control device 1012 receives the temperature signal, and from the temperature signal determines whether subject or patient 40 needs temperature modification in view of a disease or condition of subject or patient 40. If such treatment is required, as determined by control device 1012 or a separate electronic device (not shown) that communicates with control device 1012, temperature modification device 1010 is actuated to provide heating and/or cooling, with continuous and simultaneous monitoring of the temperature of ABTT terminus 10. The temperature modification continues until the temperature at ABTT terminus 10 reaches a desired value, or until a predetermined time interval passes.

FIGS. 43 to 47 show a sixteenth apparatus in accordance with an exemplary embodiment of the present disclosure, indicated generally at 1100. As shown in FIG. 43, apparatus 1100 is configured as a thin headband 1102 sized and dimensioned to be positioned and supported on head 34. Headband 1102 includes a central front portion 1104 and a central back portion 1106. Central front portion 1104 includes a sensor assembly 1108. Sensor assembly 1108 includes a housing 1110 supported by headband 1102, and an arm 1112 connected to housing 1110. Arm 1112 has at least two positions or orientations with respect to housing 1110. In a first position, arm 1112 is positioned within slot, groove, or opening 1114 located or formed in housing 1110. In a second position, arm 1112 is oriented in a diagonal position at an angle of about 45 degrees in relation to an axis 1116 of headband 1102.

Arm 1112 includes a sensor 1118 positioned at a distal end of arm 1112. Housing 1110 includes a rotatable anchor mechanism 1120, which may be simply described as a hinge, which rotatably connects arm 1112 to housing 1110. Hinge 1120 enables movement of arm 1112 for alignment with ABTT terminus 10. Central back portion 1106 includes a housing 1122, which positions or supports a processor 1124, a transmitter or transceiver 1126, a non-transitory memory 1128, and a power source 1130. Such support can include a frictional grip with head 34 by a strap, support by one or more ears 36, and/or support by nose 26. Thin headband 1102 is configured to secure apparatus 1100 to head 34. Thin headband 1102 can be, for example, an elastic strap that stretches to permit apparatus 1100 to be positioned on and secured to head 34. In another embodiment, thin headband 1102 can include a fastening apparatus 1132, such as a buckle arrangement, or a hook and loop fastening apparatus. FIGS. 44 and 45 show details of housing 1110, including rotatable or movable arm 1112. Movable arm 1112 is preferably made with conformable material such as plastic with memory, wire, bendable metal, and the like, for positioning of sensor 1118 in apposition to ABTT terminus 10. A wire (not shown), preferably a flat cable, connects housing 1110 of central front portion 1104 with central back portion 1106. FIG. 46 shows apparatus 1100 being worn by user 40 with arm 1112 diagonally disposed across the bridge of nose 26 and sensor 1118 aligned with ABTT terminus 10. FIG. 47 shows apparatus 1100 with arm 1112 being worn under eyeglasses 1134.

FIGS. 48 to 51 show a seventeenth apparatus in accordance with an exemplary embodiment of the present disclosure, indicated generally at 1150. As shown in FIG. 48, apparatus 1150 includes a thin headband 1152 sized and dimensioned to be positioned and supported on head 34. Thin headband 1152 includes a central front portion 1154 and a central back portion 1156. Central front portion 1154 includes a sensor assembly 1158. Sensor assembly 1158 includes a housing 1160 supported by headband 1152, and at least one arm 1162 connected or attached to housing 1160. Each arm 1162 is configured to be positioned in a diagonal orientation that can be an angle of about 45 degrees in relation to an axis 1164 of headband 1152. Each arm 1162 includes a sensor 1166 positioned at a distal end of arm 1162. Housing 1160 includes a rotatable anchor mechanism or hinge 1168 that allows motion of arm 1162 for alignment or sensor 1166 with ABTT terminus 10.

Central back portion 1156 includes one or more housings 1170. Housings 1170 can include a processor 1172, a transmitter or transceiver 74, a non-transitory memory 1176, and a power source or supply 1178. The strap of headband 1152 can include a frictional grip with head 34, support by one or more ears 36, and/or support by nose 26. Headband 1152 can also be described as a securing and support strap. Headband 1152 can be configured as an elastic strap that stretches to permit apparatus 1150 to be positioned on and secured to head 34. In another embodiment, headband 1152 can include a fastening apparatus 1180, such as a buckle arrangement or a hook and loop fastening apparatus. FIGS. 48, 49, and 51 are views of apparatus 1150 with two sensors 1166, each secured, attached, or connected by a respective arm 1162 to headband 1152 and being worn by user 40. Each sensor 1166 is configured to measure a biological signal, such as brain temperature and/or glucose. FIG. 50 is a side-view of apparatus 1150 with transmitter 1174 in central back portion 1156 wirelessly connected to a remote device 1182, such as a cell phone. FIG. 51 is a view of 1150 with arms 1162 extending under conventional eyeglasses 1184 in a location that is directly between eyeglasses 1184 and head 34 of user 40, meaning along a line extending from eyeglasses 1184 to head 34.

Figure 52:
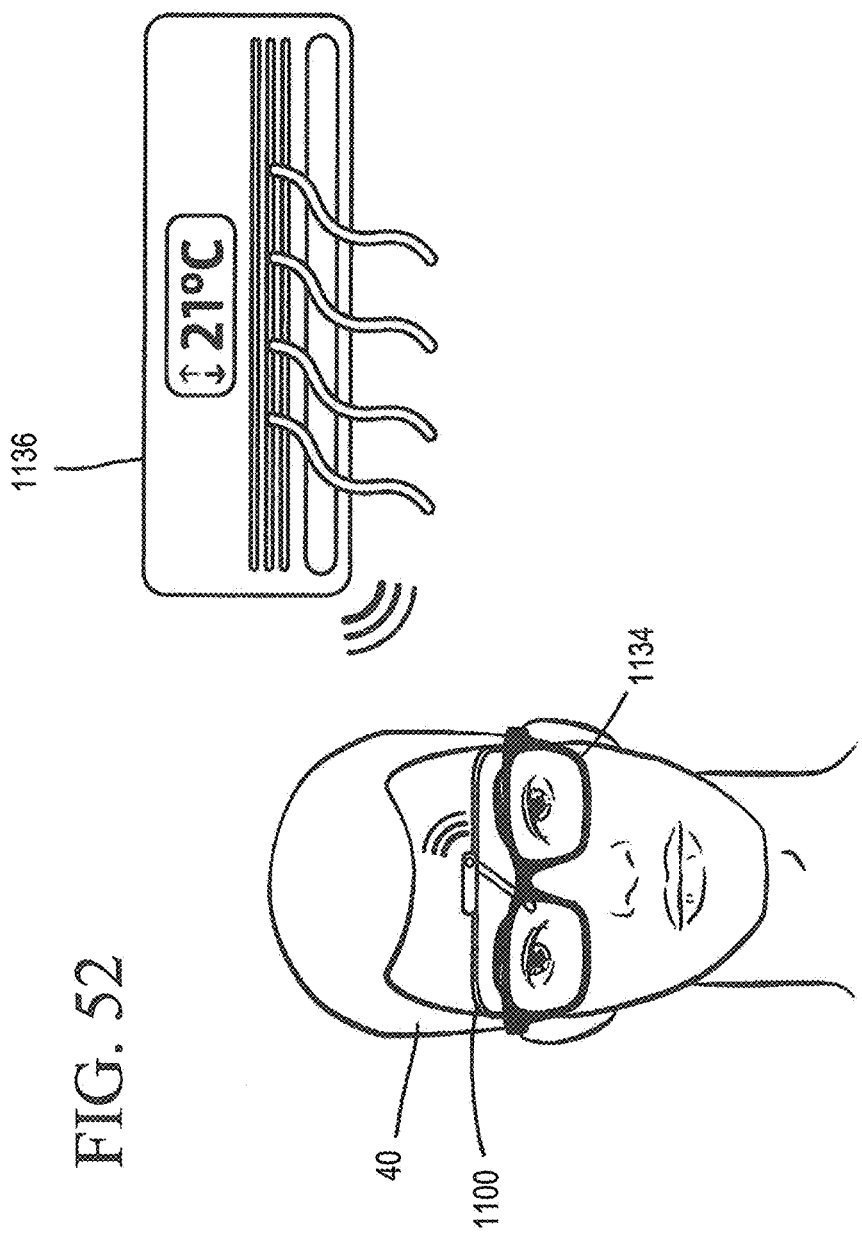
FIG. 52 shows a view of the sixteenth apparatus of FIG. 43 positioned on the head of the user along with eyewear frames, and a remote temperature modification device.

FIG. 52 is a view of apparatus 1100 of FIG. 43 being worn by user 40 with transmitter or transceiver 1126 wirelessly connected and communicating with a remote temperature modification device 1136, exemplified as an air conditioner, for modifying ambient temperature.

Figure 53:
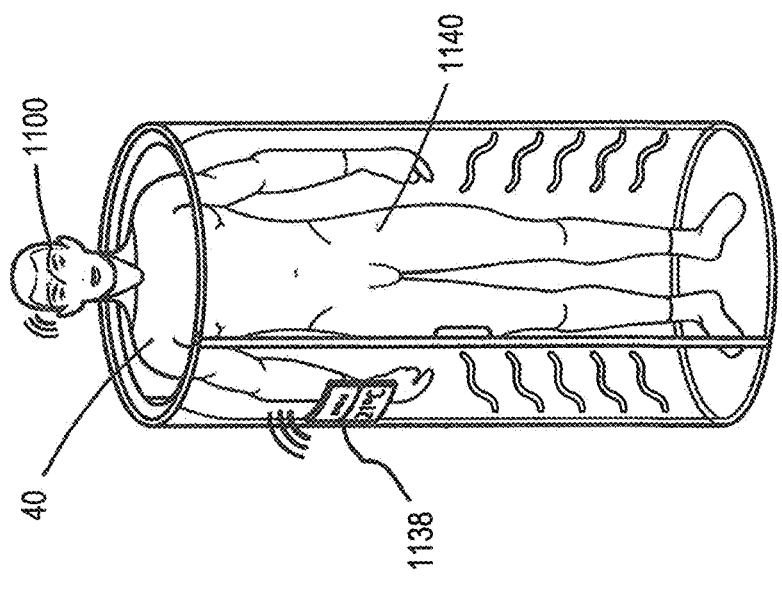
FIG. 53 shows a view of the sixteenth apparatus of FIG. 43 positioned on the head of the user and a remote temperature modification device.

FIG. 53 shows apparatus 1100 of FIG. 43 being worn by user 40 with transmitter or transceiver 1126 wirelessly connected and communicating with a remote temperature modification device 1138, exemplified as a climate chamber, for modifying confined ambient temperature surrounding a body 1140 of user 40.

Figure 54:
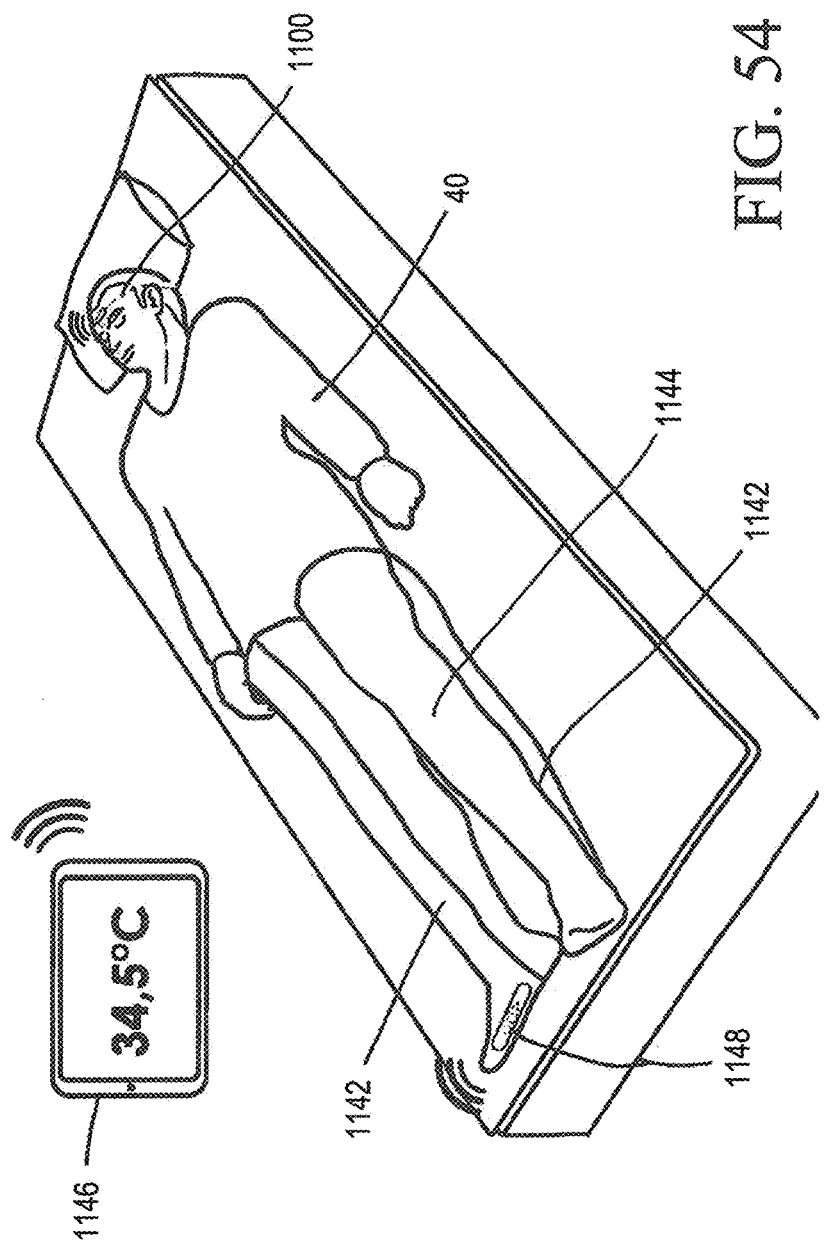
FIG. 54 shows a view of the sixteenth apparatus of FIG. 43 positioned on the head of the user and a separate leg temperature modification device.

FIG. 54 shows a leg temperature modification device 1142 positioned on legs 1144 of user 40. Leg temperature modification device 1142 includes a receiver or transceiver 1148 that communicates with device 1100 by way of signals transmitted wirelessly by transmitter or transceiver 1126, which can be directly from transceiver or transmitter 1126 or by way of a remote electronic device 1146, exemplified as a cell phone. The signals transmitted by apparatus 1100 are analyzed and used to modify the temperature of one or both legs 1144.

Figure 55:
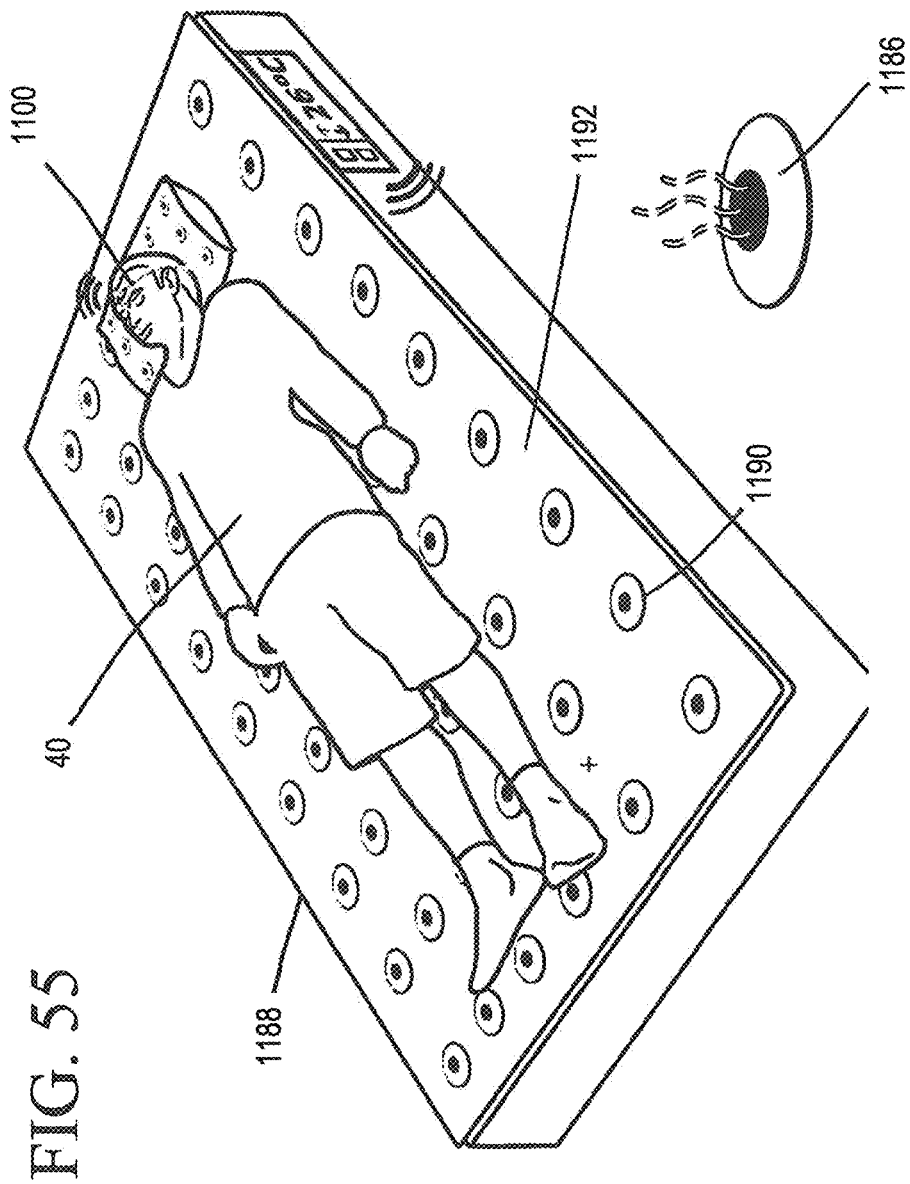
FIG. 55 shows a view of the sixteenth apparatus of FIG. 43 positioned on the head of the user and a separate temperature modification device.

FIG. 55 shows user 40 wearing apparatus 1100 of FIG. 43, with transmitter or transceiver 1126 being wirelessly connected and communicating with a remote external device non-contact temperature modification device 1186, exemplified as an HVAC (heat ventilation air conditioner) device, and also wirelessly communicating with a contact temperature modification device 1188, exemplified as a mattress, mattress 1188 including a plurality of thermoelectric devices 1190 (such as Peltier devices) disposed on a surface 1192 of mattress 1188. In this embodiment processor 1124 in apparatus 1100 is adapted to recruit noncontact temperature modification device 1186 (such as non-contact HVAC) if activation of contact temperature modification device 1188, exemplified as a mattress, does not achieve a target temperature of ABTT terminus 10 sensed by sensor 1118.

Figure 56:
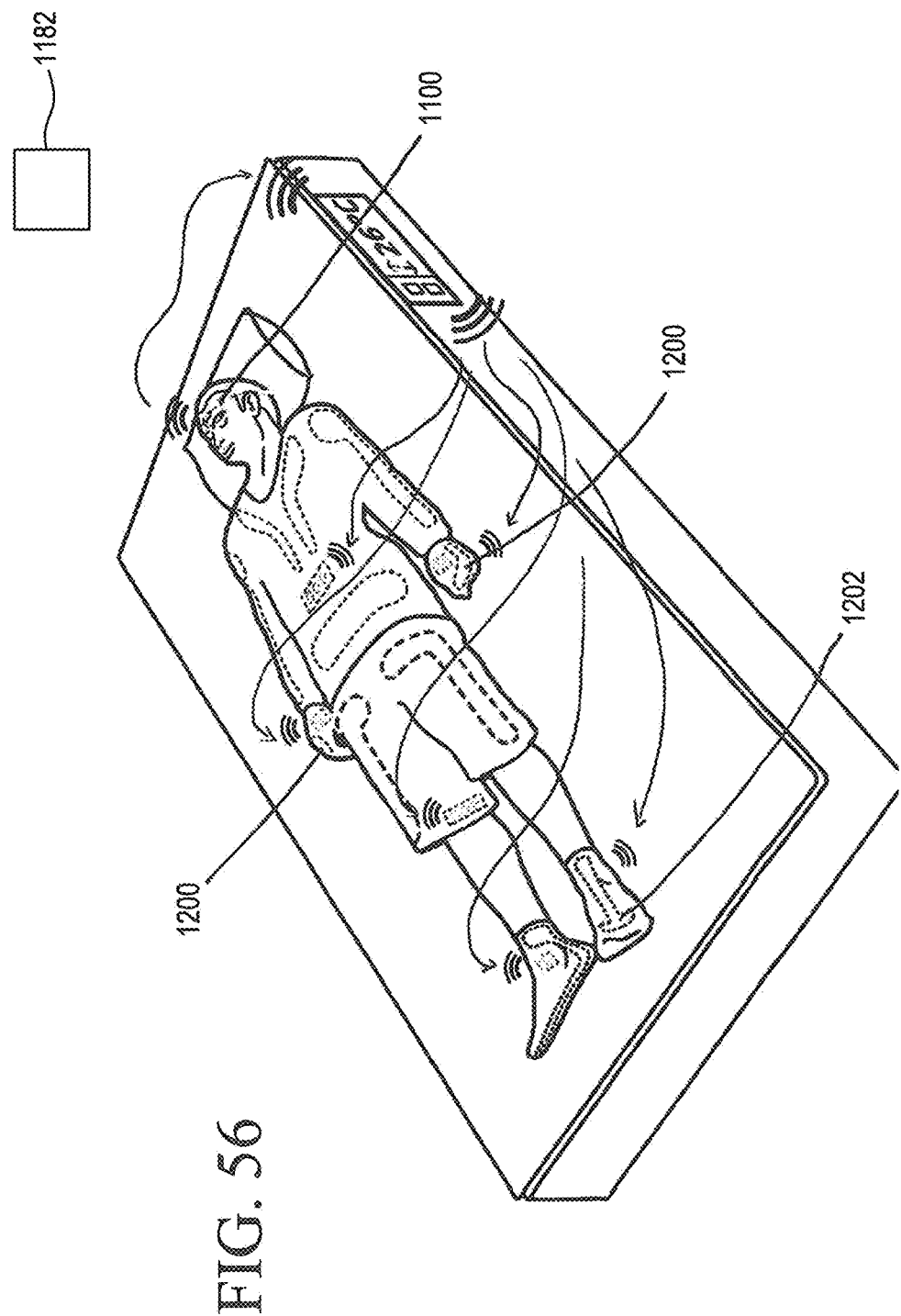
FIG. 56 shows a view of the sixteenth apparatus of FIG. 43 positioned on the head of the user and a plurality of temperature modification devices.

FIG. 56 shows user 40 wearing apparatus 1100 of FIG. 43, and series of body contact temperature modification devices, including hand temperature modification device 1200, feet temperature modification device 1202, arm temperature modification devices 1204, leg temperature modification device 1206, and trunk temperature modification devices 1208. Transmitter or transceiver 1126 of apparatus 1100 is wirelessly connected and communicates with a remote external device 1182, such as a cell phone, and to a second contact temperature modification device 1188, exemplified as a mattress, mattress 1188 including a plurality of thermoelectric devices 1190, such as those shown in FIG. 55, disposed on 1192 surface of mattress 1188. In this embodiment processor 1124 in apparatus 1100 is adapted to recruit second temperature modification device 1188 (such as mattress 1188) if activation of body contact temperature modification devices 1200, 1202, 1204, 1206, and 1208 do not achieve a target temperature of ABTT terminus 10 sensed by sensor 1118.

Figure 57:
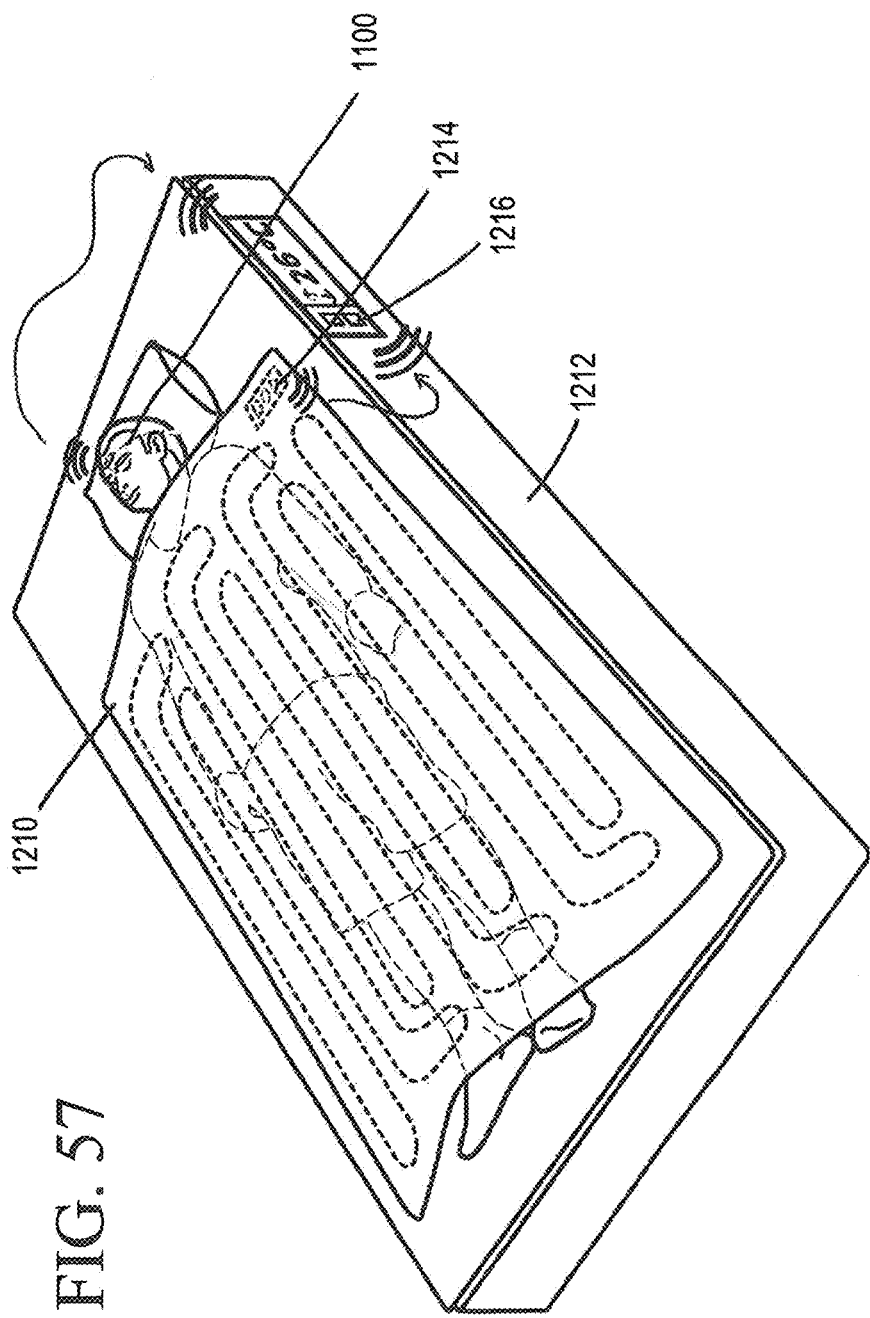
FIG. 57 shows a view of the sixteenth apparatus of FIG. 43 positioned on the head of the user and a plurality of temperature modification devices.

FIG. 57 shows user 40 wearing apparatus 1100 of FIG. 43, and being in contact with a first body contact temperature modification device 1210, exemplified as a blanket, and being in contact with a second body contact temperature modification device 1212, exemplified as a mattress. Apparatus 1100 is wirelessly connected to and communications with first body contact temperature modification device 1210 and with second body contact temperature modification device 1212 by way of transmitter or transceiver 1126. First body contact temperature modification device 1210 includes a receiver, transmitter, or transceiver 1214 and second body contact temperature modification device 1212 includes a receiver, transmitter or transceiver 1216, and receiver, transmitter or transceiver 1214 of first body contact temperature modification device 1210 and receiver, transmitter or transceiver 1216 of second body contact temperature modification device 1212 being operatively coupled with transmitter or transceiver 1126. In this embodiment, processor 1124 in apparatus 1100 is adapted to recruit second temperature modification device 1212 (such as mattress 1212) if activation of first body contact temperature modification device 1210 (such as blanket 1210) does not achieve a target temperature of ABTT terminus 10 as sensed by sensor 1118.

Figure 59:
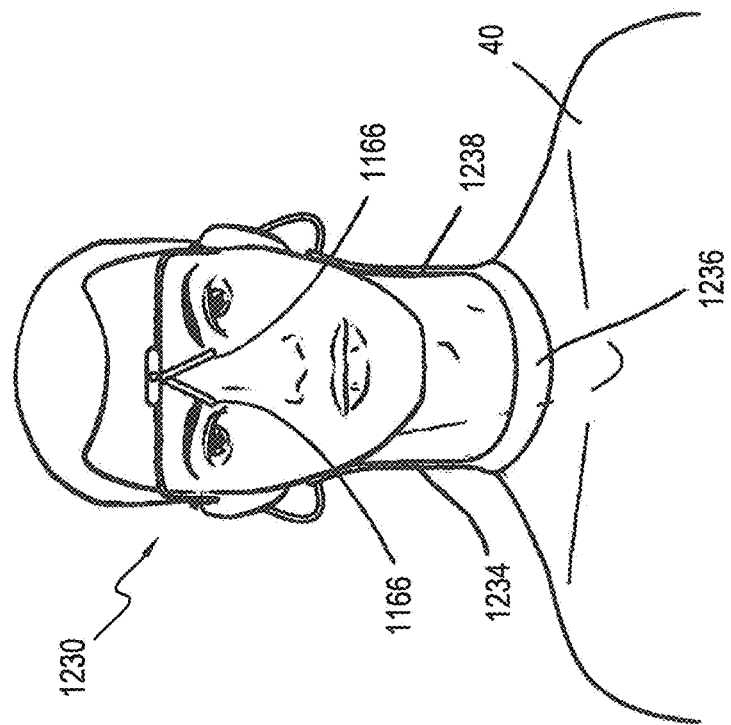
FIG. 59 shows another view of the eighteenth apparatus of FIG. 58.
Figure 58:
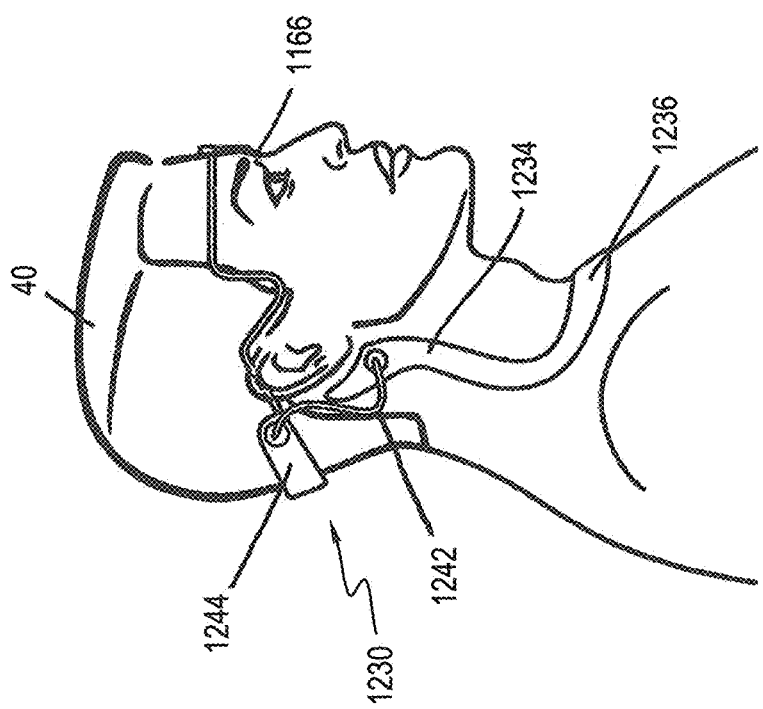
FIG. 58 shows a view of an eighteenth apparatus in accordance with an exemplary embodiment of the present disclosure.

FIGS. 58 and 59 show views of an eighteenth apparatus in accordance with an exemplary embodiment of the present disclosure, indicated generally at 1230. As shown in FIG. 58, apparatus 1230 includes a plurality of sensors 1166, as shown in FIG. 48, a temperature modification device 1232, and a monitoring device or apparatus 1244. Temperature modification device 1232 includes three portions: a right carotid portion 1234, a mid-subclavian portion 1236, and a left carotid portion 1238. Temperature modification device 1232 is connected or attached to monitoring device 1244 by a detachable wire or cable 1242.

Figures 60, 61, 62:
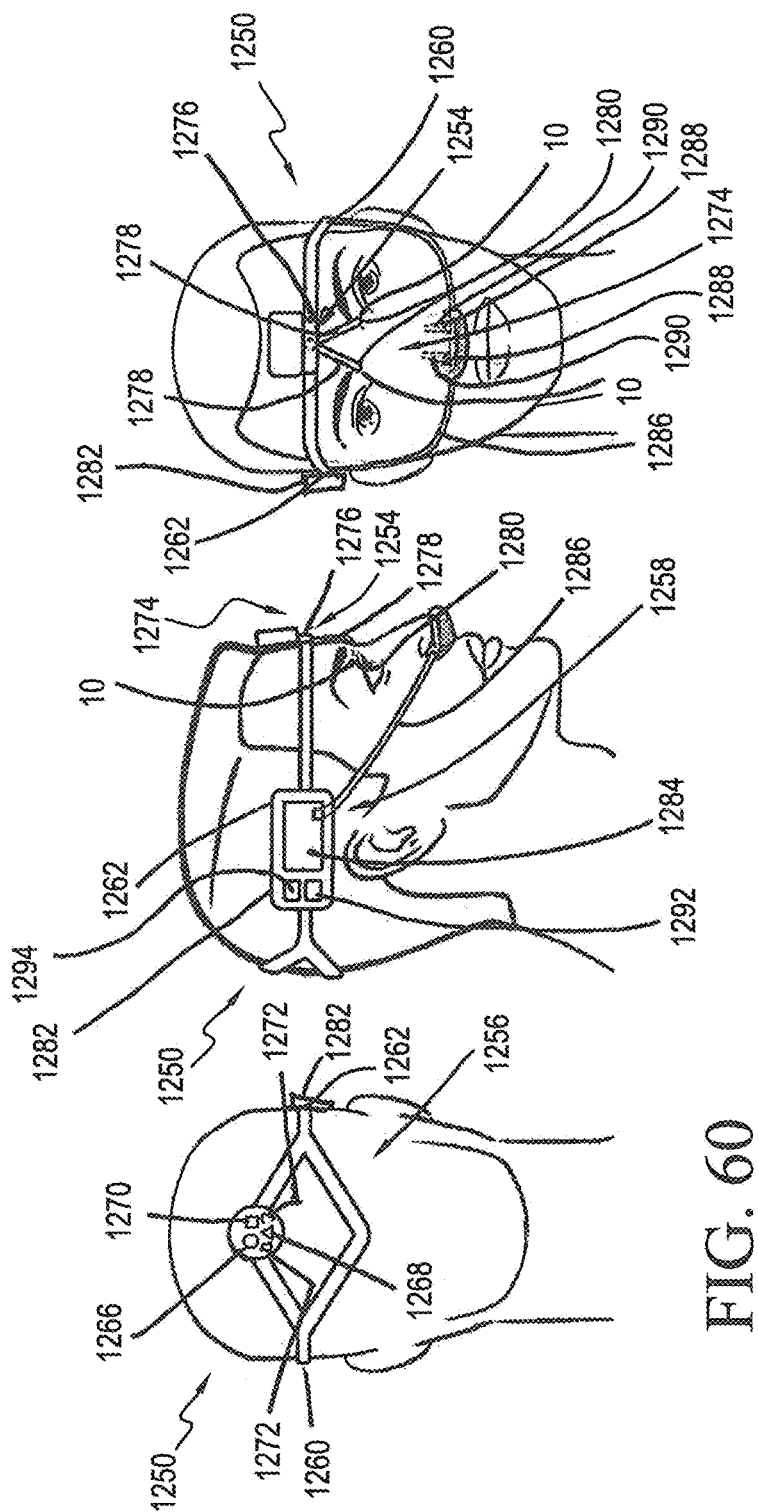
FIG. 60 shows a view of a nineteenth apparatus in accordance with an exemplary embodiment of the present disclosure.
FIG. 61 shows another view of the nineteenth apparatus of FIG. 60.
FIG. 62 shows a further view of the nineteenth apparatus of FIG. 60.

FIGS. 60 TO 62 show views of a nineteenth apparatus in accordance with an exemplary embodiment of the present disclosure, indicated generally at 1250, configured as a headband. As shown in FIGS. 61 and 62, apparatus 1250 includes a combination of features of seventeenth apparatus 1150, as shown in FIG. 48, and a temperature modification device 1252. Apparatus 1250 includes a central front portion 1254, a central back portion 1256, and a side portion 1254. Side portion 1254 is divided into a left side portion 1260 and a right side portion 1262. Central back portion 1254 includes a housing 1276 in which are located a processor 1266, a transmitter or transceiver 1268, a non-transitory memory 1270, and a power source or supply 1272. Central front portion 1254 includes a sensor assembly 1274. Sensor assembly 1274 includes a housing 1276 supported by headband 1250, and at least one arm 1278 connected to housing 1276. Each arm 1278 supports a sensor 1280 sized and dimensioned to interface or be positioned on or at ABTT terminus 10. Right side portion 1262 includes a housing 1282. Housing 1282 includes a reservoir 1284 for a fluid, such as water. Reservoir 1284 being connected by a tube 1286 to a nozzle 1288 for spraying or delivering fluid to nasal cavity 1290, for cooling or warming up brain core 24. Housing 1282, besides containing reservoir 1284, can include a motor or pump 1292 and electronics 1294 for executing operations and instructions for motor or pump 1292, electronics 1294 being connected to processor 1266 and other electronics of central back portion 1256.

FIGS. 62 to 65 show views of a twentieth apparatus in accordance with an exemplary embodiment of the present disclosure, indicated generally at 1300. Apparatus 1300 is a thin headband sized and dimensioned to be positioned and supported on head 34. Apparatus 1300 includes a central front portion 1302 and a central back portion 1304. Central front portion 1302 includes a sensor assembly 1306. Sensor assembly 1306 includes a housing 1308 supported by headband 1300, a right arm 1310, and a left arm 1312. Right arm 1310 and left arm 1312 are sized and dimensioned to be positioned at ABTT terminus 10. Each arm 1310 and 1312 includes a plurality of sensors 1314 positioned in or on each arm 1310 and 1312. Sensors 1314 can be, for example, a light emitter-light detector pair, infrared sensors, thermal sensors, chemical sensors, and the like. Central back portion 1304 includes a housing 1316 in which are positioned a processor 1318, a transmitter or transceiver 1320, a non-transitory memory 1322, and a power source or supply 1324. Transmitter or transceiver 1320 is configured to wirelessly connect to or communication with a remote device 1326, such as a cell phone, tablet, computer, radio, and the like.

FIG. 66 shows a twenty-first apparatus in accordance with an exemplary embodiment of the present disclosure, indicated generally at 1330. Apparatus 1330 includes similarities to apparatus 1300 of FIG. 63, and similar features are similarly labelled. In contrast to apparatus 1300, apparatus 1330 includes one adjustable arm 1310 and a single sensor, such as sensor 1166 shown in FIG. 48. It should also be observed that central front portion 1302 shown in FIG. 66 includes the features of central back portion 1304 shown in FIG. 63.

FIGS. 67 to 69 show view of a twenty-second apparatus in accordance with an exemplary embodiment of the present disclosure, indicated generally at 1340. The features of apparatus 1340 are generally similar to the features of twentieth apparatus 1300, and apparatus 1340 is therefore similarly labelled. However, twenty-second apparatus 1340 also includes an additional strap 1342 in a back portion 1344.

FIG. 70 shows a view of a twenty-third apparatus in accordance with an exemplary embodiment of the present disclosure, indicated generally at 1350. Twenty-third apparatus 1350 is similar in some respects to twenty-first apparatus 1330 shown in FIG. 66, and is similarly labelled where appropriate. Apparatus 1350 includes a recess portion 1352, which is sized and dimensioned to receive a housing 1354. Housing 1354 includes a processor 1356, a transmitter or transceiver 1358, a non-transitory memory 1360, and a power source or supply 1362. Transmitter or transceiver 1358 is configured to communicate wirelessly with remote device 1326, such as a cell phone, tablet, computer, radio, and the like.

FIGS. 71 and 72 show views of a twenty-fourth apparatus in accordance with an exemplary embodiment of the present disclosure, indicated generally at 1370. Apparatus 1370 is similar in certain aspects to twentieth apparatus 1300 shown in FIG. 63, and apparatus 1370 is similarly labelled where appropriate. Twenty-fourth apparatus 1370 includes a movable housing 1372. Movable housing 1372 is sized and dimensioned to interface and be supported by a groove 1374 formed in apparatus 1370. Thus, housing 1372 is movable or positionable along groove 1374. Groove 1374 includes a wire 1376, and housing 1372 is electrically connected to wire 76 when housing 1372 is positioned in groove 1374. Transmitter or transceiver 1320 in movable housing 1372 wirelessly communicates with remote device 1326, such as a cell phone, tablet, computer, radio, and the like. In this embodiment, user 40 can position housing 1372 in a location along apparatus 1370 that would be more comfortable such as for sleeping or in another location more cosmetically attractive when using outdoors for sports use for example.

FIG. 73 shows a view of a twenty-fifth apparatus in accordance with an exemplary embodiment of the present disclosure, indicated generally at 1380. Twenty-fifth apparatus 1380 includes certain elements that are similar to elements of sixteenth apparatus 1100, and where such elements exist they are similarly labelled. Twenty-fifth apparatus 1380 includes two arms 1382, each of which includes a non-contact sensor 1384. FIG. 75 is a close-up view of non-contact sensor 1384, which can be, for example, an infrared sensor. FIG. 76 shows arm 1382, which includes a recess 1386, and infrared sensor 1384 is positioned within recess 1386.

FIGS. 74 and 77 show views of a twenty-sixth apparatus in accordance with an exemplary embodiment of the present disclosure, indicated generally at 1390. Apparatus 1390 includes sensor assembly 1158 from FIG. 48, and a temperature modification assembly 1392. Temperature modification assembly 1392 includes a nose support portion 1394, which supports a receiver or transceiver 1396, a right temperature modification device 1398, and a left temperature modification device 1400. Right temperature modification device 1398 and left temperature modification device 1400 extend along respective sides of nose 26. Right temperature modification device 1398 and left temperature modification device 1400 are each positioned at least partially along facial vein 22 and angular vein 20, which carry blood toward the brain via superior ophthalmic vein 23 and orbital veins. Right temperature modification device 1398 and left temperature modification device 1400 are adapted to heat or cool the skin and underlying facial veins 22 and angular veins 20, thereby bringing hot or cold blood into the brain. Sensor assembly 1158 communicates with and sends signals to a transmitter or transceiver 1402 wirelessly connected to receiver or transceiver 1396 of temperature modification assembly 1392.

FIGS. 78 to 80 show views of a twenty-seventh apparatus in accordance with an exemplary embodiment of the present disclosure, indicated generally at 1410. Twenty-seventh apparatus 1410 represents an alternative embodiment to seventeenth apparatus 1150 of FIGS. 48 and 49. Apparatus 1410 includes an approximately one fourth circle headband

1412. Headband 1412 includes a frontal portion 1414 and an ear support portion 1416. As shown in FIG. 78, apparatus 1410 is configured to include thin one fourth headband 1412 that is sized and dimensioned to be positioned and supported on head 34 by ear support portion 1416 and a sensor assembly 1418 formed as part of frontal portion 1414. Thin one fourth headband 1412 is preferably made out of conformable material adapted by pressure and apposition to the skin to secure apparatus 1410 to head 34. Thin one fourth headband 1412 preferably has a curved area 1420 to increase frictional grip of apparatus 1410 with the skin, and thereby achieve better fixation and support of apparatus 1410 to head 34. Frontal portion 1414 includes a screen 1420. Sensor assembly 1418 includes a housing 1424 and an arm 1426 connected to housing 1424 positioned in a diagonal orientation at an angle of about 45 degrees in relation to an axis of the thin one fourth headband 1412. Arm 1426 includes a nose support portion 1428 to secure arm 1426 to nose 26. A cord 1430 of an ear bud or ear phone 1432 is removably attached to ear support portion 1416. Arm 1426 includes a sensor 1434 positioned at a distal end of arm 1426d. Ear supported portion 1416 includes ear bud or ear phone 1432, a microphone 1436, and a housing 1438, housing 1438 including and supporting a processor 1440, transmitter or transceiver 1442, a non-transitory memory 1444, and a power source or supply (not shown). Ear bud or ear phone 1432, which is shown in FIGS. 79 and 80 as positioned on the right side of user 40, can include a left ear bud 1446 for interacting with left ear 36. Transmitter or transceiver 1442 of apparatus 1410 wirelessly connects to or communicates with remote device 1182, such as cell phone, remote device 1182 including a display 1448 and being adapted to receive signals transmitted by sensor 1434. Device 1182 can display measurements from sensor 1434 and simultaneously display advertising on display 1448. It should be understood that any of the temperature modification devices of the present disclosure can be connected by wire or by wireless means to apparatus 1410, and thin one fourth headband 1412 or ear support portion 1416 can include a port or electrical connector (not shown). FIGS. 79 and 80 further show views of user 40 wearing apparatus 1410.

FIGS. 81 to 83 show a twenty-eighth apparatus in accordance with an exemplary embodiment of the present disclosure, indicated generally at 1460. As shown in FIGS. 81 and 83, apparatus 1460 is configured as a combination of a sensor assembly 1462, sensor assembly 1462 configured to include a sensing nose clip 1464 and a temperature modification device 1466 configured as a mask. It should be understood that sensor assembly 1462, as well as other sensor assemblies described herein, can be called monitor assemblies or devices since sensor assembly 1462 monitors signals from ABTT terminus 10. Sensing nose clip 1464 includes a nose portion 1480 for securing to nose 26, and a housing 1468, which includes or supports a processor (not shown), a transmitter or transceiver (not shown), a non-transitory memory (not shown), and power source (not shown). Apparatus 1460 includes a sensor assembly 1470, sensor assembly 1470 including a right adjustable arm 1472 and a left adjustable arm 1474, right adjustable arm 1472 and left adjustable arm 1474 including a right sensor 1476 and a left sensor 1478 disposed, respectively, along right adjustable arm 1472 and left adjustable arm 1474. Temperature modification device 1466 configured as a mask includes electronics 1482 (including a receiver) and a reservoir 1484 including a fluid 1486 and thermoelectric devices 1488 to warm or cool fluid 1486, reservoir 1484 associated with a fluid pump (not shown) to release fluid 1486 according to a signal received from sensing nose clip 1464.

Figure 85:
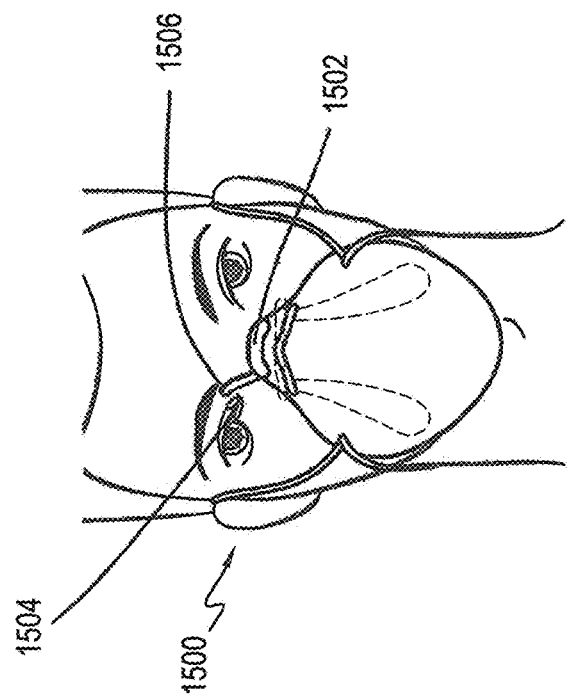
FIG. 85 shows another view of the twenty-ninth apparatus of FIG. 84.
Figure 84:
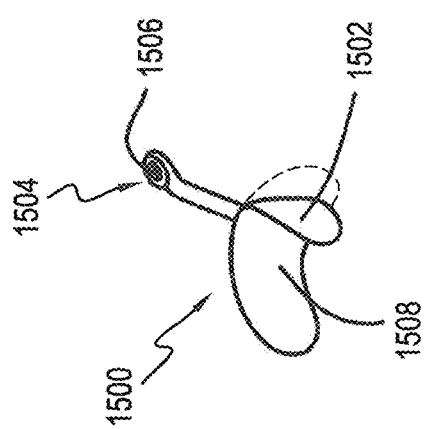
FIG. 84 shows a view of a twenty-ninth apparatus in accordance with an exemplary embodiment of the present disclosure.

FIGS. 84 and 85 show views of a twenty-ninth apparatus in accordance with an exemplary embodiment of the present disclosure, indicated generally at 1500, which is an alternative embodiment to the twenty-eighth apparatus 1460 of FIGS. 81-83. Apparatus 1500 includes a nose clip 1502 that includes one sensor assembly 1504 that includes one sensor 1506 and an adhesive surface 1508 for securing nose clip 1502 to the skin.

FIG. 88 shows a view of a thirtieth apparatus in accordance with an exemplary embodiment of the present disclosure, indicated generally at 1510, which is an alternative embodiment of FIG. 81 configured as a sensing nose clip 1510 including three portions: a central portion 1512 that includes a processor 1514, a transmitter or transceiver 1516, a non-transitory memory 1518, and a power source 1520, and two side portions, namely, a right adjustable arm 1522 and a left adjustable arm 1524, right adjustable arm 1522 and left adjustable arm 1524 including a right sensor 1526 and a left sensor 1528 disposed, respectively, at the end of right adjustable arm 1522 and left adjustable arm 1524. FIG. 87 shows sensing nose clip of FIG. 88 being anchored to a goggle or a mask 1530, sensing nose clip 1510 being wirelessly connected to a remote device 1182, such as a watch, tablet, computer, phone, and the like. FIG. 86 shows user 40 wearing sensing nose clip 1510 and goggle or mask 1530.

Figure 89:
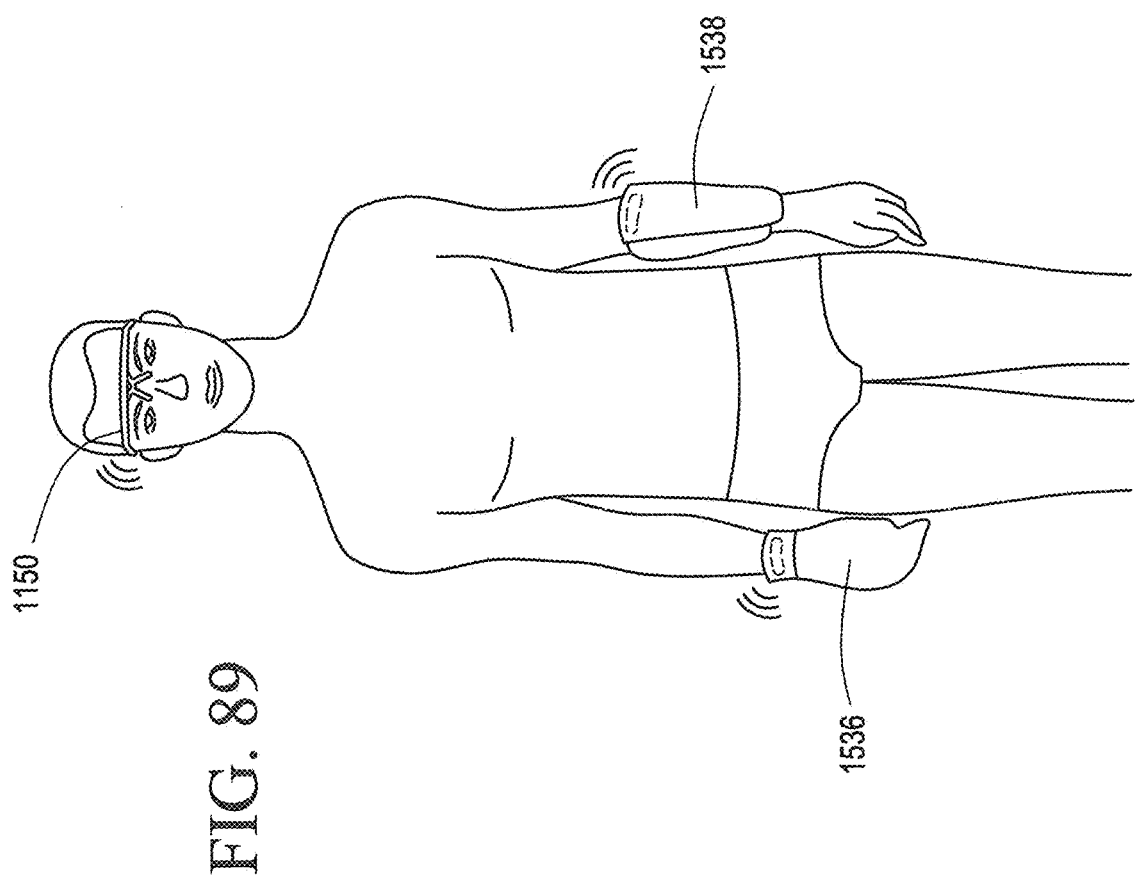
FIG. 89 shows a view of the seventeenth apparatus of FIG. 48 worn in conjunction with a plurality of temperature modification devices.

FIG. 89 shows seventeenth apparatus 1150 of FIG. 48 being wirelessly connected to a hand temperature modification device 1536 and a forearm temperature modification device 1538.

FIGS. 90 and 91 show views of a temperature modification device 1540 including three (3) portions: a central portion 1542 including processor 1514, transmitter, receiver, or transceiver 1516, non-transitory memory 1518, and power source 1520, and two side portions, namely, a right carotid portion 1544 and a left carotid portion 1544, right carotid portion 1544 and left carotid portion 1544, being adapted to align with the right carotid artery and the left carotid artery, right carotid portion 1544 including a plurality of thermoelectric devices 1546 and left carotid portion 1544 including a plurality of thermoelectric devices 1546. Central portion 1542 has a malleable and/or conformable material with memory for alignment with the carotid arteries and securing temperature modification device 1540 to neck 42. Transmitter, receiver, or transceiver 1516 is wirelessly connected to remote device 1182 including a monitoring device or sensing device of the present disclosure or a cell phone, watch, tablet, computer, and the like. FIG. 90 shows the embodiment of FIG. 91 including an adhesive surface 1548 and an adhesive backing 1550.

Figure 92:
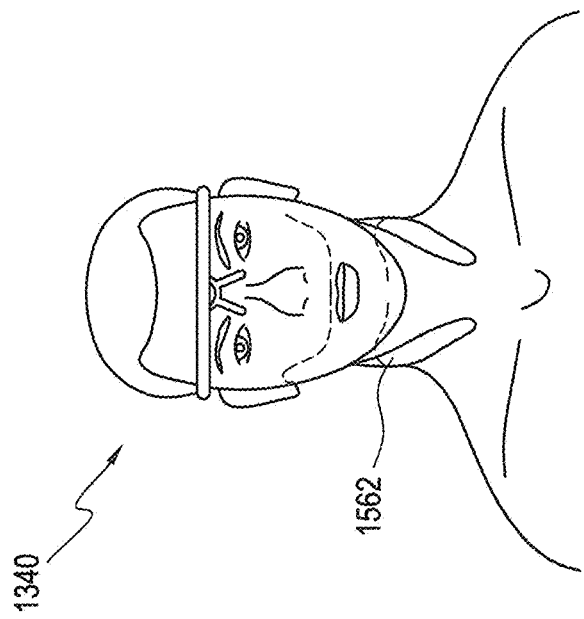
FIG. 92 shows a view of a thirty-first apparatus in accordance with an exemplary embodiment of the present disclosure.
Figure 94:
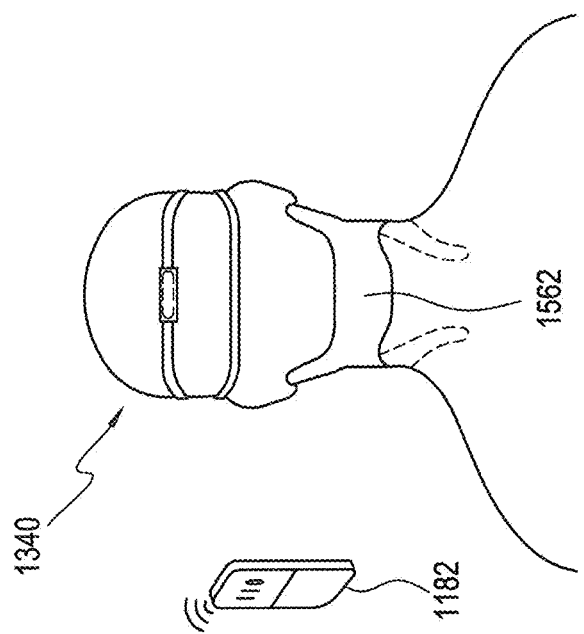
FIG. 94 shows a further view of the thirty-first apparatus of FIG. 92.
Figure 93:
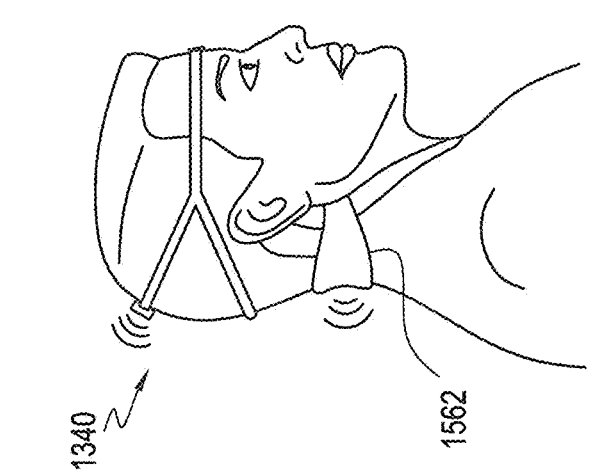
FIG. 93 shows another view of the thirty-first apparatus of FIG. 92.

FIGS. 92-94 show views of a thirty-first apparatus 1560 configured as a combination of twenty-second apparatus 1340, as shown in FIG. 68, and a temperature modification device 1562. FIG. 93 shows user 40 wearing thirty-first apparatus 1560, with wireless communication between twenty-second apparatus 1340 and temperature modification device 1562, and further connecting wirelessly to remote device 1182, such as a cell phone and the like.

FIGS. 95-97 show views of a thirty-second apparatus in accordance with an exemplary embodiment of the present disclosure, indicated generally at 1570. Apparatus 1570 includes twenty-second apparatus 1340, as shown in FIG. 68 and a temperature modification device 1572, including three portions: a central portion 1573 including processor 1514, transmitter, receiver, or transceiver 1516, non-transitory memory 1518, and power source 1520, and two side portions, namely, a right carotid portion 1576 and a left carotid portion 1578, right carotid portion 1576 including a right loop 1580 at its end, and left carotid portion 1578 including a left loop 1580 at its end, right loop 1580 and left loop 1580 being adapted to anchor on a temple 1582 of an eyewear or a frame 1584. FIG. 95 shows user 40 wearing apparatus 1340, temperature modification device 1572, and eyewear or frame 1584. Apparatus 1340 is wirelessly connected to temperature modification device 1572, and to remote device 1182, such as a cell phone and the like.

FIG. 98 shows a temperature modification device 1590 including a main body 1592 made out of conformable material with memory and including a right area 1594 and a left area 1596 of frictional grip, main body 1592 including three (3) portions: a central portion 1598 including processor 1514, transmitter, receiver, or transceiver 1516, non-transitory memory 1518, and power source 1520, and two side portions, namely, a right carotid portion 1600 and a left carotid portion 1602, right carotid portion 1600 and left carotid portion 1602 being adapted to align with the right carotid artery and the left carotid artery, right carotid portion 1600 including a plurality of thermoelectric devices 1604 and left carotid portion 1602 including a plurality of thermoelectric devices 1604. Right carotid portion 1600 and left carotid portion 1602 preferably includes a malleable and/or conformable material with memory for alignment with the carotid arteries and securing temperature modification device 1590 to neck 42. Transmitter, receiver, or transceiver 1516 is wirelessly connected to remote device 1182 including a monitoring device or sensing device of the present disclosure or a watch, tablet, computer, phone and the like. FIGS. 99-101 show views of user 40 wearing temperature modification device 1590 with twenty-second apparatus 1340.

Figure 102:
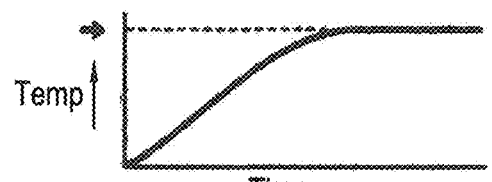
FIG. 102 shows a first pattern of temperature modification in accordance with an exemplary embodiment of the present disclosure.
Figure 103:
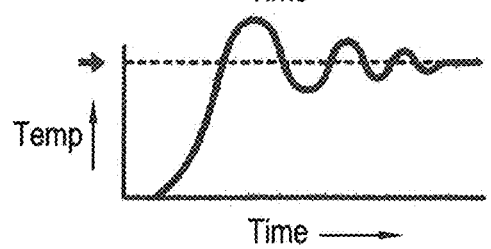
FIG. 103 shows a second pattern of temperature modification in accordance with an exemplary embodiment of the present disclosure.
Figure 104:
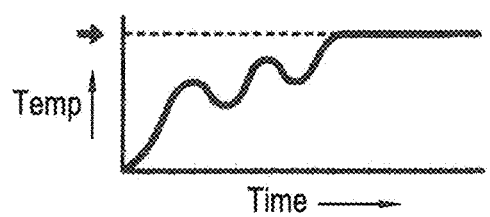
FIG. 104 shows a third pattern of temperature modification in accordance with an exemplary embodiment of the present disclosure.

FIGS. 102-104 show views of different patterns of temperature modification of a temperature modification device based on a signal received from a sensor from a monitoring device or sensing device. FIG. 102 shows an exemplary pattern of modification during sleep that has a gradual and relatively slow change in temperature. FIG. 103 shows an exemplary pattern of modification during an urgent situation such as treating severe hypothermia with more rapid increase of temperature, and even overshooting, or alternatively to treat heatstroke (not shown) that has a similar pattern but inverse pattern with more rapid decrease of temperature of the thermoelectric devices. FIG. 104 shows an exemplary pattern of modification during a situation that requires a consistent and gradual but more intense increase in temperature such as during climbing in a cold weather for warming up, or alternatively during physical activity in hot weather (not shown) that has a similar pattern but inverse pattern with consistent and gradual but more intense decrease in temperature of the thermoelectric devices.

Figure 105:
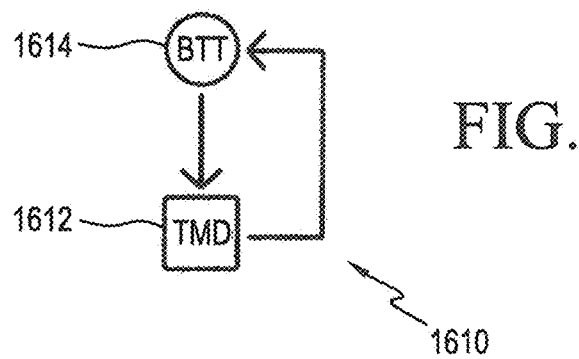
FIG. 105 shows a feed-back loop in accordance with an exemplary embodiment of the present disclosure.

FIG. 105 shows an exemplary feed-back loop control system 1610 between a temperature modification device (TMD) 1612 and a sensor assembly 1614, represented as an ABTT monitoring or sensing device or assembly. ABTT terminus 10 provides an input signal to TMD 1612, which generates an output signal that is fed into ABTT terminus 10, which in turn transmits a signal to sensor assembly 1614. The signal from sensor assembly 1614 is analyzed to create a new input signal, which is transmitted as a new input signal to TMD 1612.

Figure 106:
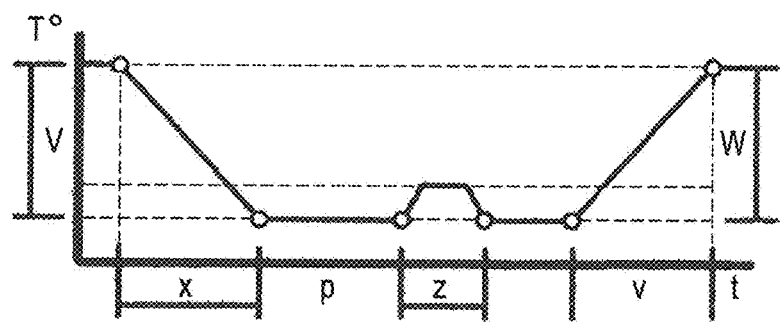
FIG. 106 shows a feed-back control during sleep in accordance with an exemplary embodiment of the present disclosure.

FIG. 106 shows an exemplary feed-back control system during sleep, in which a processor in the monitoring sensing device has a target pattern, target pattern includes decrease of temperature "Y" after a subject has slept for a period of time "x," which is an exemplary sleep induction phase. This period is followed by a second phase of stable temperature "p," followed by a slight temperature elevation for a period of time "z," which is followed by increase of temperature "w" for a period of time "v," corresponding to awakening. Any departure for this thermal pattern is corrected by instructions transmitted from the processor to TMD 1612 by increasing or decreasing the temperature of TMD 1612 for a specific period of time.

Figure 107:
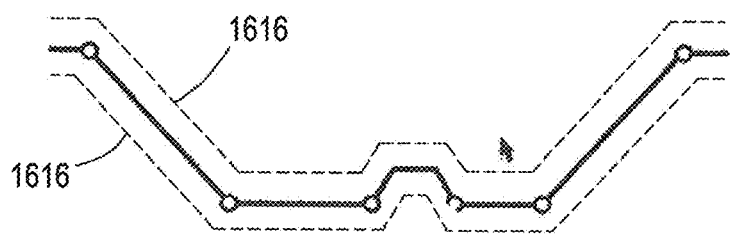
FIG. 107 shows a deviation from a target pattern in accordance with an exemplary embodiment of the present disclosure.

FIG. 107 shows an exemplary acceptable range of plus or minus deviation 1616 from the target pattern. The preferred plus minus deviation 1616 is 0.4 degrees Celsius, is more preferably 0.3 degrees Celsius, is even more preferably 0.2 degrees Celsius, is yet more preferably 0.1 degrees Celsius, and is most preferably 0.05 degrees Celsius.

Figure 108:
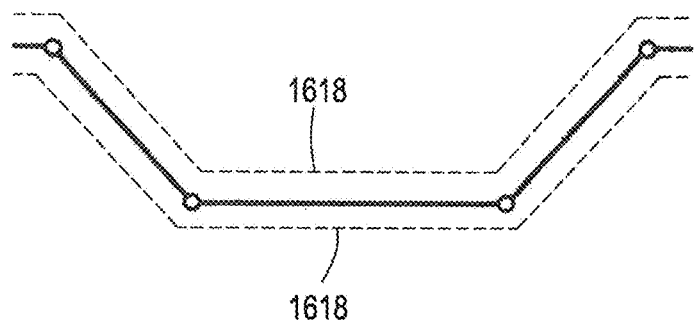
FIG. 108 shows another deviation from a target pattern in accordance with an exemplary embodiment of the present disclosure.

FIG. 108 shows an exemplary acceptable range of plus or minus deviation 1618 from the target pattern, as found for example during a surgical procedure.

FIGS. 109-111 show another apparatus in accordance with an exemplary embodiment of the present disclosure, indicated generally at 1630. As shown in FIGS. 110 and 111, apparatus 1630 is configured as a combination of a sensor assembly 1632, configured as a goggle or goggle frame 1634 and a temperature modification device (TMD) 1636, sensor assembly 1632 including a cable 1638 and connector 1640 passing along the back of neck 42 to electrically connect with TMD 1636 similar to temperature modification device 1540 of FIG. 91. TMD 1636 includes a port or an electrical connection 1642 adapted to receive cable 1638 from sensor assembly 1632.

Figure 112:
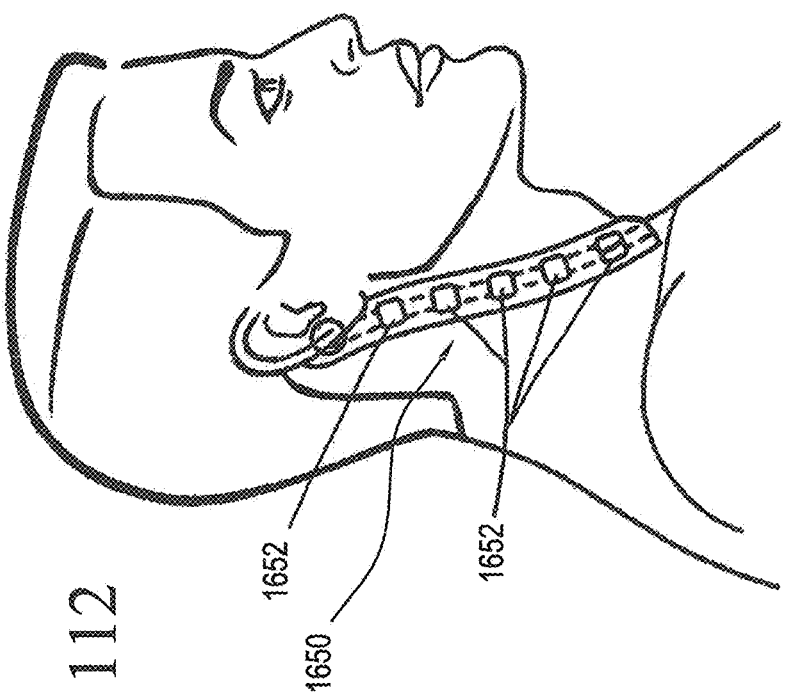
FIG. 112 is a view of a temperature modification device in accordance with an exemplary embodiment of the present disclosure.

FIG. 112 shows a temperature modification device (TMD) 1650 in accordance with an exemplary embodiment of the present disclosure aligned with the carotid artery and retroauricular area, TMD 1650 including a plurality of thermoelectric devices 1652.

Figure 113:
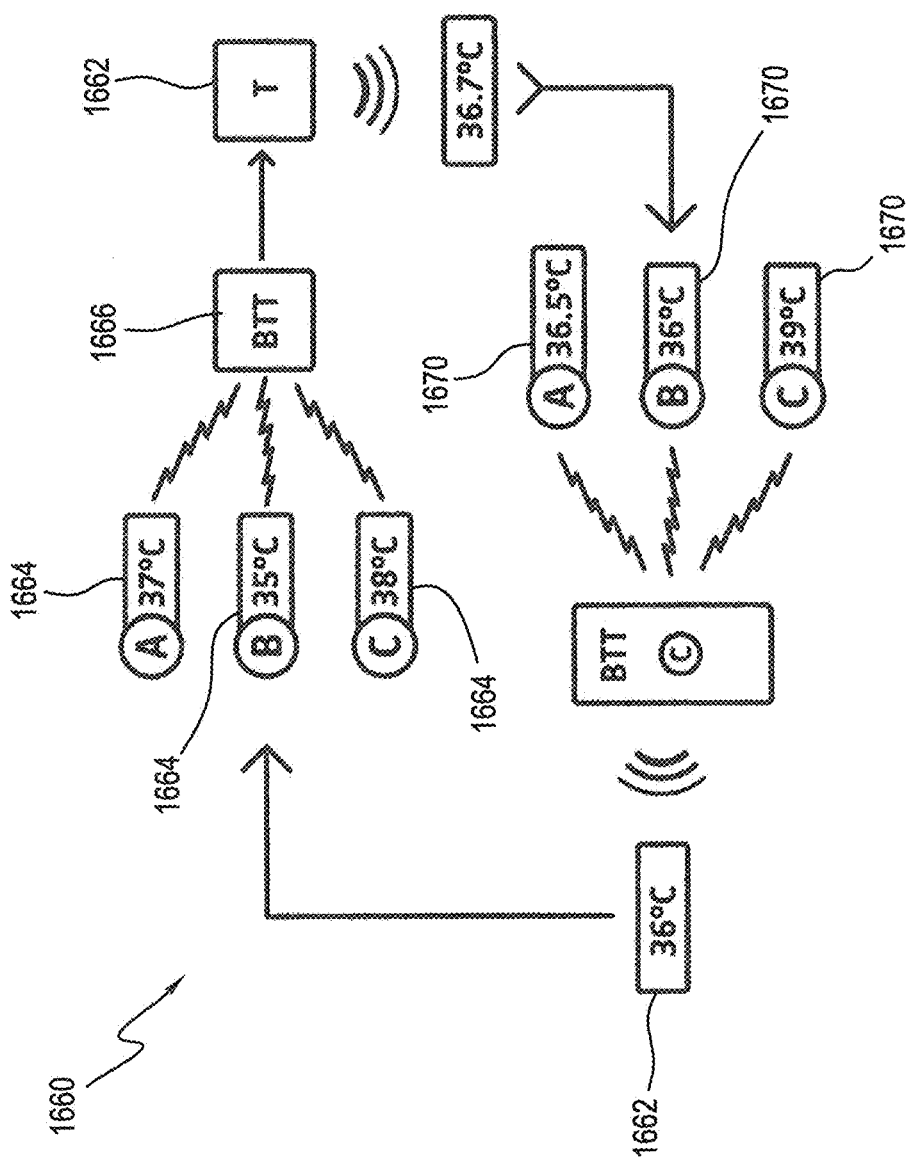
FIG. 113 shows a view of a closed feed-back loop in accordance with an exemplary embodiment of the present disclosure.

FIG. 113 shows a closed feed-back loop system 1660, adapted to modify ambient temperature when more than one signal is being received by a monitoring device, such as when more than one person is present in the same thermal environment, such as a room. Three people, A, B, and C have three different body temperatures 1664, which are detected by each of the individual ABTT sensors 1666 in each person, and three different body temperatures are transmitted to a temperature modification device (TMD) 1662, which in the first step in provides an output based on the average of the three different temperature, resulting in 36.7 degree Celsius, adjusting a thermostat 1668 to 36.7 degree Celsius. After a predetermined amount of time, a new measurement of A, B, and C is transmitted to TMD 1662, but the ambient temperature of 36.7 degrees Celsius caused changed body temperatures 1670 of A, B, and C, with C reaching 39 degrees Celsius. A processor in TMD 1662 takes the largest temperature deviation, herein that occurred in C, to determine the temperature adjustment of TMD 1662. Thus a lower temperature 36 degrees Celsius is the new target ambient temperature. The processor also takes in consideration that temperatures of A and B are close to 36 degrees Celsius to determine new target ambient temperature.

Figure 114:
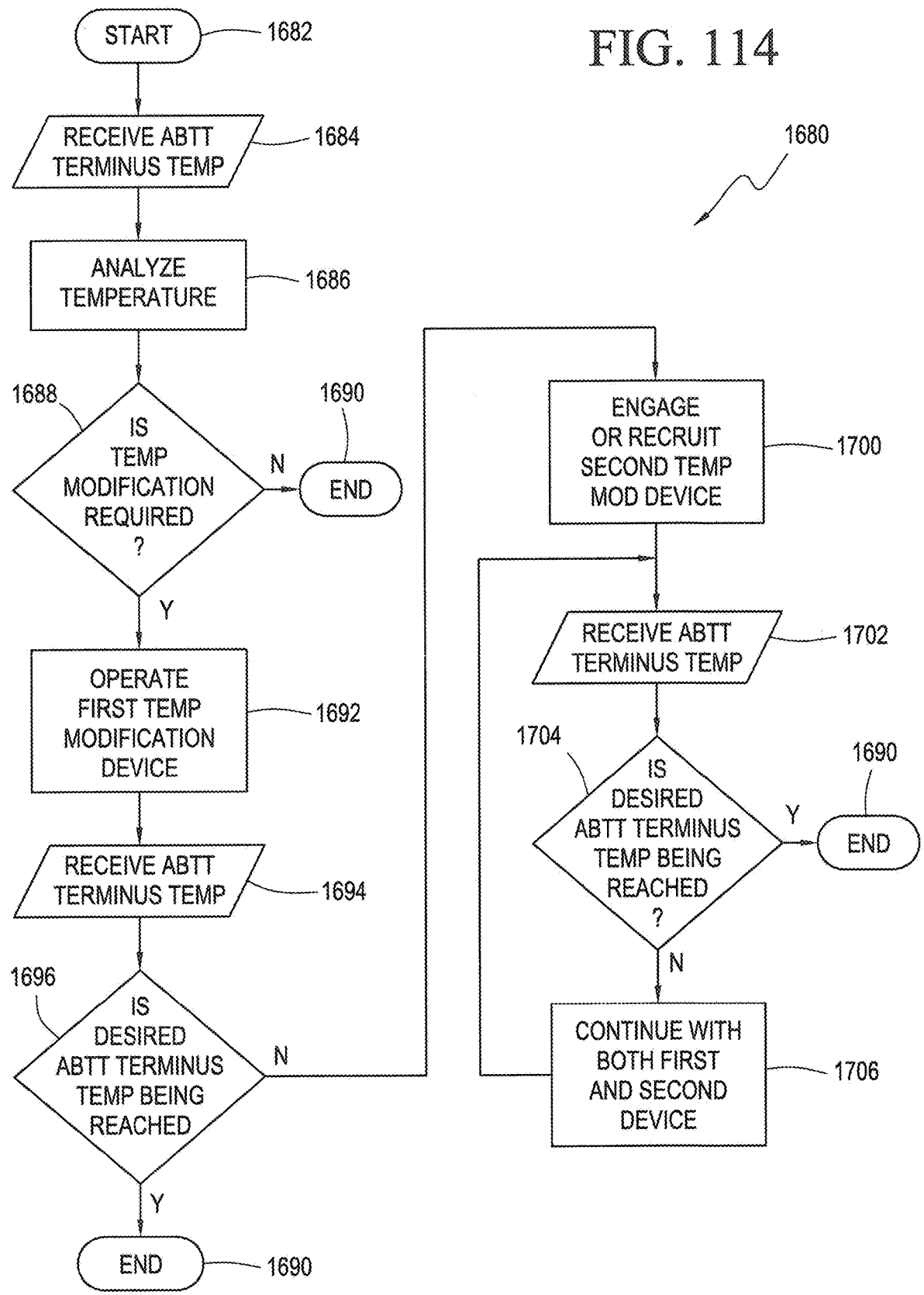
FIG. 114 shows a first process flow in accordance with an exemplary embodiment of the present disclosure.

FIG. 114 shows a first process flow in accordance with an exemplary embodiment of the present disclosure, indicated generally at 1680. Process flow 1680 shows an exemplary process incorporating features described with respect to FIG. 55. Process flow 1680 begins with a start process 1682, where registers can be cleared, initial values set, software and data stored in non-transitory memory can be uploaded or accessed, etc. Control then passage from start process 1682 to a receive ABTT terminus temperature process.

In receive ABTT terminus temperature process 1682, the temperature of one or both ABTT terminuses 10 is received, and then analyzed in a analyze temperature process 1686. Control then passes from analyze temperature process 1686 to a temperature modification decision process 1688, where a decision is made with respect to the need for temperature modification of subject or patient 40. If temperature modification is not needed, control passes to an end process 1690, which terminates process 1680.

If temperature modification is needed, control passes to operate first temperature modification device process 1692, where a first temperature modification device, such as a mattress, is actuated or engaged . . . . Another temperature is then received from ABTT terminus(es) 10 in a receive ABTT terminus temperature process 1694. In a desired ABTT terminus temperature decision process 1696, a determination of whether ABTT terminus(es) 10 are achieving a desired temperature or temperature profile is made. If the desired temperature or temperature profile is being obtained, control passes to end process 1690. If the desire temperature or temperature profile is not being obtained, control passes to an engage or recruit second temperature modification device process 1700, where a second temperature modification device, such as an HVAC system, is activated or actuated. Control then passes to a receive ABTT terminus temperature process 1702, where the temperature of ABTT terminus(es) 10 is received again. Control then passes to a desired ABTT terminus temperature being reached decision process 1704.

If the desired ABTT temperature or temperature profile is being achieved, control passes to end process 1690. If the desired ABTT temperature or temperature profile is not being achieved, control passes to continue temperature modification process 1706, where both the first and second device continue to be operated. Control then passes from continue temperature modification process 1706 to receive ABTT terminus temperature process 1702, which operates as described hereinabove.

Figure 115:
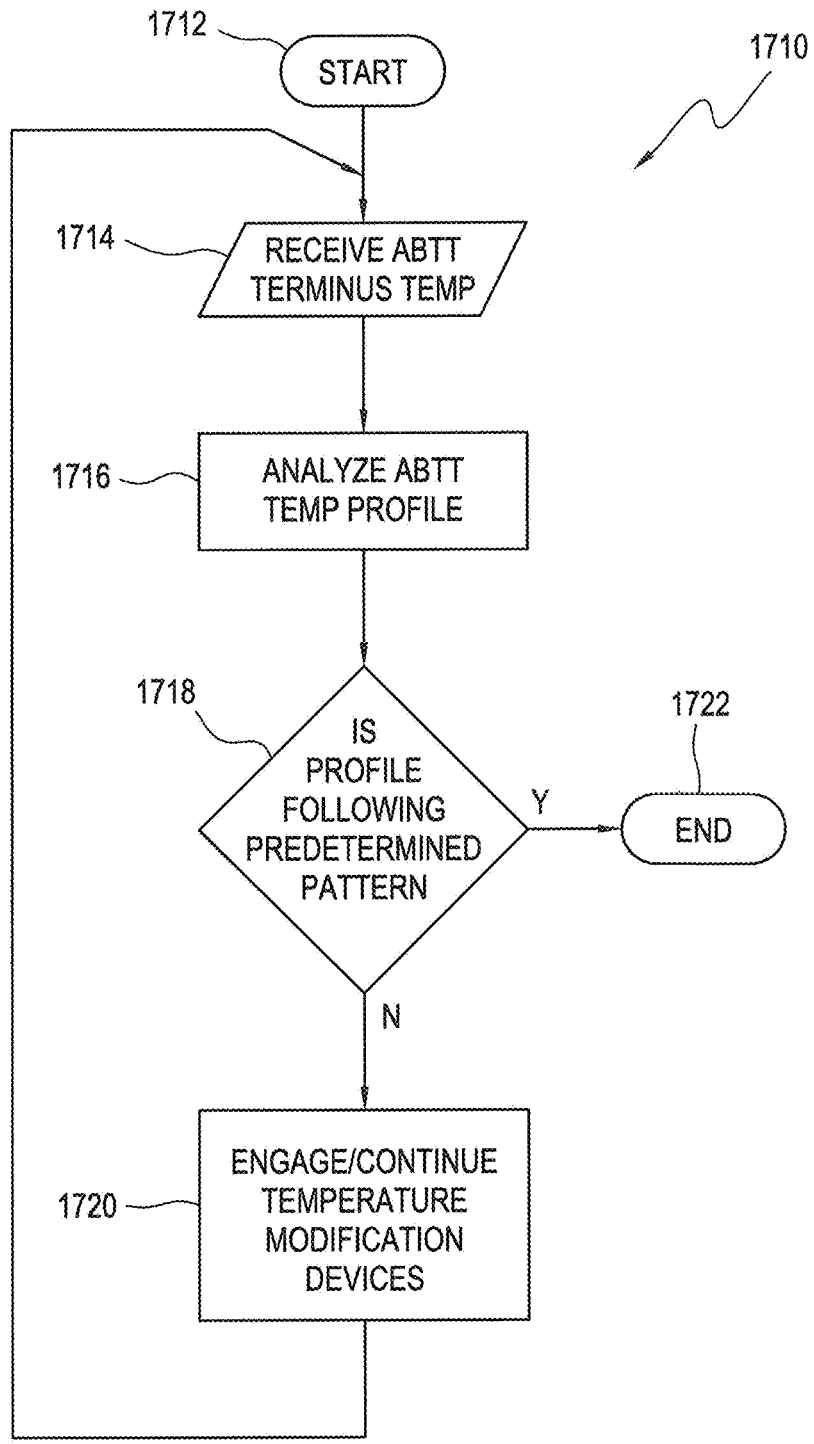
FIG. 115 shows a second process flow in accordance with an exemplary embodiment of the present disclosure.

FIG. 115 shows a second process flow in accordance with an exemplary embodiment of the present disclosure, indicated generally at 1710, referring also to FIG. 107 and the description for FIG. 107. Process 1710 begins with a start process 1712, which can function similar to start process 1682 described hereinabove. Control then passes to a receive ABTT terminus temperature process 1714, where temperatures from one or more ABTT terminus(es) 10 is received, and then to an analyze ABTT terminus temperature process 1716, where the temperatures received from ABTT terminus(es) 10 are analyzed. Control then passes to a temperature profile following a predetermined pattern process 1718. If the temperature(s) received from ABTT terminus(es) 10 is following a predetermined pattern, such as that of FIG. 107, then control passes to an end process 1722, where process 1710 terminates. Otherwise, control passes to an engage or continue temperature modification process 1720. If temperature modification is required and one or more temperature modification devices are available, one or more devices are engaged/actuated at process 1720. If all available temperature modification devices are engaged, they remain engaged at process 1720 and control passes to receive ABTT terminus temperature process 1714, which has been previously described.

Figure 116:
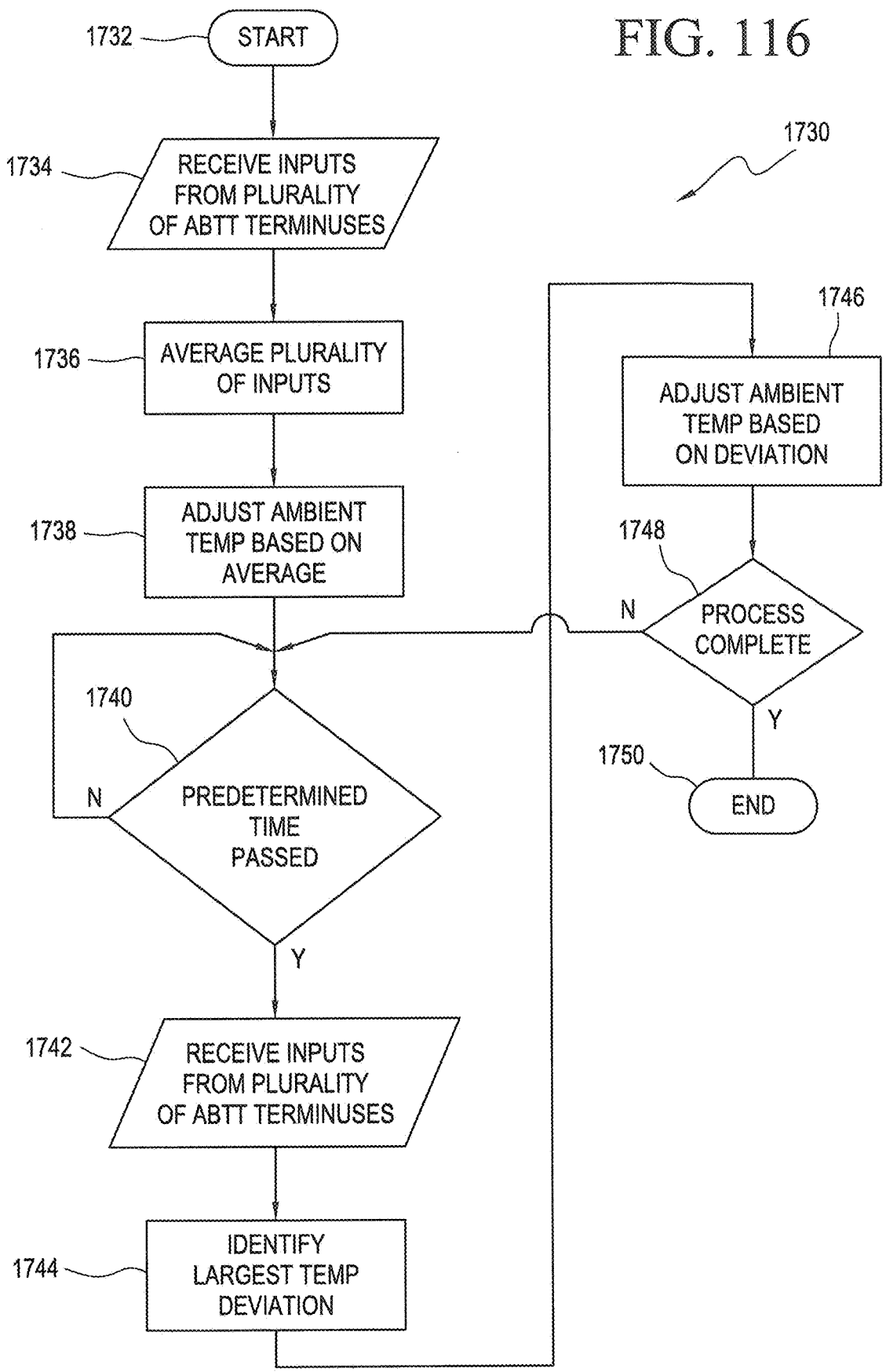
FIG. 116 shows a third process flow in accordance with an exemplary embodiment of the present disclosure.

FIG. 116 shows a third process flow in accordance with an exemplary embodiment of the present disclosure, indicated generally at 1730. Refer also to the description for FIG. 113 provided hereinabove. Process 1730 begins with a start process 1732, which can be similar to start process 1682 described hereinabove. Control then passes to a receive inputs from a plurality of ABTT terminuses 1734, where inputs from ABTT terminuses 10 of plurality of individuals is received. Control then passes to an average plurality of ABTT terminus inputs 1730, where an average of the ABTT terminus temperatures of multiple individuals is average. Control then passes to an adjust ambient temperature process 1738.

In adjust ambient temperature process 1738, environmental controls, such as for an HVAC system, are adjusted to modify the ambient temperature of the room or enclosed space containing the multiple individuals. Control then passes to a predetermined time process 1740, which loops back on itself until a predetermined time, such as at least five minutes, but no more than twenty minutes, has passed. Once the predetermined time has passes, control passes to a receive inputs from a plurality of ABTT terminuses process 1742, where inputs from the ABTT terminuses 10 of multiple individuals is received. Control then passes to an identify largest temperature deviation process 1744, where the largest temperature deviation of all temperatures received from ABTT terminuses 10 of the multiple individuals is identified. Control then passes to an adjust ambient temperature process 1746, where the ambient temperature is adjusted based on the temperature of ABTT terminus 10 of the multiple individuals with the largest temperature deviation. Control then passes to a process complete decision process 1748. If process 1730 is complete, which can occur, for example, if the multiple individuals leave the room or enclosed space, or through a manual over-ride, etc., then control passes to and end process 1750, and process 1730 terminates. Otherwise, control passes to predetermined time process 1740, which functions as described hereinabove.

For the sake of brevity embodiments were shown as exemplary devices. Any part of any embodiment can be used in combination to create a single embodiment, and any part of any embodiment can be used as a replacement or addition to another embodiment, and any combination of embodiments can be considered a single embodiment, and all resultant embodiments are within the scope of the present invention While various embodiments of the disclosure have been shown and described, it is understood that these embodiments are not limited thereto. The embodiments can be changed, modified, and further applied by those skilled in the art. Therefore, these embodiments are not limited to the detail shown and described previously, but also include all such changes and modifications.

I claim:

1. An apparatus for thermal treatment of a brain, the apparatus comprising:
 a temperature sensor positioned on the apparatus and positioned and configured to continuously measure an Abreu brain thermal tunnel (ABTT) terminus temperature, located between an eyebrow and an eye on a human body and configured to continuously transmit a signal representative of the temperature at the ABTT terminus;
 a processor positioned on the apparatus, the processor configured to receive the signal, to determine from the signal a condition of the brain that requires a temperature modification of the brain through way of only the ABTT, and to transmit a control signal simultaneously with the continuous measuring of the temperature of the ABTT and simultaneously with the continuous transmitting of the signal representative of the temperature of the ABTT terminus;

a temperature modification device connected to the apparatus positioned to apply heat and remove heat from a portion of the human body in a location other than that of the ABTT terminus to apply heat and remove heat from the brain as needed, including utilizing the applying of heat and the removal of heat at the location in an alternating fashion until the measured temperature of the ABTT terminus reaches a desired value, the alternating fashion including a plurality of cycles with a maximum heating and a maximum removal of heat changing with each cycle of the plurality of cycles, the temperature modification device configured to receive the control signal to apply heat and remove heat from the brain for the plurality of cycles until the measured temperature of the ABTT terminus reaches the desired value, and configured to apply heat and remove heat from the brain by way of the portion of the human body other than that of the ABTT terminus in response to the control signal to apply heat and remove heat from the brain until the measured temperature of the ABTT terminus reaches the desired value as needed; and a lens positioned on the apparatus in a location in front of an eye, the lens including a notch and the temperature sensor is positioned in the notch to interface with the ABTT terminus.

2. The apparatus of claim 1, wherein the apparatus is supported on a head in a manner that allows for full range of movement without restriction while the human performs activities.

3. The apparatus of claim 1, wherein the apparatus includes a wireless communication device configured to transmit signals to or from the apparatus to a separate electronic device in a manner that allows for full range of movement without restriction while the human performs activities.

4. The apparatus of claim 1, wherein the temperature modification device is positioned on at least one temple of a head in a manner that allows for full range of movement without restriction while the human performs activities.

5. The apparatus of claim 1, wherein the temperature modification device is positioned to extend along a neck between an ear and a shoulder in a manner that allows for full range of movement without restriction while the human performs activities.

6. The apparatus of claim 5, wherein the temperature modification device extends along a carotid artery for at least 125 mm.

7. The apparatus of claim 6, wherein a width of the temperature modification device is at most 95 mm.

8. The apparatus of claim 1, wherein the temperature modification device is positioned to extend along at least one shoulder in a manner that allows for full range of movement without restriction while the human performs activities.

9. The apparatus of claim 8, wherein the temperature modification device is positioned to extend from a region behind an ear, along a neck, and then along the at least one shoulder in a manner that allows for full range of movement without restriction while the human performs activities.

10. The apparatus of claim 1, wherein the temperature modification device extends along a back of a neck in a manner that allows for full range of movement without restriction while the human performs activities.

11. The apparatus of claim 1, wherein the temperature modification device extends across a forehead in a manner that allows for full range of movement without restriction while the human performs activities.

12. The apparatus of claim 1, further including an intubation device attached to and at least partially supported by the apparatus in a manner that allows for full range of movement without restriction while the human performs activities.

13. The apparatus of claim 1, wherein the temperature modification device conforms to a shape of a face in a manner that allows for full range of movement without restriction while the human performs activities.

14. The apparatus of claim 13, wherein the temperature modification device conforms to a shape of an area of the eye, but not on over the eye, in a manner that allows for full range of movement without restriction while the human performs activities.

15. The apparatus of claim 1, wherein the apparatus includes an ear interface to support the apparatus on a pair of ears and a mask to support the apparatus on a face in a manner that allows for full range of movement without restriction while the human performs activities.

16. The apparatus of claim 15, wherein the mask includes a carbon dioxide sensor.

17. The apparatus of claim 1, wherein the temperature modification device further includes a nostril interface for applying heat to or remove heat from the brain by way of a sinus passage in a manner that allows for full range of movement without restriction while the human performs activities.

18. The apparatus of claim 1, wherein the temperature modification device is positioned to extend along at least one blood vessel.

19. The apparatus of claim 18, wherein the at least one blood vessel is near the surface of the skin.

20. The apparatus of claim 18, wherein the temperature modification device includes a dimension that minimizes contact with thermal receptors in areas of the human body adjacent to the at least one blood vessel.

* * * * *